US009883801B2

(12) United States Patent
Stump et al.

(10) Patent No.: US 9,883,801 B2
(45) Date of Patent: Feb. 6, 2018

(54) COMPUTER-IMPLEMENTED SYSTEMS AND METHODS OF AUTOMATED PHYSIOLOGICAL MONITORING, PROGNOSIS, AND TRIAGE

(71) Applicants: Kurt Stump, San Diego, CA (US); Chilezie Nnadi, Solana Beach, CA (US); Alexander Martini, Encinitas, CA (US)

(72) Inventors: Kurt Stump, San Diego, CA (US); Chilezie Nnadi, Solana Beach, CA (US); Alexander Martini, Encinitas, CA (US)

(*) Notice: Subject to any disclaimer, the term of this patent is extended or adjusted under 35 U.S.C. 154(b) by 377 days.

(21) Appl. No.: 14/812,696

(22) Filed: Jul. 29, 2015

(65) Prior Publication Data

US 2016/0029890 A1 Feb. 4, 2016

Related U.S. Application Data

(60) Provisional application No. 62/030,314, filed on Jul. 29, 2014, provisional application No. 62/081,185, filed on Nov. 18, 2014.

(51) Int. Cl.
*A61B 5/00* (2006.01)
*A61B 5/024* (2006.01)
(Continued)

(52) U.S. Cl.
CPC ............ *A61B 5/0022* (2013.01); *A61B 5/021* (2013.01); *A61B 5/0205* (2013.01);
(Continued)

(58) Field of Classification Search
CPC ..................... G06F 19/3431; G06F 19/327
(Continued)

(56) References Cited

U.S. PATENT DOCUMENTS 4,981,139 A 1/1991 Pfohl
5,673,692 A 10/1997 Schulze et al.
(Continued)

FOREIGN PATENT DOCUMENTS

CA 2586839 A1 5/2006
CN 202096392 U 1/2012
(Continued)

OTHER PUBLICATIONS

International Searching Authority, International Search Report for corresponding application No. PCT/US15/42695 dated Oct. 29, 2015, 1pg.
(Continued)

*Primary Examiner* — John R Downey

(57) ABSTRACT

Systems and computer-implemented methods of automated triage prioritization including a mobile communication and display device with a communications interface configured to receive, from a plurality of monitoring devices, electronic signals corresponding to a plurality of real-time physiological parameters, location, and orientation, of a plurality of subjects, and one or more respective environmental parameters. The device also includes program code executable by a processor for generating respective machine and human readable values indicative of the plurality of physiological parameters, location, and orientation, for each subject, generating respective severity scores for each of the plurality of physiological parameters, orientation, and location, generating a prognosis score for each subject, generating a triage prioritization order for the subjects, and displaying the generated respective human readable values for at least two subjects on respective portions of the user interface based on the generated triage prioritization order.

20 Claims, 17 Drawing Sheets

(51) Int. Cl.
*A61B 5/021* (2006.01)
*A61B 5/1455* (2006.01)
*A61B 5/11* (2006.01)
*A61B 5/0205* (2006.01)
*G06F 19/00* (2011.01)
*A61B 5/0402* (2006.01)

(52) U.S. Cl.
CPC ........ *A61B 5/02444* (2013.01); *A61B 5/0402* (2013.01); *A61B 5/11* (2013.01); *A61B 5/14551* (2013.01); *A61B 5/742* (2013.01); *A61B 5/7475* (2013.01); *G06F 19/3431* (2013.01); *A61B 5/72* (2013.01); *A61B 2560/0257* (2013.01); *G06F 19/327* (2013.01)

(58) Field of Classification Search
USPC .................................................. 600/300, 301
See application file for complete search history.

(56) References Cited

U.S. PATENT DOCUMENTS

| | | |
|---|---|---|
| 5,919,141 A | 7/1999 | Money et al. |
| 5,931,791 A | 8/1999 | Saltzstein et al. |
| 6,198,394 B1 | 3/2001 | Jacobsen et al. |
| 6,416,471 B1 | 7/2002 | Kumar et al. |
| 6,419,630 B1 | 7/2002 | Taylor, Jr. et al. |
| 6,544,173 B2 | 4/2003 | West et al. |
| 6,556,852 B1 | 4/2003 | Schulze et al. |
| 6,733,447 B2 | 5/2004 | Lai et al. |
| 7,263,396 B2 | 8/2007 | Chen et al. |
| 7,292,883 B2 * | 11/2007 | De Felice .......... A61B 5/14551 600/324 |
| 7,803,120 B2 | 9/2010 | Banet et al. |
| 8,043,213 B2 | 10/2011 | Hatlestad et al. |
| 8,287,452 B2 | 10/2012 | Young et al. |
| 8,308,641 B2 | 11/2012 | Moroney et al. |
| 8,346,573 B2 | 1/2013 | Glimp et al. |
| 8,352,285 B2 | 1/2013 | Hitney et al. |
| 8,373,556 B2 | 2/2013 | LaLonde et al. |
| 8,403,846 B1 | 3/2013 | Cienfuegos |
| 8,449,469 B2 | 5/2013 | Banet et al. |
| 8,588,880 B2 | 11/2013 | Abdul-Hafiz et al. |
| 8,591,411 B2 | 11/2013 | Banet et al. |
| 8,700,425 B2 | 4/2014 | Hitney et al. |
| 2002/0099277 A1 | 7/2002 | Harry et al. |
| 2008/0077020 A1 | 3/2008 | Young et al. |
| 2008/0165017 A1 | 7/2008 | Schwartz |
| 2009/0131759 A1* | 5/2009 | Sims .................... A61B 5/1135 600/301 |
| 2009/0240116 A1 | 9/2009 | Bluth |
| 2010/0305412 A1 | 12/2010 | Darrah et al. |
| 2011/0137141 A1 | 6/2011 | Razoumov et al. |
| 2012/0203077 A1 | 8/2012 | He et al. |
| 2012/0226112 A1 | 9/2012 | LeBoeuf et al. |
| 2013/0014706 A1 | 1/2013 | Menkes |
| 2013/0035581 A1 | 2/2013 | Vesto |
| 2014/0073043 A1 | 3/2014 | Holmes |
| 2014/0152673 A1* | 6/2014 | Lynn ................. A61B 5/14551 345/473 |
| 2014/0162673 A1 | 6/2014 | Lynn et al. |
| 2014/0227671 A1* | 8/2014 | Olmstead ............... G11B 27/10 434/308 |

FOREIGN PATENT DOCUMENTS

| | | |
|---|---|---|
| EP | 0553372 B1 | 11/1996 |
| WO | 02/22006 A1 | 3/2002 |
| WO | 02/40091 A2 | 5/2002 |
| WO | 2005/046433 A2 | 5/2005 |
| WO | 2009069163 A1 | 6/2009 |
| WO | 2010103390 A1 | 9/2010 |
| WO | 2012112407 A1 | 8/2012 |
| WO | 2013027027 A2 | 2/2013 |

OTHER PUBLICATIONS

Kim, C.S., et al., "Ballistocardiogram as Proximal Timing Reference for Pulse Transit Time Measurement: Potential for Cuffless Blood Pressure Monitoring," IEEE Transactions on Biomedical Engineering, vol. 62, No. 11, Nov. 2015, 10pgs. http://www.ncbi.nlm.nih.gov/pubmed/26054058.

Mukkamala, R., et al., "Toward Ubiquitous Blood Pressure Monitoring Via Pulse Transit Time: Theory and Practice", IEEE Transactions on Biomedical Engineering, vol. 62, No. 8, Aug. 2015, 25pgs. http://www.ncbi.nlm.nih.gov/pubmed/26057530.

Wiens, A., et al., "Wearable Ballistocardiography: Preliminary Methods for Mapping Surface Vibration Measurements to Whole Body Forces", School of Electrical and Computer Engineering, Georgia Institute of Technology, 6pgs. http://ieeexplore.ieee.org/xpl/login.jsp?tp=&arnumber=6944790&url=http%3A%2F%2Fieeexplore.ieee.org%2Fxpls%2Fabs_all.jsp%3Farnumber%3D6944790.

International Bureau of WIPO, International Preliminary Report on Patentability for corresponding International Application No. PCT/US15/42695 dated Jan. 31, 2017, 7pgs.

* cited by examiner

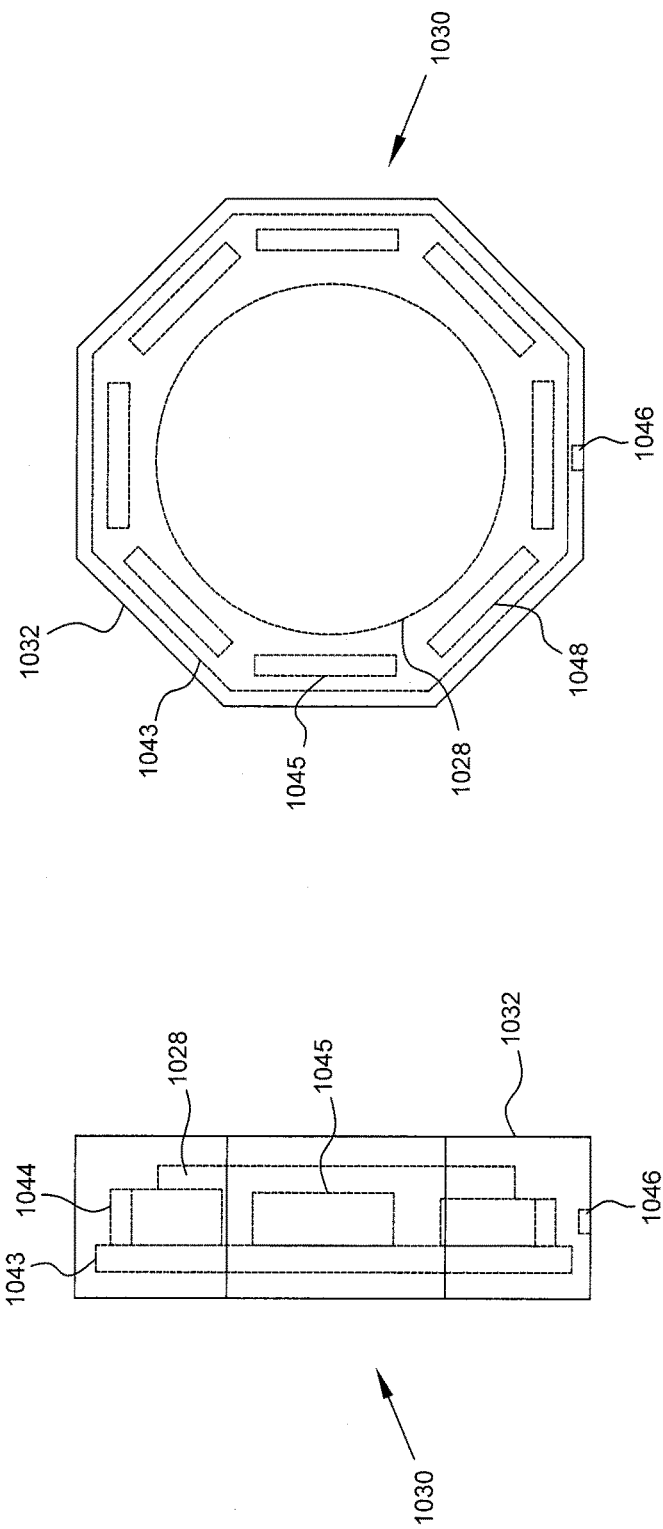

COMPUTER-IMPLEMENTED SYSTEMS AND METHODS OF AUTOMATED PHYSIOLOGICAL MONITORING, PROGNOSIS, AND TRIAGE

CROSS-REFERENCE TO RELATED APPLICATIONS

This application claims priority to U.S. Provisional Patent Application Ser. No. 62/030,314, filed on Jul. 29, 2014, and to U.S. Provisional Patent Application Ser. No. 62/081,185, filed on Nov. 18, 2014, the entirety of which are herein incorporated by reference.

FIELD

The present disclosure is directed generally to monitoring and analyzing data and more particularly to computer implemented systems and methods of automated physiological monitoring, prognosis, and triage.

DESCRIPTION OF THE RELATED ART

Monitoring of a subject's (e.g. an ambulatory or hospitalized patient's) vital or physiological signs has become increasingly important in today's society, particularly those persons and patients who are seriously ill or injured. For example, virtually every hospitalized patient requires periodic measurement and logging of temperature, pulse rate, and blood pressure. Many patients also need frequent determination of respiration rate, cardiac activity, and other physiological signs. Various conventional techniques for monitoring a patient's vital signs rely on dedicated equipment that is either physically attached to the patient or periodically attached to, and removed from, the patient via dexterous, manual means.

However, these conventional monitoring techniques are very costly, and both labor and time-intensive, and such conventional monitoring equipment is very expensive and not readily disposable. These conventional techniques and equipment are also ineffective at monitoring ambulatory patients. Further, such dedicated equipment is highly sensitive, and designed and tested for sterile ambulatory and hospital conditions, which leaves government, commercial, and military health providers and first responders without an effective solution for monitoring ambulatory patients, especially in trauma, battlefield, natural disaster, or terrorist attack, scenarios where mud, blood, and other contaminates are prevalent. In such mass casualty scenarios, government, commercial, and military health providers and first responders have seen the critical need to compress cycle time in their casualty monitoring, evaluation, decision-making, and treatment. In a recently published study from 2001-2009, over 50% of the U.S. combat fatalities in Iraq and Afghanistan died from injuries that were deemed "Potentially Survivable." Many civilian, commercial health sectors also share similar challenges. Current administrative policies, and an aging demographic, have resulted in a 25% annual increase in emergency room wait times. The problem continues to grow as over 800,000 people visit emergency rooms and urgent care centers in the U.S. daily, and longer wait times equate to more deaths, posing a significant risk and liability of a humanitarian disaster. What is needed are cost-effective systems and methods for real-time, continuous monitoring of physiological and environmental parameters of ambulatory, or hospitalized, subjects, and dynamic, automated prognoses, and triage prioritization, in mass casualty scenarios and environments.

Mobile devices such as cellular phones, Personal Digital Assistants (PDAs), smart phones, tablet computers, other wirelessly enabled devices, other portable handheld devices, and hands-free/heads-up devices, have successfully penetrated and been adopted by the general consumer market and by many government entities. Functionalities on mobile devices are generally performed by software applications either in the form of software components that are built-in to the device's mobile operating system or separate mobile applications (also known as "mobile apps" or "apps") that run on the device's operating system. Recently, the development and use of mobile apps has become prevalent and now exist across a wide array of mobile device platforms. Individuals, businesses, and government agencies have come to enjoy, appreciate and rely on the convenience, flexibility and mobility of mobile devices as a means to readily obtain access to information, facilitate communications and interact with friends, family, colleagues and business entities, other friendly deployed units, etc. Thus, it is critical that systems and methods for real-time delivery of information to information users (e.g. first responders, medical providers, etc.) place the information at the fingertips of the users in order to permit enhanced real-time decision-making.

Wearables, such as, for example, Fitbit® wearables, Jawbone® fitness trackers, and the Apple® Watch, have become increasingly popular especially among fitness and health enthusiasts. Conventional wearables are generally worn on the wrist of a user and provide heart rate monitoring, as well as tracking and recording of the user's activity such as steps, distance, calories burned, floors climbed, active minutes, running/walking/cycling pace, exercise workout summaries, sleep, etc. However, deploying such wearables on extremity locations such as the wrist introduces significant errors associated with vital or physiological sign measurement. For example, hair, tattoos, impact, limited blood flow, and motion, restrict and/or introduce inaccuracies associated with various vital sign measurements. Moreover, the body naturally restricts blood flow to extremities during emergency situations (e.g. cold temperatures and emotional stress). Thus, it is critical that systems, methods, and devices for real-time, continuous monitoring of physiological parameters of ambulatory or hospitalized subjects monitor such parameters at body locations that are prone to minimal hair, high blood flow, and/or limited or predictable motion, especially during emergency situations, to ensure accurate results.

Like the accelerated adoption of the Internet itself, cloud computing is rapidly gaining momentum. Cloud computing refers to a computing model for enabling on-demand network access to a shared pool of configurable information technology (IT) capabilities or resources (e.g., networks, servers, storage, applications, and services) that can be rapidly provisioned and released, e.g., with minimal management effort or service provider interaction. Cloud computing allows users to access technology-based services from a network cloud without knowledge of, expertise with, or control over the technology infrastructure that supports them, much as consumers of electric utilities are agnostic as to details of the underlying electrical grid. The cloud is a service provider's offering of abstracted computing-related services. The cloud computing model generally enables on-demand computing self-service, ubiquitous network access, location independent resource pooling, rapid elasticity (e.g., quick demand-based resource scaling), and measured computing service.

Cloud computing models permit service providers to offer services on an on-demand or as-needed (e.g. subscription basis) and customers to purchase (or rent) computer infrastructure-related services as an outsourced service (e.g., on an as-needed or as-consumed basis) instead of having to purchase equipment (e.g., servers, software, data center space, or network equipment) themselves.

SUMMARY

In some embodiments of the present disclosure, a system for automated triage prioritization is provided. The system includes a plurality of monitoring devices, each including a first portion and a second portion, each first portion configured for deployment on a surface opposite a concha of a respective ear of a respective subject. Each first portion of each monitoring device includes a plurality of physiological sensors including a pulse oximetry sensor including an emitter configured to emit light in a direction toward the concha and a receptor configured to receive light reflected from one or more sources in the direction, the pulse oximetry sensor configured to generate an electronic pulse oximetry signal based on the received, reflected light. The plurality of physiological sensors also include a blood pressure sensor including an electrocardiograph sensor configured to monitor an electrical potential at the ear surface and a motion sensor configured to monitor motion at the ear surface relevant to a motion axis, the blood pressure sensor configured to generate an electronic blood pressure signal based on the monitored electrical potential and motion. Each first portion of each monitoring device also includes an orientation sensor configured to monitor an orientation of the respective subject relative to an orientation axis and to generate an electronic orientation signal based on the monitored orientation. Each second portion of each monitoring device includes one or more atmospheric sensors including a pressure sensor configured to monitor ambient pressure around a surface of the respective subject and to generate an electronic ambient pressure signal based on the monitored pressure, and a transmitter configured to transmit the generated electronic signals over a first network.

In some embodiments of the present disclosure, the system for automated triage prioritization also includes a mobile communication and display device including a communications interface configured to be coupled to the first network and to receive the transmitted electronic signals over the first network from each of the transmitters of each of the plurality of monitoring devices, a user interface, a processor coupled to the communications interface, and a non-transient machine-readable storage medium encoded with program code. The program code is executable by the processor for generating respective machine readable values indicative of pulse oximetry, orientation, and blood pressure for each of the subjects using the received electronic signals, generating respective human readable values indicative of pulse oximetry and blood pressure for each of the subjects using the received electronic signals, generating a respective prognosis score for each of the subjects using the generated machine readable values, selecting a triage prioritization order of the subjects using the generated prognosis scores, and displaying the generated respective human readable values for at least two of the subjects on respective portions of the user interface based on the selected triage prioritization order.

In some embodiments of the present disclosure, a computer-implemented method for automated triage prioritization is provided. The computer-implemented method includes, on a mobile communication and display device, communicating with a plurality of monitoring devices via a first network to receive a plurality of electronic signals regarding a plurality of subjects, the received plurality of electronic signals corresponding to a respective plurality of real-time physiological signs, a respective orientation relative to an orientation axis, a respective location, and one or more respective atmospheric conditions, monitored by each of the plurality of monitoring devices. The real-time physiological signs include pulse oximetry, electrical potential, and motion relative to a motion axis, at a surface of the respective monitoring device. The one or more respective atmospheric conditions include ambient pressure around at least a portion of the respective monitoring device. The computer-implemented method also includes, on the mobile communication and display device, retrieving registration information regarding the plurality of monitoring devices from a non-transient memory of the mobile communication and display device, the retrieved registration information binding respective monitoring devices of the plurality of monitoring devices to respective subjects of the plurality of subjects, and generating respective machine readable values indicative of location and orientation of each of the plurality of subjects using the received electronic signals corresponding to location and orientation, and the retrieved registration information.

In some embodiments of the present disclosure, the computer-implemented method also includes, on the mobile communication and display device, generating a respective machine readable value and a respective human readable value indicative of blood pressure for each of the plurality of subjects using the received electronic signals corresponding to motion, electrical potential, and ambient pressure, and the retrieved registration information. The computer-implemented method further includes, on the mobile communication and display device, generating a respective machine readable value and a respective human readable value indicative of pulse oximetry for each of the plurality of subjects using the received electronic signals corresponding to motion and pulse oximetry, and the retrieved registration information, and generating respective severity scores for each of pulse oximetry, orientation, location, and blood pressure, for each of the plurality of subjects using the generated machine readable values for the respective subject and a plurality of pre-determined thresholds. The computer-implemented method also includes, on the mobile communication and display device, generating a respective prognosis score for each of the plurality of subjects using the generated respective severity scores for the respective subject and a plurality of pre-determined weighting factors; generating a triage prioritization order for the plurality of subjects using the generated prognosis scores; detecting a change in the triage prioritization order for at least two subjects of the plurality of subjects based on the generated prognosis scores for the at least two subjects, and information stored in a cache memory of the mobile communication and display device. The stored information includes stored respective prognosis scores for the at least two subjects and a stored triage prioritization order. In response to detecting the change in the triage prioritization order for the at least two subjects, the computer-implemented method also includes, on the mobile communication and display device, changing a display of the respective generated human readable values for the at least two subjects.

In some embodiments of the present disclosure, a system for automated triage prioritization is provided. The system includes a mobile communication and display device including a communications interface configured to be coupled to a first network and to receive transmitted electronic signals regarding a plurality of subjects over the first network from a plurality of monitoring devices. The received plurality of electronic signals correspond to a plurality of real-time physiological parameters monitored at a respective surface of each of the plurality of subjects by a respective one of the plurality of monitoring devices, an orientation relative to an orientation axis, and a location, of each of the plurality of subjects monitored by the respective one of the plurality of monitoring devices, and one or more environmental parameters monitored around each of the plurality of subjects by the respective one of the plurality of monitoring devices. The mobile communication and display device also includes a user interface, a processor coupled to the communications interface, and a non-transient machine-readable storage medium encoded with program code. The program code is executable by the processor for generating respective machine readable values indicative of each of a plurality of physiological signs for each of the respective subjects using the received electronic signals corresponding to the plurality of real-time physiological parameters of each respective subject, and generating respective human readable values indicative of each of at least two of the plurality of real-time physiological signs for each of the subjects using the received electronic signals corresponding to the plurality of real-time physiological parameters of each respective subject, and generating respective machine readable values indicative of each of location and orientation of each of the subjects using the received electronic signals corresponding to the location and orientation of each respective subject.

In some embodiments of the present disclosure, the program code is also executable by the processor for selecting two or monitoring groups based on the generated machine readable values indicative of the respective location of each respective subject. Each of the monitoring groups includes two or more subjects. The program code is also executable by the processor for generating respective severity scores for each of the plurality of physiological signs, orientation, and location for each of the plurality of subjects using the generated machine readable values corresponding to the plurality of real-time physiological parameters of each respective subject and a plurality of pre-determined thresholds, and generating a prognosis score for each of the plurality of subjects using the generated respective severity scores of each respective subject and a plurality of pre-determined weighting factors. The program code is also executable by the processor for generating a respective triage prioritization order for the respective subjects in each monitoring group of the two or more monitoring groups using the generated prognosis scores for the respective subjects in each monitoring group, and displaying the generated respective human readable values for at least two of the respective subjects in at least one monitoring group on respective portions of the user interface based on the generated triage prioritization order for the at least one monitoring group.

BRIEF DESCRIPTION OF THE DRAWINGS

Various aspects of the present disclosure will be or become apparent to one with skill in the art by reference to the following detailed description when considered in connection with the accompanying exemplary non-limiting embodiments.

FIG. 10A is a side elevation view of an example of a second portion of a monitoring device and illustrating internal components of the same according to some embodiments of the present disclosure.

FIG. 10B is a rear elevation view of an example of a second portion of a monitoring device and illustrating internal components of the same according to some embodiments.

DETAILED DESCRIPTION OF THE EXAMPLES

Figure 1:
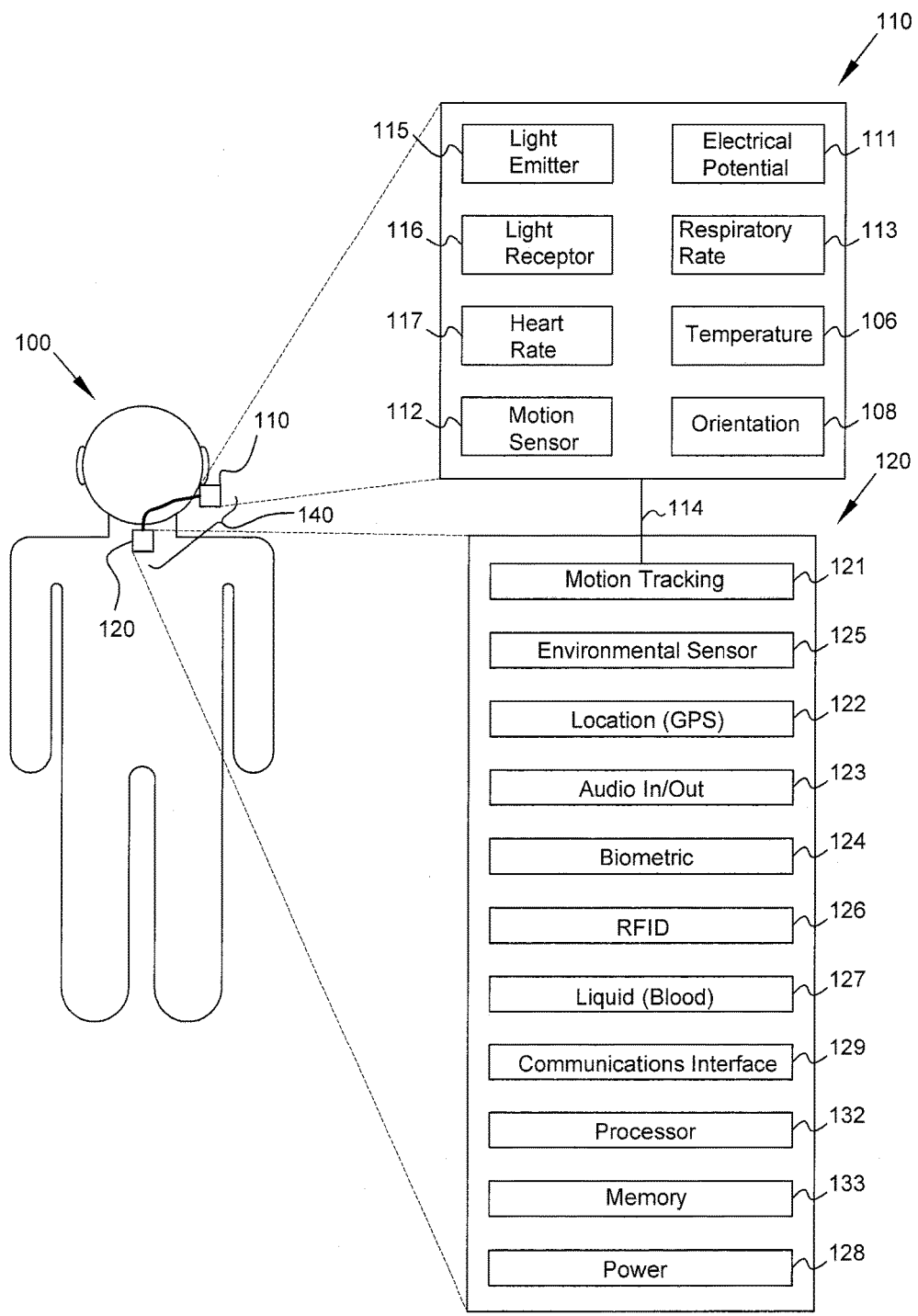
FIG. 1 is a block diagram of an example of a monitoring device in accordance with some embodiments of the present disclosure.

With reference to the Figures, where like elements have been given like numerical designations to facilitate an understanding of the drawings, the various embodiments of systems and computer-implemented methods of automated physiological monitoring, triage, and treatment are described. The figures are not drawn to scale.

Various embodiments address the foregoing deficiencies of prior art systems and methods of monitoring a person's physiological signs and analyzing such information for triage and treatment, especially in trauma, battlefield, emergency room, terrorist attack, or natural disaster scenarios, and provide systems and methods to facilitate dynamic, automatic, real-time prognoses and triage prioritization in such environments to the benefit of government, military, business, individual users (e.g. first responders, emergency medical technicians (EMTs)), patients, and providers of such services, alike. For example, patients benefit from being able to have first responders and EMTs accurately, efficiently treat them and increase the likelihood of saving their lives. Users (first responders, EMTs) benefit from being able to accurately, and in real-time, receive monitored physiological data, prognoses, and triage prioritization, of patients, even in trauma, battlefield, terrorist attack, emergency room, or natural disaster scenarios, to significantly enhance their decision-making and ability to treat subjects and save lives. Government (e.g. military, law enforcement agencies, intelligence agencies) and business (e.g. employers, hospitals) benefit from being able to collect real-time location data, physiological data, prognoses and triage prioritization, to significantly enhance their recordkeeping, provision of care instructions, medical evacuation, casualty evacuation, and alerts notification. Service providers benefit from being able to offer such services on an on-demand or as-needed basis over wireless networks, and the Internet or Web.

The following description is provided as an enabling teaching of a representative set of examples. Many changes can be made to the embodiments described herein while still obtaining beneficial results. Some of the desired benefits discussed below can be obtained by selecting some of the features or steps discussed herein without utilizing other features or steps. Accordingly, many modifications and adaptations, as well as subsets of the features and steps described herein are possible and can even be desirable in certain circumstances. Thus, the following description is provided as illustrative and is not limiting.

This description of illustrative embodiments is intended to be read in connection with the accompanying drawings, which are to be considered part of the entire written description. In the description of embodiments disclosed herein, any reference to direction or orientation is merely intended for convenience of description and is not intended in any way to limit the scope of the present disclosure. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that a system or apparatus be constructed or operated in a particular orientation. Terms such as "attached," "affixed," "connected" and "interconnected," refer to a relationship wherein structures are secured or attached to one another either directly or indirectly through intervening structures, as well as both movable or rigid attachments or relationships, unless expressly described otherwise. The term "adjacent" as used herein to describe the relationship between structures/components includes both direct contact between the respective structures/components referenced and the presence of other intervening structures/components between respective structures/components.

As used herein, use of a singular article such as "a," "an" and "the" is not intended to exclude pluralities of the article's object unless the context clearly and unambiguously dictates otherwise.

The inventors have developed systems and methods of automated prognosis and triage prioritization in trauma situations where the number of subjects (e.g. ambulatory patients, soldiers, victims of terrorist attacks or roadside bombs or natural disasters, emergency room patients) exceeds the number of qualified, available medical personnel, and where triage based on the severity of the injuries is critically important. For example, the inventors have determined that systems and methods provided herein can monitor a plurality of subjects' physiological signs, location, and orientation, and environmental parameters in the subjects' environment, non-invasively and accurately, and wirelessly transmit generated electronic signals including such information to one or more mobile communication and display devices running a native application, web application, or mobile application, programmed to process such electronic signals into machine and human readable values, dynamically and automatically in real-time generate respective severity scores, prognosis scores, and a triage prioritization order, for each of the subjects, and display human readable values of such physiological signs, prognoses, and triage prioritization order, for medics, physicians, EMTs, or first responders, to use in treating the subjects in the order of the most urgent care needed to the least urgent care needed. The inventors have further determined that systems and methods provided herein can significantly compress cycle time of medics, physicians, EMTs, or first responders', casualty monitoring, evaluation, decision-making, and treatment, to save lives.

The inventors have also determined that systems and methods provided herein can register and assign monitoring devices via RFID, QR Code, barcode, or similar identifications, with subjects, subject biometric information, and subject identifying information (e.g. photos, audio, video), in real-time and in battlefield, hospital-like, mass casualty events, emergency room waiting room, natural disaster, roadside bomb, terrorist attack situations. The inventors have additionally determined that systems and methods provided herein can heuristically and predictively model the various subjects' physiological signs with such subjects' medical histories to dynamically and automatically in real-time generate and update respective severity scores, prognosis scores, and triage prioritization orders, for more serious conditions, such as internal bleeding, hemorrhaging, stroke, that would otherwise be unavailable to such medics, physicians, EMTs, or first responders. The inventors have further determined that systems and methods provided herein can provide such heuristically and predictively modeled data to the fingertips of such medics, physicians, EMTs, or first responders, in order to permit enhanced real-time decision-making. The inventors have also determined that systems and methods provided herein can dynamically and automatically in real-time update such subjects' medical histories with physiological signs, location, severity scores, prognosis scores, and other information.

The inventors have further determined that systems and methods provided herein can dynamically and automatically in real-time provide subjects' geolocation data, select monitoring groups, locate subjects, and significantly compress cycle time for triage, care instruction preparation, medical evacuation ("MEDEVAC") or casualty evacuation ("CASEVAC") procedures. The inventors have also determined that systems and methods provided herein can permit real-time two-way communications and transfer of real-time data, such as severity scores, prognosis scores, and triage prioritization order, between EMTs or first responders' and centralized physicians to change prognoses, send alerts or instructions, create MEDEVAC, CASEVAC, and post-injury reports, and modify ambulatory or hospital arrangements, such as which hospital the various subjects will be taken to.

The inventors have also determined that systems and methods provided herein performs continuous collection, of medical data on various subjects, continuous correlations, and other data analyses, with such new data, and places such correlated, updated data at the fingertips of future medics, physicians, EMTs, or first responders in order to permit continuously enhanced real-time decision-making. The inventors have further determined that, for example, the systems and methods described herein can provide continuous health monitoring for a wide variety of government agencies and industries (e.g. law enforcement agencies, military, intelligence agencies, hospitals, contract security, non-governmental organizations, electric power, oil and gas, industrial manufacturing, transportation, retail/consumer, security and facility protection) and automate efforts to significantly shorten cycle times between attack/accident/disaster/injury identification, prognosis, triage, and treatment.

Referring to FIG. 1, a block diagram of an example of a monitoring device 140 in accordance with some embodiments of the present disclosure is provided. In various embodiments, monitoring device 140 is a context-aware physiological and environmental parameters monitoring device. In various embodiments, for example as illustrated in FIG. 1, monitoring device 140 is a non-invasive monitoring device. As shown in FIG. 1, monitoring device 140 may include a first portion 110 and a second portion 120. In various embodiment, first portion 110 of monitoring device 140 is a patch including an adhesive surface. Any suitable adhesive may be utilized to attach a surface of first portion 110 of monitoring device 140 to a surface of a subject 100. In various embodiments, adhesive (not shown) is a biological adhesive that is conducive to the electrical signals of the sensors of monitoring device 140, and configured to adhere to a surface of a subject 100 even in the presence of contaminates such as, for example, mud, blood, sweat, or water, at the site of its application. In various embodiments, adhesive (not shown) is configured to adhere to a surface of the subject in adverse conditions, but also be removed using a peeling force or a solvent.

In various embodiments, first portion 110 of monitoring device 140 is connected to second portion 120 via an electromechanical interconnect 114. In some embodiments, electromechanical interconnect 114 may comprise a variable length, ergonomic, flexible printed circuit and/or associated electronics, connectors, etc., configured to enable communication of electronic signals such as, for example, clock, physiological sensor data, orientation sensor data, motion sensor data, power data, and other data, between an electronic subsystem of first portion 110, an electronic subsystem of second portion 120, and/or external electronics. In some embodiments, electromechanical interconnect 114 may comprise, for example, a plurality of ergonomically designed flexible printed circuits, one or more wires in one or more pliable cable assemblies, optical fibers, one or more printed circuit boards, one or more combinations of flexible printed circuits, cable assemblies, connectors, and printed circuit boards, a part or all of a lanyard that can be worn about or around a neck or other body location of a subject 100. Electromechanical interconnect 114 may also comprise a unique identification value such as, for example, a predetermined resistor value, that is identifiable by an electronic subsystem of first portion 110 and/or an electronic subsystem of second portion 120.

Monitoring device 140 can be deployed on one or more locations on subject 100 such as, for example, on a surface of an ear, the neck, the forehead, a temple, a cheek, the chest, a shoulder, the back, the abdomen, an arm, or a leg, of subject 100. As shown in FIG. 1, in various embodiments, a first portion 110 of monitoring device 140 is deployed on the surface area available on a subject 100 ear opposite the concha area for sensing one or more physiological signs. The inventors have determined that deploying physiological sensors of the monitoring device 140 on a surface opposite a concha of an ear of a subject 100 provides a surface that has high blood flow, in that the tissue beneath the external skin surface of this portion of the ear has a high concentration of capillary beds, and that has limited or predictable motion, even during emergency situations. In various embodiments, such as, for example, where monitoring of physiological parameters of ambulatory or hospitalized patients during emergency situations is required, a first portion 110 of monitoring device 140 may be deployed on a surface opposite a concha of an ear of a subject 100 to ensure accurate results. In various embodiments, first portion 110 of monitoring device 140 includes a single sensor side in that vital or physiological signs of a subject 100 are only monitored on a single side towards a surface of the subject. In various embodiments, monitoring device 140 includes a collection of physiological sensors. In various embodiments, one or more physiological sensors are included in a first portion 110 of monitoring device 140. In various embodiments, the sensors are non-invasive. In various embodiments, monitoring device 140 is a low-cost, disposable device. The inventors have determined that a monitoring device described herein may be bio-contaminated in a pre-hospital or triage environment (e.g. a trauma, battlefield, terrorist attack, emergency room, or natural disaster, environment where mud, blood, sweat, water, and other contaminates are prevalent) and replaced at a low cost. For example, first portion 110 of monitoring device 140 may be a disposable portion including a plurality of physiological sensors and second portion 120 may be a reusable, finitely-reusable, or refurbish able, portion. By way of another example, monitoring device 140 may be a single, disposable unit. In various embodiments, an electronic subsystem of first portion 110 may include a unique identification value such as, for example, a predetermined resistor value, that is identifiable by an electronic subsystem of electromechanical interconnect 114 and/or an electronic subsystem of second portion 120.

In various embodiments, an electronic subsystem of first portion 110 of monitoring device 140 includes a light emitter 115, a light receptor 116, a heart rate sensor 117, a motion sensor 118, an electrical potential sensor 111, a respiratory rate sensor 113, a temperature sensor 116, and an orientation sensor 118. In some embodiments, an electronic subsystem of first portion 110 includes one or more of an electroencephalography (EEG) sensor configured to monitor a subject's brain activity, a blood loss sensor configured to monitor the amount of blood that has been lost from the subject's circulatory system, a liquid (e.g. blood) sensor, a Heart Rate Variability (HRV) sensor, a $CO_2$ sensor configured to monitor the concentration of $CO_2$ in a subject's blood and/or end-tidal $CO_2$, an electrocardiography (ECG) sensor, an electromyography (EMG) sensor, or any suitable sensor.

In various embodiments, light emitter 115 and light receptor 116 include an infrared light emitting diode (LED), red LED, other color LED, a red vertical-cavity surface-emitting laser (VCSEL) diode, an infrared VCSEL diode, other color VCSEL, a multi-wavelength/color LED, a multi-wavelength/color VCSEL diode, and/or a photodiode. In various embodiments, an activated red and infrared LED can be utilized to emit red and infrared light respectively, onto and/or through a surface such as an area on a subject 100 ear opposite the concha area, or other alternative relevant body or other location suitable for sensing relevant physiological signals such as, for example, temperature, blood oxygen saturation (i.e. pulse oximetry ($SpO_2$)), and blood pressure. In various embodiments, first portion 110 of monitoring device 140 includes a pulse oximetry sensor including light emitter 115 and light receptor 116. In various embodiments, a photodiode can be utilized to receive and convert light reflected from a surface of a subject 100 into electric current that can be processed by a pulse oximetry sensor for the purpose of measuring and quantifying physiological signals from the area of the subject illuminated by the infrared LED, red LED and photodiode. In some embodiments, a photodiode can be utilized to receive and convert light that is transmitted through a surface of a subject 100 into electric current. In various embodiments, first portion 110 of monitoring device 140 includes a pulse oximetry sensor including light emitter 115 and light receptor 116. In various embodiments, light emitter 115 is configured to emit light in a direction toward a concha of a subject and light receptor 116 is configured to receive light reflected from the one or more sources (e.g. skin, blood, tissue) in the direction. In various embodiments, the pulse oximetry sensor is configured to generate an electronic pulse oximetry signal based on the received, reflected light. In various embodiments, pulse oximetry sensor includes one or more filters that are pre-programmed or pre-configured to filter reflected light from sources other than blood. In various embodiments, pulse oximetry sensor may sense and/or process ambient light to calibrate readings of light emitter 115 and light receptor 116. In various embodiments, pulse oximetry sensor is a minimal footprint (e.g. 0.05-75 millimeter (mm) (length), 0.05-75 mm (width), 0.05-25 mm (height)) and low-power (e.g. 0.1-5 milliwatts (mW)) pulse oximetry analog and/or digital front-end integrated circuit including supporting electronics, designed, fabricated, and assembled on one or more layers of one or more flexible printed circuit and/or printed circuit board that constitutes part of an electronic subsystem of first portion 110. In various embodiments, a pulse oximetry sensor includes a plurality of interfaces to external electronics and/or external physical parameters such as, for example, a first interface to enable the supply of electricity to the sensor via electromechanical interconnect 114 and from a power source subsystem 128 that is part of an electronic subsystem of second portion 120 of monitoring device 140, a second interface to coordinate transmission and/or reception of electronic signals such as, for example, digital control signals, variable analog signals, etc., to and/or from the light emitter 115 and light receptor 116 (e.g. infrared LED, red LED and photodiode), and a third interface to coordinate transmission and/or reception of electronic signals such as a clock, processed physiological signals data, etc., to and/or from a processor subsystem 132 that is part of an electronic subsystem of second portion 120 of monitoring device 140. In various embodiments, light emitter 115 and light receptor 116 provide an electronic signal input to respiratory rate sensor 113.

In various embodiments, motion sensor 112 includes, for example, a multi-motion axis gyroscope, a multi-motion axis accelerometer, a multi-motion axis magnetometer, or combinations thereof. Any suitable number of axes can be utilized for the multi-motion axis motion sensor 112. In various embodiments, motion sensor 112 includes a tri-axis accelerometer providing nine (9) axes of motion. In various embodiments, the number of axes for the multi-motion axis motion sensor 112 is six (6). In some embodiments, the number of axes for the multi-motion axis motion sensor 112 is eight (8). In various embodiments, motion sensor 112 is a minimal footprint (e.g. 0.05-75 mm (length), 0.05-75 mm (width), 0.05-25 mm (height)) and low-power (e.g. 0.1-10 mW) motion tracking integrated circuit including supporting electronics, designed, fabricated, and assembled on one or more layers of one or more flexible printed circuit and/or printed circuit board that constitutes part of an electronic subsystem of first portion 110. In various embodiments, a motion sensor 112 includes a plurality of interfaces to external electronics and/or external physical parameters such as, for example, a first interface to enable the supply of electricity to the sensor via electromechanical interconnect 114 and from a power source subsystem 128 that is part of an electronic subsystem of second portion 120 of monitoring device 140, a second interface to a plurality of intricate microelectromechanical structures internal to the integrated circuit of motion sensor 112 which include structures configured to be physically displaced in response to movement at the deployed surface of subject 100 such as, for example, a series of overlapping cantilever structures, and a third interface to coordinate transmission and/or reception of electronic signals such as a clock, processed physiological signals data, etc., to and/or from a processor subsystem 132 that is part of an electronic subsystem of second portion 120 of monitoring device 140. In various embodiments, motion sensor 112 is configured to monitor motion of a subject relative to a motion axis and to generate an electronic motion signal based on the monitored motion. In various embodiments, motion sensor 112 is configured to detect motion of a subject's head in response to heart beat to generate an electronic ballistocardiograph (BCG) signal. In various embodiments, motion sensor 112 provides an electronic signal input to a blood pressure sensor. In various embodiments, first portion 110 of monitoring device 140 includes a blood pressure sensor including motion sensor 112. In various embodiments, motion sensor 112 provides an electronic signal input to respiratory rate sensor 113 and/or heart rate sensor 117.

In various embodiments, orientation sensor 118 includes, for example, a multi-orientation axis gyroscope, a multi-orientation axis accelerometer, a multi-orientation axis magnetometer, or combinations thereof. Any suitable number of axes can be utilized for the multi-orientation axis orientation sensor 118. In various embodiments, first portion 110 of monitoring device 140, including an orientation sensor 118, may be affixed to a surface on a subject 100 ear opposite the concha, or other alternative relevant body surface. In various embodiments, orientation sensor 118 may sense and/or process movements of the subject such as, for example, movements associated with sitting, standing, walking, lying face down, laying face up, or any other suitable orientation, including subtle localized body movements that can be correlated to internal biological activities or signals such as breathing rate, etc. In various embodiments, orientation sensor 118 includes a tri-axis accelerometer providing nine (9) axes of orientation. In various embodiments, the number of axes for the multi-orientation axis orientation sensor 118 is six (6). In some embodiments, the number of axes for the multi-orientation axis orientation sensor 118 is eight (8). In various embodiments, orientation sensor 118 is a minimal footprint (e.g. 0.05-75 mm (length), 0.05-75 mm (width), 0.05-25 mm (height)) and low-power (e.g. 0.1-10 mW) orientation tracking integrated circuit including supporting electronics, designed, fabricated, and assembled on one or more layers of one or more flexible printed circuit and/or printed circuit board that constitutes part of an electronic subsystem of first portion 110. In various embodiments, an orientation sensor 118 includes a plurality of interfaces to external electronics and/or external physical parameters such as, for example, a first interface to enable the supply of electricity to the sensor via electromechanical interconnect 114 and from a power source subsystem 128 that is part of an electronic subsystem of second portion 120 of monitoring device 140, a second interface to a plurality of intricate microelectromechanical structures internal to the integrated circuit of orientation sensor 118 which include structures configured to be physically displaced in response to movement at the deployed surface of subject 100 such as, for example, a series of overlapping cantilever structures, and a third interface to coordinate transmission and/or reception of electronic signals such as a clock, processed physiological signals data, etc., to and/or from a processor subsystem 132 that is part of an electronic subsystem of second portion 120 of monitoring device 140. In various embodiments, orientation sensor 118 is configured to monitor an orientation of a subject relative to an orientation axis and to generate an electronic orientation signal based on the monitored orientation. In various embodiments, motion sensor 112 and orientation sensor 118 are the same sensor. In various embodiments, motion axes of motion sensor 112 and orientation axes of orientation sensor 118 are the same axes.

In various embodiments, first portion 110 of monitoring device 140, including a temperature sensor 116, can be deployed on a surface of subject 100 (e.g. a surface opposite a concha of an ear of a subject 100) and may be utilized to sense and/or process physiological parameters such as, for example, body temperature or skin temperature. In some embodiments, temperature sensor 116 can be deployed on a surface of subject 100 and used to process environmental parameters such as, for example, ambient temperature. In various embodiments, temperature sensor 116 includes, for example, a transducer integrated circuit configured to utilize silicon structures contained therein to sense ambient temperature, a resistance temperature detector (RTD), a thermistor, a thermocouple, or combinations thereof. In various embodiments, temperature sensor 116 includes an infrared thermopile sensor. In various embodiments, temperature sensor 116 is a minimal footprint (e.g. 0.05-75 mm (length), 0.05-75 mm (width), 0.05-25 mm (height)) and low-power (e.g. 0.1-5 mW) infrared thermopile sensor integrated circuit including supporting electronics, designed, fabricated, and assembled on one or more layers of one or more flexible printed circuit and/or printed circuit board that constitutes part of an electronic subsystem of first portion 110. In various embodiments, temperature sensor 116 includes an integrated math engine configured to process electronic signals received from one or more infrared thermopile sensors within an integrated circuit. In various embodiments, temperature sensor 116 includes a plurality of interfaces to external electronics and/or external physical parameters such as, for example, a first interface to enable the supply of electricity to the sensor via electromechanical interconnect 114 and from a power source subsystem 128 that is part of an electronic subsystem of second portion 120 of monitoring device 140, a second interface to materials such as, for example, a thermopile, having physical properties sensitive to variations in ambient temperature, and a third interface to coordinate transmission and/or reception of electronic signals such as a clock, processed physiological signals data, etc., to and/or from a processor subsystem 132 that is part of an electronic subsystem of second portion 120 of monitoring device 140. In various embodiments, temperature sensor 116 can be configured to monitor a temperature at a surface, and/or a temperature around a surface, of a subject 100 and to generate an electronic temperature signal based on the monitored temperature.

In various embodiments, first portion 110 of monitoring device 140, including an electrical potential sensor 111, can be deployed on a surface of subject 100 (e.g. a surface opposite a concha of an ear of a subject 100) and may be utilized to measure electrical potential at the surface of the subject 100. In various embodiments, an electrocardiograph (ECG or EKG) sensor can include electrical potential sensor 111. In various embodiments, an electromyograph (EMG) sensor, and/or an electroencephalograph (ECG) sensor, can include electrical potential sensor 111. In various embodiments, electrical potential sensor 111 is a minimal footprint (e.g. 0.05-75 mm (length), 0.05-75 mm (width), 0.05-25 mm (height)) sensor including one or more electrodes having rectilinear and/or non-rectilinear forms that are designed, fabricated, and assembled on one or more layers of one or more flexible printed circuit and/or printed circuit board that constitutes part of an electronic subsystem of first portion 110. In various embodiments, electrical potential sensor 111 includes a plurality of interfaces to external electronics and/or external physical parameters such as, for example, a first interface to enable the supply of electricity to the sensor via electromechanical interconnect 114 and from a power source subsystem 128 that is part of an electronic subsystem of second portion 120 of monitoring device 140, a second interface to one or more electrodes, and/or a capacitive touch controller subsystem of monitoring device 140 to coordinate transmission and reception of electronic signals such as changes in ambient capacitance to/from electrical potential sensor 111, and a third interface to coordinate transmission and/or reception of electronic signals such as a clock, processed physiological signals data, etc., to and/or from a processor subsystem 132 that is part of an electronic subsystem of second portion 120 of monitoring device 140. In various embodiments, electrical potential sensor 111 can be configured to monitor an electrical potential at a surface of a subject 100 and to generate an electronic electrical potential signal based on the monitored electrical potential. In various embodiments, electrical potential sensor 111 provides an electronic signal input to respiratory rate sensor 113. In various embodiments, electrical potential sensor 111 provides an electronic signal input to a blood pressure sensor. In various embodiments, a blood pressure sensor (not shown), is configured to generate an electronic blood pressure signal based on the electrical potential monitored by electrical potential sensor 111 and the motion monitored by motion sensor 112. In various embodiments, a blood pressure sensor (not shown), is an arterial blood pressure sensor configured to monitor a subject's systolic and/or diastolic blood pressures and to generate an electronic systolic and/or diastolic blood pressure signal based on the monitored systolic and/or diastolic blood pressures.

In various embodiments, first portion 110 of monitoring device 140, including heart rate sensor 117, can be deployed on a surface of subject 100 (e.g. a surface opposite a concha of an ear of a subject 100) and may be utilized to sense and/or process heart rate of a subject 100. In various embodiments, heart rate sensor 117 includes, for example, an electrical potential sensor as described above, a motion sensor as described above, a light emitter and light receptor as described above, or combinations thereof. In various embodiments, heart rate sensor 117 is a minimal footprint (e.g. 0.05-75 mm (length), 0.05-75 mm (width), 0.05-25 mm (height)) and low-power (e.g. 0.1-5 mW) integrated circuit including supporting electronics, designed, fabricated, and assembled on one or more layers of one or more flexible printed circuit and/or printed circuit board that constitutes part of an electronic subsystem of first portion 110. In various embodiments, heart rate sensor 117 includes an integrated math engine configured to process electronic signals received from one or more of electrical potential sensor 111, motion sensor 112, light emitter 115 and light receptor 116 within an integrated circuit. In various embodiments, heart rate sensor 117 includes a plurality of interfaces to external electronics and/or external physical parameters such as, for example, a first interface to enable the supply of electricity to the sensor via electromechanical interconnect 114 and from a power source subsystem 128 that is part of an electronic subsystem of second portion 120 of monitoring device 140, a second interface to electrical potential sensor 111, motion sensor 112, light emitter 115 and light receptor 116, and a third interface to coordinate transmission and/or reception of electronic signals such as a clock, processed physiological signals data, etc., to and/or from a processor subsystem 132 that is part of an electronic subsystem of second portion 120 of monitoring device 140. In various embodiments, heart rate sensor 117 can be configured to monitor a pulse rate of a subject 100 and to generate an electronic heart rate signal based on the monitored pulse rate.

In various embodiments, first portion 110 of monitoring device 140, including respiratory rate sensor 113, can be deployed on a surface of subject 100 (e.g. a surface opposite a concha of an ear of a subject 100) and may be utilized to sense and/or process respiratory rate of a subject 100. In various embodiments, respiratory rate sensor 113 includes, for example, an electrical potential sensor as described above, a motion sensor as described above, or combinations thereof. In various embodiments, respiratory rate sensor 113 includes, for example, an acoustic transducer integrated circuit configured to sense respiratory rate. In various embodiments, respiratory rate sensor 113 is a minimal footprint (e.g. 0.05-75 mm (length), 0.05-75 mm (width), 0.05-25 mm (height)) and low-power (e.g. 0.1-5 mW) integrated circuit including supporting electronics, designed, fabricated, and assembled on one or more layers of one or more flexible printed circuit and/or printed circuit board that constitutes part of an electronic subsystem of first portion 110. In various embodiments, respiratory rate sensor 113 includes an integrated math engine configured to process electronic signals received from one or more of electrical potential sensor 111, motion sensor 112, an acoustic transducer integrated circuit, within an integrated circuit. In various embodiments, respiratory rate sensor 113 includes a plurality of interfaces to external electronics and/or external physical parameters such as, for example, a first interface to enable the supply of electricity to the sensor via electromechanical interconnect 114 and from a power source subsystem 128 that is part of an electronic subsystem of second portion 120 of monitoring device 140, a second interface to electrical potential sensor 111, motion sensor 112, and/or an acoustic transducer integrated circuit, and a third interface to coordinate transmission and/or reception of electronic signals such as a clock, processed physiological signals data, etc., to and/or from a processor subsystem 132 that is part of an electronic subsystem of second portion 120 of monitoring device 140. In various embodiments, respiratory rate sensor 113 can be configured to monitor a breathing rate of a subject 100 and to generate an electronic respiratory rate signal based on the monitored respiratory rate.

Second portion 120 of monitoring device 140 can be deployed on one or more locations on subject 100 such as, for example, on a surface of the ear, the neck, the forehead, the temple, the cheek, the chest, the shoulder, the back, the abdomen, the arms, or the legs, of subject 100. As shown in FIG. 1, in various embodiments, a second portion 120 of monitoring device 140 is deployed on the surface area available on a subject 100 neck such as, for example, slightly below the hair line and above the collar of a subject 100, for sensing one or more environmental parameters, and transmitting generated electronic signals and electronic signals received from first portion 110 over a network. In various embodiments, second portion 120 of monitoring device 140 is deployed on a minimally intrusive surface area available on a subject 100. In various embodiments, second portion 120 of monitoring device 140 may include an adhesive surface. Any suitable adhesive may be utilized to attach a surface of second portion 120 of monitoring device 140 to a surface of a subject 100. In various embodiments, second portion 120 of monitoring device 140 may include a device such as, for example, a clip or a pin, to attach second portion 120 to an item of clothing, lanyard, etc., worn by subject 100 such as, for example, the collar or pocket of a shirt. In various embodiments, monitoring device 140 includes one or more environmental sensors. In various embodiments, second portion 120 of monitoring device 140 includes one or more environmental sensors. In various embodiments, the sensors are non-invasive.

In various embodiments, as illustrated in FIG. 1, an electronic subsystem of second portion 120 of monitoring device 140 may include a motion tracking subsystem 121, one or more environmental sensors 125, a location (e.g. global positioning system (GPS)) subsystem 122, an audio input/output subsystem 123, a biometric subsystem 124, a radio frequency identification (RFID) subsystem 126, a liquid (e.g. blood) sensor 127, communications interface 129, processor 132, memory 133, and/or a power subsystem 128. In various embodiments, the one or more environmental sensors 125 may include, for example, an ambient temperature sensor, an ambient pressure sensor, a humidity sensor, a UV index sensor, an ambient light sensor, or combinations thereof. Any suitable environmental sensor may be included as the one or more environmental sensors 125 in second portion 120 of monitoring device 140. In various embodiments, an electronic subsystem of second portion 120 may include a unique identification value such as, for example, a predetermined resistor value, that is identifiable by an electronic subsystem of electromechanical interconnect 114 and/or an electronic subsystem of first portion 110.

In various embodiments, second portion 120 of monitoring device 140, including a pressure sensor, can be deployed on a surface of subject 100 (e.g. a surface of a neck of a subject 100), or a surface of clothing worn by a subject 100, and may be utilized to monitor ambient pressure (e.g. atmospheric pressure) around the surface of the subject 100 or the subject's clothing. In various embodiments, pressure sensor includes one or more minimal footprint (e.g. 0.05-75 mm (length), 0.05-75 mm (width), 0.05-25 mm (height)) and low-power (e.g. 0.1-5 mW) barometer integrated circuits including supporting electronics, designed, fabricated, and assembled on one or more layers of one or more flexible printed circuit and/or printed circuit board that constitutes part of an electronic subsystem of second portion 120. In various embodiments, such one or more barometer integrated circuits can include analog and/or digital front-end circuitry configured to process electronic signals from a pressure sensing element within the integrated circuit. In various embodiments, a pressure sensor includes a plurality of interfaces to external electronics and/or external physical parameter such as, for example, a first interface to enable the supply of electricity to the sensor from power source subsystem 128 that is part of an electronic subsystem of second portion 120 of monitoring device 140, a second interface to a plurality of microelectromechanical structures internal to said integrated circuit that may be configured to be physically displaced and/or deflected in response to variation in ambient pressure around the deployed surface of subject 100 such as, for example, a suspended diaphragm, and a third interface to coordinate transmission and/or reception of electronic signals such as a clock, processed environmental signals data, etc., to and/or from processor 132. In various embodiments, a pressure sensor may be configured to sense and/or process environmental signals such as air pressure around a surface of a subject, or the subject's clothing. In various embodiments, a pressure sensor can be configured to monitor ambient pressure around a surface of a subject 100 and to generate an electronic ambient pressure signal based on the monitored ambient pressure. In various embodiments, a pressure sensor may sense and/or process ambient pressure to calibrate, or provide a quantified context for, sensed blood oxygen saturation data received by second portion 120 via electromechanical interconnect 114 in the form of electronic signals generated by a pulse oximetry sensor of first portion 110.

In various embodiments, second portion 120 of monitoring device 140, including a humidity sensor, can be deployed on a surface of subject 100 (e.g. a surface of a neck of a subject 100), or a surface of clothing worn by a subject 100, and may be utilized to monitor humidity around the surface of the subject 100 or the subject's clothing. In various embodiments, humidity sensor includes one or more minimal footprint ((e.g. 0.05-75 mm (length), 0.05-75 mm (width), 0.05-25 mm (height)) and low-power (e.g. 0.1-5 mW) humidity sensor integrated circuits including supporting electronics, designed, fabricated, and assembled on one or more layers of one or more flexible printed circuit and/or printed circuit board that constitutes part of an electronic subsystem of second portion 120. In various embodiments, such humidity sensor integrated circuits can include a temperature sensor and an integrated signal processor configured to process electronic signals received from one or more humidity sensor devices within said integrated circuit. In various embodiments, a humidity sensor includes a plurality of interfaces to external electronics and/or external physical parameters such as, for example, a first interface to enable the supply of electricity to the sensor from power source subsystem 128 that is part of an electronic subsystem of second portion 120 of monitoring device 140, a second interface to materials that are designed and assembled in such a manner as to be sensitive to humidity-related variations in their localized environment such as, for example, a dielectric material (e.g. polyamide), and a third interface to coordinate transmission and/or reception of electronic signals such as a clock, processed environmental signals data, etc., to and/or from processor 132. In various embodiments, a humidity sensor may be configured to sense and/or process environmental signals such as, for example, humidity and temperature around a surface of a subject. In various embodiments, a humidity sensor can be configured to monitor ambient humidity around a surface of a subject 100 and to generate an electronic ambient humidity signal based on the monitored ambient humidity. In various embodiments, a humidity sensor may sense and/or process ambient humidity to calibrate, or provide a quantified context for, liquid data monitored at liquid (e.g. blood) sensor 127 of second portion 120.

In various embodiments, second portion 120 of monitoring device 140, including a UV index sensor and an ambient light sensor, can be deployed on a surface of subject 100 (e.g. a surface of a neck of a subject 100), or a surface of clothing worn by a subject 100, and may be utilized to monitor UV index and ambient light around the surface of the subject 100 or the subject's clothing. In various embodiments, UV index sensor and ambient light sensor include one or more minimal footprint (e.g. 0.05-75 mm (length), 0.05-75 mm (width), 0.05-25 mm (height)) and low-power (e.g. 0.1-5 mW) integrated circuits including supporting electronics, designed, fabricated, and assembled on one or more layers of one or more flexible printed circuit and/or printed circuit board that constitutes part of an electronic subsystem of second portion 120. In various embodiments, such integrated circuits can include a proximity sensor, analog and/or digital front-end circuitry, and a signal processor configured to process electronic signals from UV sensor, ambient light, and proximity sensor elements within the integrated circuit. In some embodiments, the UV index sensor, the ambient light sensor, and the proximity sensor are implemented in separate integrated circuits or combinations thereof. In various embodiments, a UV index sensor and/or an ambient light sensor include a plurality of interfaces to external electronics and/or external physical parameters such as, for example, a first interface to enable the supply of electricity to the sensor from power source subsystem 128 that is part of an electronic subsystem of second portion 120 of monitoring device 140, a second interface to structures of, for example, one or more light (e.g. infrared) emitters, photodiodes, light receptors, that are internal to an integrated circuit and may be configured to emit light and/or receive light from their respective environment, and a third interface to coordinate transmission and/or reception of electronic signals such as a clock, processed environmental signals data, etc., to and/or from processor 132. In various embodiments, a UV index sensor and/or an ambient light sensor may be configured to sense and/or process environmental signals such as, for example, UV index and/or ambient light around a surface of a subject. In various embodiments, a UV index sensor and/or an ambient light sensor can be configured to monitor UV index and/or ambient light around a surface of a subject 100, or the subject's clothing, and to generate an electronic UV index and/or ambient light signal based on the monitored UV index and/or ambient light. In various embodiments, a UV index sensor and/or an ambient light sensor may sense and/or process ambient light to calibrate, or provide a quantified context for, sensed blood oxygen saturation data received by second portion 120 via electromechanical interconnect 114 in the form of electronic signals generated by a pulse oximetry sensor of first portion 110.

In various embodiments, second portion 120 of monitoring device 140, including an ambient temperature sensor, can be deployed on a surface of subject 100 (e.g. a surface of a neck of a subject 100), or a surface of clothing worn by a subject 100, and may be utilized to monitor ambient temperature around the surface of the subject 100 or the subject's clothing. In various embodiments, ambient temperature sensor includes, for example, a transducer integrated circuit configured to utilize silicon structures contained therein to sense ambient temperature, a resistance temperature detector (RTD), a thermistor, a thermocouple, or combinations thereof, as described above for temperature sensor 116. In various embodiments, ambient temperature sensor includes an infrared thermopile sensor. In various embodiments, an ambient temperature sensor may be configured to sense and/or process environmental signals such as air temperature around a surface of a subject, or the subject's clothing. In various embodiments, an ambient temperature sensor can be configured to monitor ambient temperature around a surface of a subject 100, or the subject's clothing, and to generate an electronic ambient temperature signal based on the monitored ambient temperature. In various embodiments, an ambient temperature may sense and/or process ambient temperature to calibrate, or provide a quantified context for, skin and/or body temperature data received by second portion 120 via electromechanical interconnect 114 in the form of electronic signals generated by a temperature sensor of first portion 110.

In various embodiments, second portion 120 of monitoring device 140, including motion tracking subsystem 121, can be deployed on a surface of subject 100 (e.g. a surface of a neck of a subject 100), or a surface of clothing worn by a subject 100, and may be utilized to monitor motion of the subject 100. In various embodiments, motion tracking subsystem 121 includes a motion sensor as described above for motion sensor 112. In various embodiments, motion tracking subsystem 121 is configured to monitor motion of a subject relative to a motion axis and to generate an electronic motion signal based on the monitored motion. In various embodiments, including embodiments in which motion sensor 112 is provided in first portion 110, motion tracking subsystem 121 may receive motion data via electromechanical interconnect 114 in the form of electronic signals generated by motion sensor 112. In various embodiments, motion tracking subsystem 121 can be configured to monitor motion of a subject 100, and to generate an electronic motion signal based on the monitored motion. In various embodiments, motion tracking subsystem 121 provides an electronic signal input to location subsystem 122.

In various embodiments, second portion 120 of monitoring device 140, including location subsystem 122, can be deployed on a surface of subject 100 (e.g. a surface of a neck of a subject 100), or a surface of clothing worn by a subject 100, and may be utilized to monitor location of the subject 100. In various embodiments, location subsystem 122 includes a global navigation satellite system (e.g. GPS) receiver, another suitable location sensor, or combinations thereof. In various embodiments, location subsystem 122 includes a GPS receiver that is configured to use the global GPS network to determine global coordinates of a subject within a predetermined tolerance. In various embodiments, location subsystem 122 includes a plurality of interfaces to external electronics and/or external physical parameters such as, for example, a first interface to enable the supply of electricity to the sensor from power source subsystem 128 that is part of an electronic subsystem of second portion 120 of monitoring device 140, a second interface to electronics configured to receive and/or process high-frequency electronic signals directly from, for example, a satellite navigation system, an antenna, an electronic filter, a low-noise amplifier, or combinations thereof, and a third interface to coordinate transmission and/or reception of electronic signals such as a clock, data, etc., to and/or from processor 132. In various embodiments, location subsystem 122 may sense and/or process the geolocation of a subject 100. The inventors have observed that a GPS receiver consumes a large amount of power from power source subsystem 128. Thus, in various embodiments, location subsystem 122 can include a mechanism such as, for example, a timing circuit, to switch power to the GPS receiver on and off periodically to obtain a reference location of subject 100 for location subsystem 122. In various embodiments, location subsystem 122 includes a compass and receives motion data in the form of electronic signals generated by from motion tracking subsystem 121 or via electromechanical interconnect 114 in the form of electronic signals generated by motion sensor 112. In various embodiments, location subsystem 122 includes an integrated math engine configured to process electronic signals including reference location data received from a GPS receiver, electronic signals including motion data from motion tracking subsystem 121, and electronic signals including direction data from a compass. In various embodiments, location subsystem 122 can be configured to monitor location of a subject 100, and to generate an electronic location signal based on the monitored location.

In various embodiments, second portion 120 of monitoring device 140, including audio in/out subsystem 123, can be deployed on a surface of subject 100 (e.g. a surface of a neck of a subject 100), or a surface of clothing worn by a subject 100, and may be utilized to monitor sound around a surface of the subject 100. In various embodiments, audio in/out subsystem 123 includes one or more minimal footprint (e.g. 0.05-75 mm (length), 0.05-75 mm (width), 0.05-25 mm (height)) and low-power (e.g. 0.1-10 mW) integrated circuits including supporting electronics including, for example, a microphone, a speaker, or combinations thereof, designed, fabricated, and assembled on one or more layers of one or more flexible printed circuit and/or printed circuit board that constitutes part of an electronic subsystem of second portion 120. In various embodiments, such integrated circuits can include, for example, an electronic filter, an amplifier, an analog-to-digital converter, a digital-to-analog converter, and a processor configured to process electronic signals from one or more microphones and/or processors, and electronic signals transmitted to one or more speakers within the integrated circuit. In various embodiments, audio in/out subsystem 123 includes a plurality of interfaces to external electronics and/or external physical parameters such as, for example, a first interface to enable the supply of electricity to the subsystem from power source subsystem 128 that is part of an electronic subsystem of second portion 120 of monitoring device 140, a second interface to receive and/or process electronic signals from, for example, a microphone and/or a processor, a third interface to electronics configured to transmit and/or process electronic signals to be transmitted to one or more speakers, and a fourth interface to coordinate transmission and/or reception of electronic signals such as a clock, data, etc., to and/or from processor 132. In various embodiments, audio in/out subsystem 123 may capture, process, and/or transmit audio data such as user voice commands, alarm and/or status audio indicators, heart sounds, lung sounds, breathing sounds, sounds that indicate severe pain such as screams, other biological sounds, etc., from and/or to an ambient environment of the audio in/out subsystem. In various embodiments, audio in/out subsystem 123 can capture and/or process internal body sounds, and/or external sounds from subject 100.

In various embodiments, second portion 120 of monitoring device 140, including liquid (e.g. blood) sensor 127, can be deployed on a surface of subject 100 (e.g. a surface of a neck of a subject 100), or a surface of clothing worn by a subject 100, and may be utilized to detect liquid at and/or around a surface of the subject 100. In various embodiments, liquid sensor 127 includes one or more minimal footprint (e.g. 0.05-75 mm (length), 0.05-75 mm (width), 0.05-25 mm (height)) and low-power (e.g. 0.1-5 mW) integrated circuits including supporting electronics, designed, fabricated, and assembled on one or more layers of one or more flexible printed circuit and/or printed circuit board that constitutes part of an electronic subsystem of second portion 120. In various embodiments, such integrated circuits can include a liquid sensor such as a liquid leakage sensor (e.g. light emitter, light receptor, photodiode), a liquid sensor amplifier, analog and/or digital front-end circuitry, and/or a signal processor, configured to process electronic signals from liquid sensor elements within the integrated circuit. In various embodiments, liquid sensor 127 include a plurality of interfaces to external electronics and/or external physical parameters such as, for example, a first interface to enable the supply of electricity to the sensor from power source subsystem 128 that is part of an electronic subsystem of second portion 120 of monitoring device 140, a second interface to coordinate transmission and/or reception of electronic signals such as, for example, digital control signals, variable analog signals, etc., to and/or from, for example, light emitter, light receptor, photodiode, liquid sensor amplifier, that are internal to an integrated circuit and may be configured to emit light and/or receive light to detect the presence of a liquid, and a third interface to coordinate transmission and/or reception of electronic signals such as a clock, processed environmental signals data, etc., to and/or from processor 132. In various embodiments, liquid sensor 127 may be configured to sense, detect, and/or process environmental signals such as, for example, the presence of a liquid, and/or a liquid type, at and/or around a surface of the subject 100. In various embodiments, liquid sensor 127 can be configured to detect liquid at and/or around a surface of a subject 100, or the subject's clothing, and to generate an electronic liquid signal based on the detected liquid.

In various embodiments, second portion 120 of monitoring device 140 may include an indicator subsystem (not shown) and one or more indicators such as, for example, light emitting diodes (LEDs). In various embodiments, an indicator subsystem includes one or more minimal footprint (e.g. 0.05-75 mm (length), 0.05-75 mm (width), 0.05-25 mm (height)) and low-power (e.g. 0.1-5 mW) integrated circuits including supporting electronics such as, for example, LEDs, piezoelectric or other suitable vibrator, user input interfaces such as, for example, touch screen controllers, buttons, or switches, digital displays such as, for example, liquid crystal display (LCD), or organic light emitting diode (OLED) display, tactile sensors, haptic technology, or combinations thereof, designed, fabricated, and assembled on one or more layers of one or more flexible printed circuit and/or printed circuit board that constitutes part of an electronic subsystem of second portion 120. In various embodiments, such integrated circuits can include, for example, a digital-to-analog converter, an analog-to-digital converter, a control logic subsystem, power management subsystem, electronic signal drivers, or combinations thereof. In various embodiments, an indicator subsystem includes a plurality of interfaces to external electronics and/or external physical parameters such as, for example, a first interface to enable the supply of electricity to the subsystem from power source subsystem 128 that is part of an electronic subsystem of second portion 120 of monitoring device 140, a second interface to receive and/or process electronic signals from, for example, processor, a button, a switch, and/or a haptic sensor, a third interface to electronics configured to transmit and/or process electronic signals to be transmitted to, for example, one or more LEDs, digital displays such as, for example, LCD and/or OLED displays, and/or a vibrator, and a fourth interface to coordinate transmission and/or reception of electronic signals such as a clock, data, etc., to and/or from processor 132. In various embodiments, an indicator subsystem (not shown) may capture, process, and/or transmit capture and/or process inputs such as, for example, user commands, and to display and/or communicate status information such as, for example, remaining battery capacity and/or signal threshold crossings.

In various embodiments, second portion 120 of monitoring device 140 may include an radio-frequency identification (RFID) subsystem 126. In various embodiments, RFID subsystem 126 includes an RFID tag associated to a unique identification string for each monitoring device 140. In various embodiments, RFID subsystem 126 may broadcast its unique identification string for registration purposes with a mobile communication and display device (described in more detail below). In various embodiments, RFID subsystem 126 includes one or more minimal footprint (e.g. 0.05-75 mm (length), 0.05-75 mm (width), 0.05-25 mm (height)) and low-power (e.g. 0.1-5 mW) integrated circuits including supporting electronics such as, for example, antenna, power supply circuitry, or combinations thereof, designed, fabricated, and assembled on one or more layers of one or more flexible printed circuit and/or printed circuit board that constitutes part of an electronic subsystem of second portion 120. In various embodiments, such integrated circuits can include, for example, control logic subsystem, a power management subsystem, transmitter, and receiver circuitry, memory, or combinations thereof. In various embodiments, RFID subsystem 126 may be a passive implementation such that it obtains power wirelessly from radio waves received from an external RFID reader and/or near field communication (NFC) subsystem. In various embodiments, RFID subsystem 126 may be an active implementation such that it obtains power from a local power source. In various embodiments, RFID subsystem 126 includes a NFC intergrated circuit and a NFC antenna. In various embodiments, RFID subsystem 126 includes a RFID integrated circuit and a RFID antenna. In various embodiments, RFID subsystem 126 includes a plurality of interfaces to external electronics and/or external physical parameters such as, for example, a first interface to enable the supply of electricity to the subsystem from power source subsystem 128 that is part of an electronic subsystem of second portion 120 of monitoring device 140 and/or an external radio-frequency identification reader subsystem, a second interface to antenna and/or electronics configured to receive and/or transmit radio waves from and/or to an internal and/or external RFID and/or NFC subsystem, a third interface to coordinate transmission and/or reception of electronic signals such as a clock, data, etc., to and/or from processor 132. In various embodiments, RFID subsystem 126 may be configured to activate or wake up electronic subsystem of second portion 120. In various embodiments, RFID subsystem 126 may be configured to wirelessly relay stored information such as date of manufacture, model number, etc., between electronic subsystem 116 and an external radio-frequency identification reader or near-field communication subsystem. In various embodiments, RFID subsystem 126 can include a Quick Response (QR) code, or other suitable barcode, disposed, for example, on a surface of a housing of monitoring device 140. In various embodiments, the QR code, or other suitable barcode, may be configured to store information such as, for example, a date of manufacture of monitoring device 140 or second portion of monitoring device 140, model number of monitoring device 140 or second portion of monitoring device 140, that can be communicated to (e.g. wirelessly and/or optically read by) an external reader configured to read and process the QR code or other suitable barcode.

In various embodiments, second portion 120 of monitoring device 140 may include a biometric subsystem 124. In various embodiments, biometric subsystem 124 includes one or more biometric sensors such as, for example, a fingerprint sensor. In various embodiments, biometric subsystem 124 includes one or more minimal footprint (e.g. 0.05-75 mm (length), 0.05-75 mm (width), 0.05-25 mm (height)) and low-power (e.g. 0.1-5 mW) integrated circuits including supporting electronics designed, fabricated, and assembled on one or more layers of one or more flexible printed circuit and/or printed circuit board that constitutes part of an electronic subsystem of second portion 120. In various embodiments, such integrated circuits can include, for example, analog and/or digital front-end circuitry, memory, light emitter, light receptor, piezoelectric transducer, capacitor, and a signal processor configured to process electronic signals from light emitter, light receptor, piezoelectric transducer, and/or capacitor elements, within the integrated circuit, or combinations thereof. In various embodiments, biometric subsystem 124 includes a plurality of interfaces to external electronics and/or external physical parameters such as, for example, a first interface to enable the supply of electricity to the subsystem from power source subsystem 128 that is part of an electronic subsystem of second portion 120 of monitoring device 140, a second interface to structures of, for example, one or more light (e.g. infrared) emitters, photodiodes, light receptors, piezoelectric transducers, capacitors, that are internal to an integrated circuit and may be configured to emit light and/or receive light including biometric data, emit and/or receive acoustic energy including biometric data, from a finger of a subject 100, a third interface to electronics configured to receive and/or transmit electronic signals including biometric data (e.g. fingerprint data), from and/or to biometric subsystem 124 and external electronic subsystems of monitoring device 140 including, for example, processor 132 and memory 133, and a fourth interface to coordinate transmission and/or reception of electronic signals such as a clock, data, etc., to and/or from processor 132. In various embodiments, biometric subsystem 124 may be configured to sense and/or process light, acoustic energy, etc. including biometric data, for processing, storage, and/or transmission to a mobile communication and display device.

In various embodiments, second portion 120 of monitoring device 140 may include a power source subsystem 128. In various embodiments, power source subsystem 128 includes one or more minimal footprint (e.g. 1-20 mm diameter, 1-20 mm (length), 1-20 mm (width), 0.1-20 mm (height)) rechargeable and/or non-rechargeable, replaceable and/or non-replaceable batteries. In various embodiments, power source subsystem 128 includes one or more of such batteries and supporting electronics such as, for example, battery protection circuitry. Any suitable chemistry, shape, and form, of battery can be used such as, for example, lithium ion, lithium polymer, zinc air, coin cell, prismatic, bendable, or combinations thereof. In various embodiments, power source subsystem 128 includes a rechargeable lithium ion battery. In various embodiments, power source subsystem 128 includes a battery, a photovoltaic cell, energy harvesting subsystems utilizing physical properties such as, for example, thermal or piezoelectricity, a super-capacitor, or combinations thereof, and supporting electronics. Power source subsystem 128 may be directly or indirectly connected to the subsystems within the electronic subsystems of the monitoring device including electronic subsystems of the first portion 110 and second portion 120, to facilitate providing such subsystems with energy. In various embodiments, power source subsystem 128 includes a plurality of interfaces to external electronics and/or external physical parameters such as, for example, a first interface to enable the conversion of non-electrical energy into electrical energy, for example as implemented in a photovoltaic cell, a second interface to facilitate the dissemination of energy from the power source subsystem 128 to the subsystems within the electronic subsystems of the monitoring device including electronic subsystems of the first portion 110 and second portion 120. In various embodiments, power source subsystem 128 includes a removable battery. In various embodiments, power source subsystem 128 includes a non-removable battery.

In various embodiments, second portion 120 of monitoring device 140 may include a processor 132. In various embodiments, processor 132 includes one or more minimal footprint (e.g. 0.05-75 mm (length), 0.05-75 mm (width), 0.05-25 mm (height)) and low-power (e.g. 0.1-20 mW) integrated circuits and supporting electronics, for example, oscillator circuitry, designed, fabricated, and assembled on one or more flexible printed circuit and/or printed circuit board that constitutes part of an electronic subsystem of second portion 120. In various embodiments, such integrated circuits can include, for example, clock management subsystem, an energy management subsystem, a memory subsystem, an input and/or output port subsystem, a serial interface subsystem, a timer subsystem, an encryption subsystem, an amplifier, an analog signal processor, a digital signal processor, a floating point unit, a central processing unit (CPU), or combinations thereof. For example, processor 132 may include a micro-controller unit (MCU) with digital signal processing (DSP) functionality. In various embodiments, processor 132 includes a plurality of interfaces to external electronics and/or external physical parameters such as, for example, a first interface to enable the supply of electricity to processor 132 from power source subsystem 128 that is part of an electronic subsystem of second portion 120 of monitoring device 140, a second interface to coordinate one or more electronic signal links between processor 132 and one or more oscillators configured to influence the operational frequency of processor 132, a third interface to coordinate transmission and/or reception of electronic signals such as a clock, analog and/or digital data, between processor 132 and other subsystems within the electronic subsystems of the monitoring device including electronic subsystems of the first portion 110 and second portion 120 such as, for example, memory 133, communications interface 129, light emitter 115, light receptor 116, heart rate sensor 117, motion sensor 118, electrical potential sensor 111, respiratory rate sensor 113, temperature sensor 116, orientation sensor 118, motion tracking subsystem 121, the one or more environmental sensors 125, location subsystem 122, audio input/output subsystem 123, biometric subsystem 124, radio frequency identification (RFID) subsystem 126, liquid sensor 127. and a third interface to coordinate transmission and/or reception of electronic signals such as a clock, data, etc., to and/or from processor 132 and external electronic systems such as a personal computer (PC) and/or other mobile computing devices. In various embodiments, processor 132 may be programmed to acquire, aggregate, process, and/or transmit electronic signals from and/or to other subsystems within and/or external to electronic subsystems within second portion 120. In various embodiments, processor 132 may be programmed to implement a plurality of algorithms such as, for example, power optimization, physiological, environmental and/or other signal processing, real-time operating system, algorithms, or combinations thereof. In various embodiments, processor 132 may be programmed to coordinate local and/or external data storage in memory.

In various embodiments, second portion 120 of monitoring device 140 may include memory 133. In various embodiments, memory 133 includes one or more minimal footprint (e.g. 0.05-75 mm (length), 0.05-75 mm (width), 0.05-25 mm (height)) and low-power (e.g. 0.1-10 mW) integrated circuits and supporting electronics, designed, fabricated, and assembled on one or more flexible printed circuit and/or printed circuit board that constitutes part of an electronic subsystem of second portion 120. In various embodiments, such integrated circuits can include, for example, a control logic subsystem, electrical switches, electrical storage elements, high voltage generator, or combinations thereof. In various embodiments, memory 133 includes a plurality of interfaces to external electronics and/or external physical parameters such as, for example, a first interface to enable the supply of electricity to memory 133 from power source subsystem 128 that is part of an electronic subsystem of second portion 120 of monitoring device 140, a second interface to coordinate transmission and/or reception of electronic signals such as a clock, analog and/or digital data, between memory 133 and other subsystems within the electronic subsystems of the monitoring device including electronic subsystems of the first portion 110 and second portion 120 such as, for example, processor 132. In various embodiments, memory 133 may include a volatile and/or non-volatile random access memory (RAM) and/or read only memory (ROM) device configured to store information such as, for example, instructions, processed and/or raw data, or combinations thereof. In various embodiments, memory 133 may store processed biological and/or environmental signal data until a time when such data is transferred to other subsystems within and/or external to electronic subsystems within monitoring device 140 including subsystems within second portion 120.

In various embodiments, second portion 120 of monitoring device 140 may include a communications interface 129. In various embodiments, communications interface 129 includes one or more minimal footprint (e.g. 0.05-75 mm (length), 0.05-75 mm (width), 0.05-25 mm (height)) and low-power (e.g. 0.1-20 mW) integrated circuits and supporting electronics, such as, for example, an electronic filter, an antenna, or combinations thereof, designed, fabricated, and assembled on one or more flexible printed circuit and/or printed circuit board that constitutes part of an electronic subsystem of second portion 120. In various embodiments, communications interface 129 can include one or more wireless transceivers combined into a single integrated circuit. In various embodiments, communications interface 129 can include one or more wireless transmitters, and one or more wireless receivers, in respective, separate integrated circuits. In various embodiments, such integrated circuits include, for example a 802.11 subsystem, a Wi-Fi subsystem, a Bluetooth subsystem, a 3G/4G/5G cellular subsystem, a RF, VHF/UHF or other high frequency radio subsystem, a wireless USB subsystem, an electronic filter, a processor, a power management subsystem, an oscillator, or combinations thereof. In various embodiments, communications interface 129 includes a plurality of interfaces to external electronics and/or external physical parameters such as, for example, a first interface to enable the supply of electricity to memory 133 from power source subsystem 128 that is part of an electronic subsystem of second portion 120 of monitoring device 140, a second interface to one or more antenna and/or electronics configured to receive and/or transmit radio waves from and/or to an internal and/or external electronic subsystem of monitoring device 140, a third interface to coordinate the transmission and/or reception of electronic signals such as clock, data, etc., to and/or from processor 132 that is part of an electronic subsystem of second portion 120 of monitoring device 140, and a fourth interface to coordinate one or more electronic signal links between communications interface 129 and one or more oscillators configured to influence the operational frequency of communications interface 129. In various embodiments, communications interface 129 can be configured to wirelessly transfer raw and/or processed physiological, environmental, and/or system status data between an external electronic device and an electronic subsystem of monitoring device 140. In various embodiments, communications interface 129 can be configured to wirelessly upgrade programs and/or data embedded in an electronic subsystem of monitoring device 140.

In various embodiments, second portion 120 of monitoring device 140 may include a power source fuel gauge subsystem (not shown). In various embodiments, a power source fuel gauge subsystem includes one or more minimal footprint (e.g. 0.05-75 mm (length), 0.05-75 mm (width), 0.05-25 mm (height)) and low-power (e.g. 0.1-5 mW) integrated circuits including supporting electronics, designed, fabricated, and assembled on one or more flexible printed circuit and/or printed circuit board that constitutes part of an electronic subsystem of second portion 120. In various embodiments, such integrated circuits can include, for example, an analog-to-digital converter, memory, a central processing unit (CPU) configured to facilitate calculating battery discharge rate, remaining energy capacity, or combinations thereof. In various embodiments, a power source fuel gauge subsystem includes a plurality of interfaces to external electronics and/or external physical parameters such as, for example, a first interface to enable the supply of electricity to the subsystem from power source subsystem 128 that is part of an electronic subsystem of second portion 120 of monitoring device 140, and a second interface to coordinate transmission and/or reception of electronic signals such as a clock, data, etc., to and/or from processor 132. In various embodiments, a power source fuel gauge subsystem may be configured to process, for example, battery capacity, state-of-charge, battery voltage, or combinations thereof.

In various embodiments, second portion 120 of monitoring device 140 may include a power source charger subsystem (not shown). In various embodiments, a power source charger subsystem includes one or more minimal footprint (e.g. 0.05-75 mm (length), 0.05-75 mm (width), 0.05-25 mm (height)) and low-power (e.g. 0.1-5 mW) integrated circuits including supporting electronics, designed, fabricated, and assembled on one or more flexible printed circuit and/or printed circuit board that constitutes part of an electronic subsystem of second portion 120. In various embodiments, such integrated circuits can include, for example, a control logic subsystem, a short-circuit recovery subsystem, electronic switches, or combinations thereof. In various embodiments, a power source charger subsystem includes a plurality of interfaces to external electronics and/or external physical parameters such as, for example, a first interface to enable the wired or wireless supply of electricity from an external power source such as, for example, a Universal Serial Bus (USB) port, a main power adapter, a photovoltaic cell, a thermal or piezoelectric energy harvester, a wireless charging pad, a second interface to coordinate the transmission of electricity from the power source charger subsystem to the power source subsystem 128 that is part of an electronic subsystem of second portion 120 of monitoring device 140, and a third interface to coordinate transmission and/or reception of electronic signals such as a clock, data, etc., to and/or from processor 132. In various embodiments, power source charger subsystem may be configured to charge a rechargeable power source subsystem 128. In various embodiments, power source charger subsystem may be configured to independently or simultaneously supply power a rechargeable power source subsystem 128 and other subsystems within the electronic subsystems of the monitoring device including electronic subsystems of the first portion 110 and second portion 120.

In various embodiments, second portion 120 of monitoring device 140 may include a power distribution subsystem (not shown). In various embodiments, a power distribution subsystem includes one or more minimal footprint (e.g. 0.05-75 mm (length), 0.05-75 mm (width), 0.05-25 mm (height)) and low-power (e.g. 0.1-20 mW) integrated circuits and supporting electronics, designed, fabricated, and assembled on one or more flexible printed circuit and/or printed circuit board that constitutes part of an electronic subsystem of second portion 120. In various embodiments, such integrated circuits can include, for example, a linear regulator circuitry, a switching regulator circuitry, a voltage and/or current monitor circuitry, an analog-to-digital converter, a digital-to-analog converter, a voltage reference circuitry, or combinations thereof. In various embodiments, a power distribution subsystem includes one or more networks of specialized circuitry that may be configured to, for example, distribute appropriate voltage and/or current characteristics to appropriate subsystems, monitor voltage and/or current characteristics delivered to various subsystems, monitor and/or optimize power consumption and/or other related parameters of various subsystems, within the electronic subsystems of the monitoring device including electronic subsystems of the first portion 110 and second portion 120.

In various embodiments, second portion 120 of monitoring device 140 may include a computer port subsystem (not shown). In various embodiments, a computer port subsystem includes one or more minimal footprint (e.g. 0.05-75 mm (length), 0.05-75 mm (width), 0.05-25 mm (height)) and low-power (e.g. 0.1-10 mW) connectors, electronics and/or program interface, implemented in one or more subsystems of monitoring device 140, such as, for example, processor 132. In various embodiments, such connectors, electronics and/or program interface, are designed, fabricated and implemented on one or more flexible printed circuit and/or printed circuit board and/or cable assembly, that constitutes part of an electronic subsystem of monitoring device, including an electronic subsystem of second portion 120. In various embodiments, a computer port subsystem may include one or more ports configured to facilitate the transfer of electronic signals between electronic subsystems of monitoring device 140, and one or more external electronics such as, for example, an external power supply, an external mobile or non-mobile computing device, external bio-potential electrodes, for example, external bio-potential electrodes for EEG, ECG, EMG, measurements, a partial or complete capnometer, or combinations thereof. In various embodiments, a computer port subsystem may be configured to facilitate the transfer of electronic signals between electronic subsystems of monitoring device 140. In various embodiments, a computer port subsystem may include a port such as, for example, a universal serial bus (USB) port, or other suitable serial or parallel communication ports, configured to transfer power, clock, and data, etc. signals between electronic subsystems of monitoring device 140 to, for example, charge power source subsystem 128, transfer data into and/or out of processor 133. In various embodiments, a computer port subsystem may include one or more of such ports that are configured connect external EEG, ECG, EMG, or other suitable bio-potential electrodes, and/or other devices and/or electronics such as, for example, a capnometer, to electronic subsystems of monitoring device 140.

In various embodiments, electronic subsystems of first portion 110 and second portion 120 can be rearranged, repositioned, and/or further integrated into one or more compact designed housings configured to fit ergonomically, minimally-intrusively, and entirely on a surface area available on a human ear opposite the concha area or other alternative relevant body location suitable for sensing relevant physiological and/or environmental signals such as, for example, body/skin temperature, ambient temperature, blood oxygen saturation, altitude, humidity, UV index, pulse rate, ambient light, respiratory rate, blood pressure, motion, orientation, geolocation, audio, electrical potential, biometric, liquid (e.g. blood), other physiological signals, blood and/or end-tidal carbon dioxide content.

Figure 2:
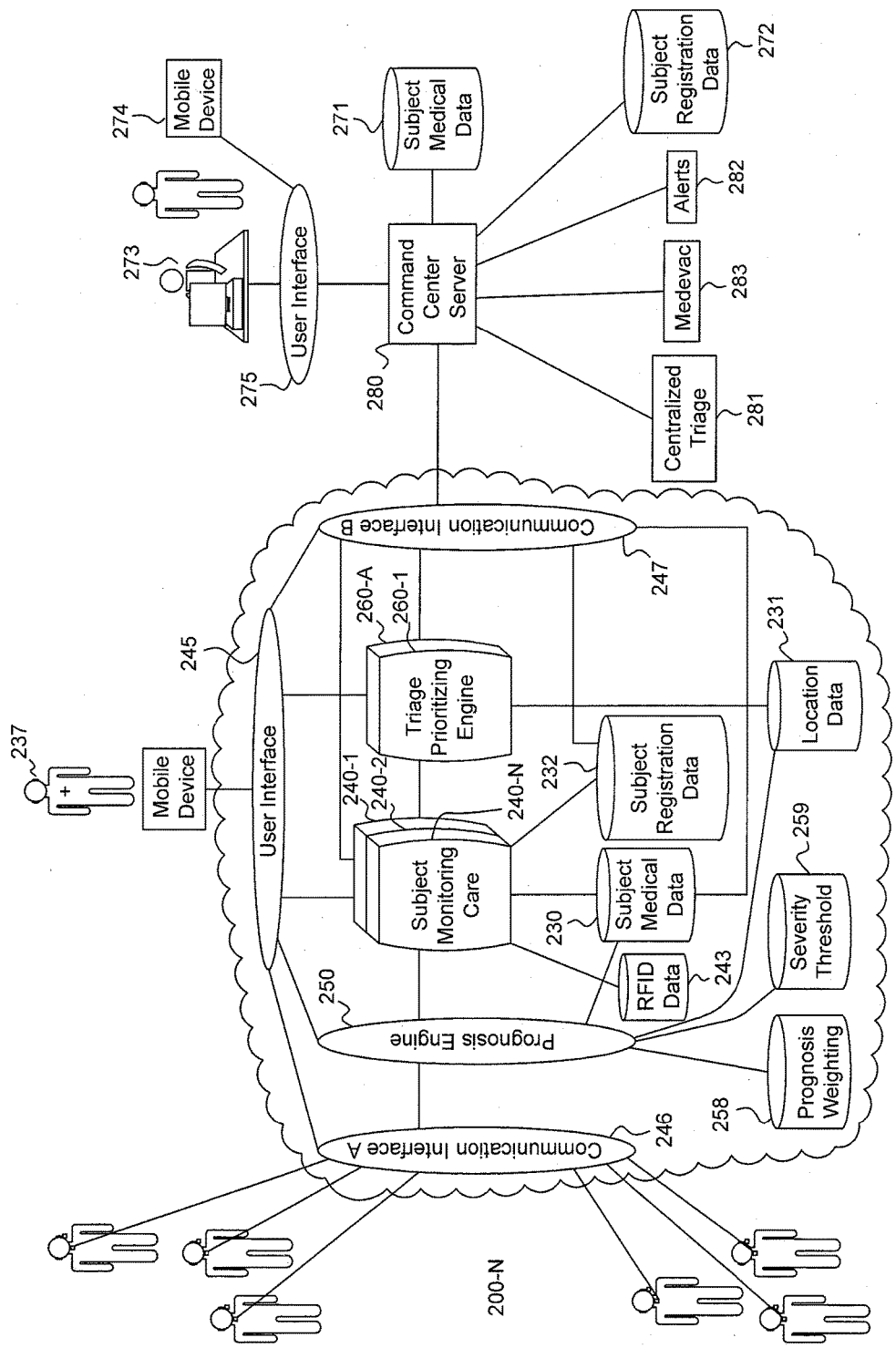
FIG. 2 is a block diagram of an example of a system for automated triage prioritization according to some embodiments.

Various embodiments of the present disclosure provide a networked environment as shown in FIG. 2 that includes a plurality of monitoring devices deployed on a plurality of subjects 200-N, one or more mobile communication and display devices in communication over a first network (e.g. a Bluetooth network) with the plurality of monitoring devices via communications interface A 246 and in communication with a central command center over a second network (e.g. a wireless network) via communications interface B 247. In various embodiments, mobile communication and display device 237 may include any suitable device such as, for example, a laptop, a personal computer, a smart phone, a smart watch, a personal digital assistant, a cellular phone, a tablet, an electronic personal planner, a slate tablet, a booklet computer, a convertible notebook, a phablet, a command and control system having a common operational picture (COP) or other situational awareness display, a human-wearable computing device, etc. In various embodiments, mobile communication and display device 237 operates an application (e.g. a software application, web application, native application, or mobile application) that is configured to display via user interface 245, a triage-prioritized list of one or more subjects' physiological signs by severity, subject descriptive data, subject and user (e.g. medic, EMT, first responder) geolocation data, monitoring device registration and binding to subject, alerts/messaging/notification features, and/or various customization options. In various embodiments, an application operating on mobile communication and display device 237 displays a record for each subject 200-N via user interface 245 and subject monitoring core 240-N, including, for example, identifying information for the subject 200-N, identifying information for the corresponding monitoring device (140), gender, age, medical records, photos, videos, descriptive data, geolocation, prognosis scores, triage prioritization order, and available physiological signs data. In various embodiments, one or more of the features of the central command center (e.g. command center server 280, subject medical data 271, subject registration data 272, etc.) may be accessed by the one or more mobile communication and display devices, and one or more computing devices (e.g. device 273, mobile device 274) of the central command center, over a cloud computing network. The one or more mobile communication and display devices 237 may include a mobile application or software application operating on the one or more mobile communication and display devices and including multiple blocks of logical software cores referred to as subject monitoring cores (denoted subject monitoring cores 250-1, 250-2, . . . , 250-N; these may be referred to collectively as "subject monitoring cores 250") and various software modules operating in a networked environment including a user interface 245, a prognosis engine module 250, triage prioritizing engine 260-A, that provide real-time, in-memory collection and analysis of generated and cached respective machine readable values corresponding to respective physiological parameters of subjects 200-N, respective environmental parameters around such subjects, respective physical parameters (e.g. location, orientation) of such subjects, respectively monitored in real-time by corresponding monitoring devices 140, to generate respective prognosis scores for each of the monitored subjects, and a triage prioritization order for the monitored subjects, based on complex algorithms, predetermined severity thresholds, predetermined prognosis weighting factors, and the generated machine readable values, the cached machine readable values, and to display, and/or change a display, of generated respective human readable values for a predetermined number of subjects on respective portions of user interface 245 based on the generated triage prioritization order.

In various embodiments, prognosis weighting factor module 258, and/or severity threshold module 259, receive, retrieve, and store in memory, respective prognosis weighting factors (e.g. pain index, predetermined sound type (e.g. scream) detection, blood or liquid detection, heart beat issues, breathing issues, greater than a predetermined percentage of confidence in prognosis (e.g. 95%, 90%, 75%), intelligence alerts, etc.), and/or respective severity thresholds (e.g. high and/or low thresholds for pulse oximetry, respiratory rate, heart rate, skin/body temperature, subject movement, monitoring device remaining battery capacity, distance between subject and user, a plurality of subject orientations, monitoring device signal strength, etc.). In various embodiments, prognosis weighting factors and/or severity thresholds are predetermined. In various embodiments, predetermined prognosis weighting factors and/or severity thresholds are dynamically updated based on, for example, inputs from a user (e.g. medic, EMT, physician, first responder) 237 accessing the system via user interface 245, inputs from a remote administrative or medical user (e.g. 273, 274) accessing the system via user interface 275 and communications interface B 247, environmental parameters detected and/or transmitted to the mobile communication from one or more monitoring devices, intelligence (e.g. HUMINT, SIGINT, ELINT, FMV, Automatic Identification System (AIS) inputs) alerts received by a mobile communication and display device via communications interface B 247 (e.g. from a command center server 280), subject medical data (e.g. 230, 271), etc. In various embodiments, a weather module (not shown) may receive real-time environmental parameters (e.g. ambient pressure, ambient temperature, humidity, UV index), and, for example, real-time location data, from a plurality of monitoring devices (140) deployed on a plurality of subjects 200-N, and provide real-time, accurate weather forecasting at locations specific to each of the plurality of subjects 200-N.

In various embodiments, RFID data module 243 receives, retrieves, and stores in memory, RFID data (or bar code, QR code, or other device identifying data) from one or more monitoring devices via communications interface A 246, via an RFID (or bar code, QR code, or other device identifier) reader of, or in serial communication with, mobile communications and display device. In various embodiments, location data module 231, receives, retrieves, and stores in memory, location data (e.g. GPS coordinates) of the mobile communication and display device, subject location data (e.g. GPS coordinates, compass heading and motion) received from one or more monitoring devices via communications interface A 246, and/or locations of nearby and local medical facilities, hospitals, bases, and any and all other pertinent geolocation values. In various embodiments, subject medical data module 230 receives, retrieves, and stores in memory, historical medical data (e.g. data in electronic medical records, data in medical history, prior physiological parameters, orientation, etc. received via communications interface A 246 from monitoring device(s) deployed, medical data received via communications interface B 247 such as from subject medical data 271, subject descriptive (e.g. photos, videos, age, gender, height, weight, hair, eye color, race, body type, body size, text-based visual description, and any known identifying features such as scars or tattoos) data received via communications interface B 247 (e.g. subject medical data 271), via a camera (e.g. photo, video) of, or in communication with (e.g. serial, over communications interface A 246), mobile communications and display device, and/or via user interface 245 regarding subject 200-N, and/or more subjects. In various embodiments, subject registration data module 232 receives, retrieves, and stores in memory, registration information binding respective monitoring devices (e.g. QR code, RFID, unique identification strings, bar code, pseudorandomly generated value, or other suitable unique identifying information) to respective subjects 200-N (e.g. subject name, social security number, date of birth, pseudorandomly generated value, or other suitable unique identifying information). In various embodiments, a pseudorandomly generated value is generated using, for example, a C RAND or RAND_S function, a PHP hypertext preprocessor function microtime or mt_rand, an Unix function/dev/random, a Java function SecureRandom, an Open SSL RAND_screen( ) function, or other suitable function, to return a pseudorandom sequence with a period long enough so that a finite sequence of reasonable length is not periodic and with an information entropy that is high enough to resist a brute force attack by a cryptanalyst. In various embodiments, a pseudorandomly generated value is generated using, for example, a secret key, or seed, to set the initial state of the pseudorandom sequence generator, a combination of the seed and, for example, a counter output, to provide an input to a hash function such as, for example, MD5 or SHA-1, to increase cryptographic security in the generated pseudorandom sequence.

Mobile communication and display device may also include a forensics module for recording, reporting, tuning, and playback of collected data (e.g. RFID Data 243, subject medical data 230, 271, location data 231, prognosis scores, triage prioritization orders, severity scores, etc.). In some embodiments, forensics module 160 can store recorded data in a non-transitory, tangible machine readable storage medium. The non-transitory, tangible storage medium can be a non-transitory computer readable storage medium. The computer readable medium can be a machine-readable storage device, a machine-readable storage medium, a memory device (e.g., flash or random access memory), a hard disk drive, a tape drive, an optical drive (such as, but not limited to CDROM, DVD, or BDROM) or the like, or a combination of one or more of them. In various embodiments, forensics module stores RFID Data 243, subject medical data 230, 271, location data 231, prognosis scores, triage prioritization orders, and/or severity scores, in persistent storage. In various embodiments, forensic module manages playback operations such that stored data is provided as an input to prognosis engine and/or triage prioritization engine to perform all or some of the functions described herein for data received from monitoring devices for subjects 200-N. In various embodiments, forensic module manages playback operations and permits users to speed up or slow down playback of the stored data. For example, forensic module can manage playback operations to permit a user to visually review 6 months of stored data via user interface 237, 275 in a significantly shorter period of time such as 6 hours or 60 minutes. In some embodiments, results based on using stored data provided by forensics module can be used to perform trend analysis, after-action reports, revise prognosis weighting, and/or severity thresholds for a respective subject, and/or revise or update a subject's medical history, such that the prognosis weighting factors, severity thresholds, and subject medical data (230, 271) can be further optimized. In some embodiments, a user can use data and trends provided by operations managed by forensics module to build up a knowledge base of information.

Although three subject monitoring cores, and two triage prioritizing engines, are shown in this example, any number of subject monitoring cores, and triage prioritizing engines, may be used. Operational personnel 237 (e.g., medics, EMTs, first responders, physicians) may access the prognosis engine 250, subject monitoring core 240-N, triage prioritizing engine 260-A, via the user interface 245. In various embodiments, operational personnel 237 can access other modules (e.g. forensics module (not shown), RFID data module 243, subject medical data module 230, subject registration data module 232, prognosis weighting factor module 258, severity threshold module 259, location data module 231, etc.) via the user interface 245.

Figure 3:
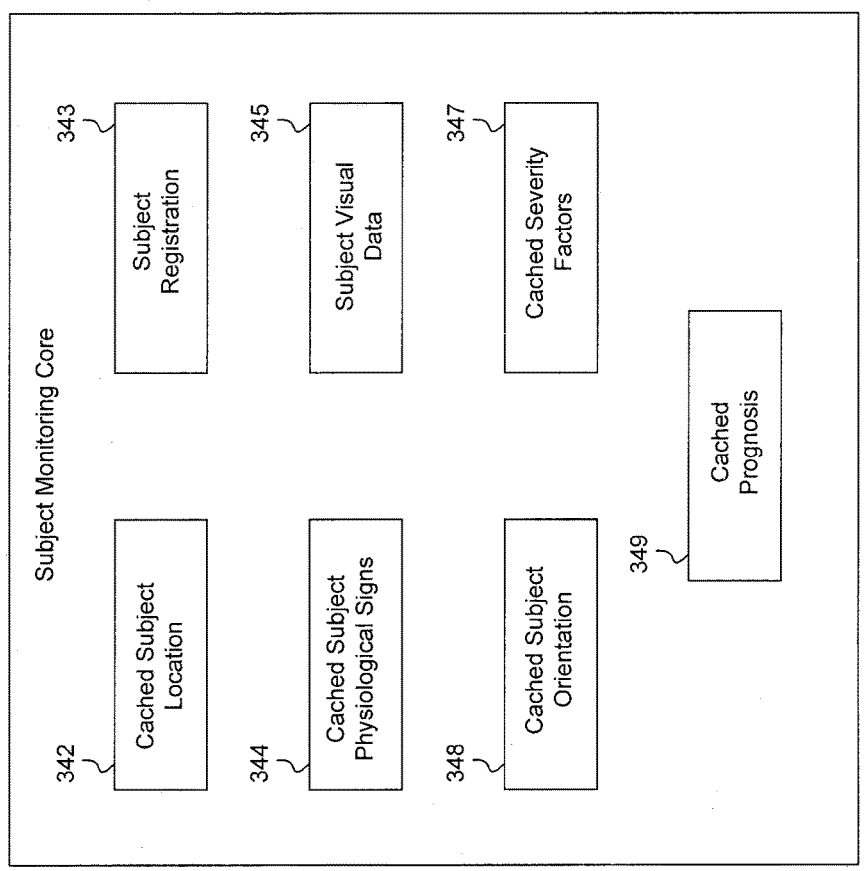
FIG. 3 is a block diagram of an example of a subject monitoring core of a mobile communication and display device in accordance with some embodiments of the present subject matter.

FIG. 3 shows an example of a subject monitoring core 250-N that includes location 342 of subject 200-N cached in memory of a mobile communication display device (e.g. RAM, in-memory data grids, retrieved from location data module 231, in-memory database (e.g. IMDB, MMDB, memory resident database, etc.)), physiological signs 344 for subject 200-N cached in memory of a mobile communication display device (e.g. RAM, in-memory data grids, retrieved from subject medical data module 230, in-memory database (e.g. IMDB, MMDB, memory resident database, etc.)), orientation 348 for subject 200-N cached in memory of a mobile communication display device (e.g. RAM, in-memory data grids, retrieved from orientation data module (not shown), in-memory database (e.g. IMDB, MMDB, memory resident database, etc.)), registration 343 for subject 200-N stored in memory of a mobile communication display device (e.g. RAM, ROM, in-memory data grids, retrieved from subject registration data module 232, NoSQL database, in-memory database (e.g. IMDB, MMDB, memory resident database, etc.)), visual data for subject 200-N stored in memory of a mobile communication display device (e.g. RAM, ROM, in-memory data grids, retrieved from subject medical data module 230, NoSQL database, in-memory database (e.g. IMDB, MMDB, memory resident database, etc.)), severity scores (e.g. pulse oximetry, respiratory rate, heart rate, skin/body temperature, movement, corresponding monitoring device remaining battery capacity, distance between subject and user, a plurality of subject orientations, corresponding monitoring device signal strength, etc., severity scores) for subject 200-N cached in memory of a mobile communication display device (e.g. RAM, in-memory data grids, retrieved from prognosis engine 250, in-memory database (e.g. IMDB, MMDB, memory resident database, etc.)), prognosis scores for subject 200-N cached in memory of a mobile communication display device (e.g. RAM, in-memory data grids, retrieved from prognosis engine 250, in-memory database (e.g. IMDB, MMDB, memory resident database, etc.)).

In various embodiments, a mobile communications and display device includes one or more network switches, and/or encryption switches, memory (e.g. active memory 822 (FIG. 8), which may include a persistent storage unit (e.g. NoSQL, MySQL cluster, database), a distributed working memory (e.g. software running on processor 820 (FIG. 8) and including a plurality of in-memory data grids such as, for example, a distributed R-tree index, Quadtree index, Rete diagram, Gna tree, Octree, Grid, Z-order, time-split B-tree, multi-version B-tree, etc., architecture in memory, in-memory database (e.g. IMDB, MMDB, memory resident database, etc.)), processor (e.g. 820 (FIG. 8)) running the distributed working memory software and communicating with user interface module 245 via an object-oriented data interchange format such as, for example, JavaScript Object Notation (JSON) and providing, for example, NoSQL, MySQL cluster, persistence. In various embodiments, processor (e.g. 820 (FIG. 8)) of mobile communication and display device stores instructions in a non-transient, tangible machine readable storage medium. The non-transient, tangible storage medium can be a non-transient computer readable storage medium. The computer readable medium can be a machine-readable storage device, a machine-readable storage medium, a memory device (e.g., flash or random access memory), a hard disk drive, a tape drive, an optical drive (such as, but not limited to CDROM, DVD, or BDROM) or the like, or a combination of one or more of them.

Referring again to FIG. 2, the user interface module 245 provides an interface between users 237 (e.g. medics, EMTs, physicians, first responders), the functionality of the mobile communication and display device, data received from the plurality of monitoring devices deployed on subjects 200-N via communications interface A 246 and over a first network (e.g. a Bluetooth network), and data received from a command center server 280 via communications interface B 247 and over a second network (e.g. a wireless network, the Internet, a cloud computing network (e.g. a public or secure cloud), etc.). In various embodiments, the user interface 245 is a representational state transfer (REST) application programming interface (API) based on a JSON model to provide access to many types of clients (e.g. thick and thin clients, mobile device clients). In various embodiments, user interface module 245 provides a Web-based interface (e.g. via a web-based application) to interface with command center server 280. In various embodiments, user interface 245 provides platform/device independent visualization. In various embodiments, user interface 245 provides portal services to many types of clients to interface with command center server 280. In various embodiments, user interface module 245 includes web services to interface with command center server 280. In various embodiments, user interface module 245 provides a command driven interface (e.g. DOS, Linux, etc. command driven interface) to interface with command center server 280. The user interface module 245 can include a portal to interface with command center server 280. In various embodiments, suitable secure communication techniques may be utilized to communicate data between over the first and/or second network such as, for example, secure communication methods employing asymmetric or symmetric encryption techniques, message authentication codes, secure hashing algorithms, or combinations thereof using, for example, a network security protocol such as, for example, SSL or TLS.

Referring now to FIG. 2, mobile communication and display device 237 includes communication interface A 246 communicating with monitoring devices deployed on subjects 200-N and communications interface B 247 communicating with one or more command center servers 280. Communications interface modules 246, 247 allow software and data to be transferred between monitoring devices deployed on subjects 200-N, one or more command center servers 280, various modules of mobile communication and display device 237, and/or external devices including, for example, devices associated with external sensors, external readers, and/or external assets (e.g. MEDEVAC, CASEVAC assets). In various embodiments, communications interface modules 246, 247 provide machine-to-machine (MTM) communications such as, for example, in an Internet of Things (IoT) infrastructure. In various embodiments, communications interface modules 246, 247 provide indications (e.g. notifications, communications, and/or signals) to external devices (e.g. via command center server 280, alerts 282, other mobile communications and display devices, etc.) based on specifications predefined for prognosis engine 250, triage prioritizing engine 260-A, subject monitoring core 240-N, Medevac 283, Alerts 282, etc., for a subject 200-N and when prognosis engine 250, triage prioritizing engine 260-A, subject monitoring core 240-N, provides an indication that an event has been identified and/or triggered. In various embodiments, such as, for example, for government and/or military applications, communications interface B 247 module may include a satellite or RF radio, such as, for example, military radios, including via a Single Channel Ground and Airborne Radio System (SINCGARS), and/or NASA MGRS-compliant communications. In various embodiments, such as, for example, for commercial applications, communications interface B 247 module may include a connection such as, for example, a Wi-Fi, Ethernet, analog phone, or digital leased line networking connection.

Examples of communications interface modules 246, 247 can include a modem, Ethernet card, wireless network card, a Personal Computer Memory Card International Association (PCMCIA) slot and card, or any suitable network interface module. Software and data transferred via communications interface communications interface modules 246, 247 can be in the form of signals, which can be electronic, electromagnetic, optical, or the like that are configured to being received by communications interface communications interface modules 246, 247. These various types of signals are collectively referred to herein as electronic signals. These electronic signals can be provided to communications interface modules 246, 247 via a communications path (e.g., channel), which can be implemented using wire, cable, fiber optics, a telephone line, a cellular link, a radio frequency (RF) link, a satellite link, a Bluetooth link, and other communication channels.

In various embodiments, a plurality of monitoring devices for a plurality of subjects 200-N can simultaneously connect wirelessly to mobile communication and display device 237 via communications interface A 246. In various embodiments, a secure (e.g. encrypted) wireless connection between a monitoring device and a mobile communication and display device 237, and/or relay network device (not shown), securely identifies the respective monitoring device to the mobile communication and display device 237, and/or relay network device (not shown). In various embodiments, the system including monitoring device and a mobile communication and display device 237, and/or relay network device (not shown), is configured to search for and change transmission frequencies on the monitoring device and a mobile communication and display device 237, and/or relay network device (not shown), due to interference or prohibitive/denied electromagnetic environment by using a randomized, but previously synchronized algorithm that defines a set of transmission frequencies to cycle through. In various embodiments, relay network device (not shown) can be used to receive and rebroadcast monitoring device transmissions to mobile communication and display device 237. In various embodiments, relay network device (not shown) may be, for example, a battery or externally powered mobile device that may receive monitoring device transmissions, cache them in memory, and then submit them to a configured application (e.g. a mobile application) for display on relay network device. In various embodiments, including a relay network device (not shown) in the system increases the range of the system to any environment where a network connection can be made via Wi-Fi, cellular connectivity, satellite connectivity, or any other IP or similar connectivity of relay network device (not shown). In various embodiments, relay network device (not shown) includes a mechanism such as, for example, via on-screen displays and/or lights, to signal the strength of other relay network devices (not shown) in a surrounding area of the relay network device (not shown) to enable comprehensive coverage for an installation. In various embodiments, a plurality of relay network nodes (not shown) may redundantly work in parallel, each caching a complete set of monitoring device data transmissions to be transmitted when either the addressed, appropriate mobile communication and display device 237 or a new, replacement mobile communication and display device 237 becomes available via the relay network. In various embodiments, a plurality of relay network nodes (not shown) includes a series of relay network devices (not shown) configured to authenticate with, and receive data from, a plurality of monitoring devices that may be centrally aggregated and presented for either global or localized views of subjects on an application (e.g. mobile application, native application) running on one or more mobile communication and display devices 237, and/or an application running on one or more remote computing devices (273, 274). In various embodiments, each monitoring device, and/or a separate external subject notification device deployed on the subject, communicated with mobile communication and display device directly, or indirectly via one or more relay network devices (not shown), and notifies the respective subject such as, for example, by vibrations, flashing lights, auditory sounds, etc., as to the status of communications between the monitoring device deployed on the subject and a mobile communication and display device 237.

In various embodiments, centralized triage 281 is a logical representation of a centralized triage station including one or more physicians/specialists, a hospital or second-level care facility, an ambulatory facility, or other suitable facility, where one or more subjects 200-N are transferred to via MEDEVAC, CASEVAC, or other suitable transportation services (e.g. ambulance), and where medical data, location data, registration data, orientation data, etc., regarding such subjects (e.g. stored in subject medical data module 230, subject registration data module 232, subject location data module 231, subject orientation data module 231, etc.) is transferred via communications interface B 247 and made accessible to users (e.g. 273, 274) at such facilities via user interface 275. In various embodiments, Medevac 281 is a logic representation of the logistics of ambulatory services (e.g. via MEDEVAC, CASEVAC, Ambulance, etc.) that the system may assign to various, disparate medical facilities based on, for example, their facilities and their current patient loads. Referring again to FIG. 2, the user interface module 245 provides an interface between users 237 (e.g. medics, EMTs, physicians, first responders), the functionality of the mobile communication and display device, data received from the plurality of monitoring devices deployed on subjects 200-N via communications interface A 246 and over a first network (e.g. a Bluetooth network), and data received from a command center server 280 via communications interface B 247 and over a second network (e.g. a wireless network, the Internet, a cloud computing network (e.g. a public or secure cloud), etc.). In various embodiments, the user interface 275 is a representational state transfer (REST) application programming interface (API) based on a JSON model to provide access to many types of clients (e.g. thick and thin clients, mobile device clients, desktop clients). In various embodiments, user interface module 275 provides a Web-based interface (e.g. via a web-based application) to interface with command center server 280. In various embodiments, user interface 275 provides platform/device independent visualization. In various embodiments, user interface 275 provides portal services to many types of clients to interface with command center server 280. In various embodiments, user interface module 275 includes web services to interface with command center server 280. In various embodiments, user interface module 275 provides a command driven interface (e.g. DOS, Linux, etc. command driven interface) to interface with command center server 280. The user interface module 275 can include a portal to interface with command center server 280. In various embodiments, centralized triage 281 provides a portal for a centralized triage group (e.g. one or more physicians/specialists) to enable users of the centralized triage group to review, override, or alert a user of a mobile communication and display device to evaluated changes in prognoses for subjects' monitored by monitoring devices communicating with the mobile communication and display device. In various embodiments, centralized medical personnel can interface with command center server 280 via user interface 275 to review subject data in real-time, annotate subjects' electronic records, edit subjects' medical information, add notes to subjects' medical records, annotate prognoses for subjects, send instructions and alerts to subjects' medics, EMTs, first responders at a respective mobile communication and display device, and/or initiate two-way communications via voice, text, video, e-mail, or any suitable communication technique, with patients' medics, EMTs, first responders at a respective mobile communication and display device.

In various embodiments, Alerts 282 is a logical representation of the notes, instructions, records, and delivery, notification and messaging features of the system. In various embodiments, an alert can be provided based on, for example, a prognosis score and/or triage prioritization order (e.g. alert provided to a user display via user interface 245, 275). In various embodiments, a notification message based on the prognosis score and/or triage prioritization order can be transmitted (e.g. to an external device via communications interface B module 247). Any suitable notification message can be provided and is based on a user's definitions provided for the prognosis or triage prioritization order. In some embodiments, the notification message is a default notification message set by, for example, the administrator 273, 274. For example, the notification message transmitted via communications interface module B 247 can be an electronic mail message, a telephone call, an alphanumeric page, a numeric page, a text message, a short messaging service message, a video message, a voice message, and other suitable notification messages. In various embodiments, a command center is a logical representation of functions provided by an administrative user. In various embodiments, command center server 280 provides an administrative and medical role portal into the system and may be integrated with operational command centers. In various embodiments, an administrative user may develop an operational environment for the system, review medic/EMT/first responder and subject data and geolocations in real-time, annotate medics' and subjects' electronic records, edit subjects' medical information, add notes to subjects' medical records, send instructions and alerts to subjects' medics, and initiate two-way communications via voice, text, video, email, or any suitable communication technique with subjects' medics, via user interface 275. For example, during combat operations, command center server 280 (Medevac 283), and administrative and/or medical role personnel interfacing with such server, can provide instructions to direct subjects to one of a plurality of operating posts with medical facilities depending on bed space, capabilities, and personnel. For example, during situations such as, for example, a natural disaster or mass casualty event, command center server 280 (Alerts 282), and administrative and/or medical role personnel interfacing with such server, may receive real-time notifications with respective prognosis scores and triage prioritization of various subjects, and may monitor and/or transmit instructions to direct/monitor the subjects' movement from the point of injury to the next level of care.

In various embodiments, command center server 280 and subject medical data 271 module may include a centralized data storage and system administration system. In various embodiments, subject medical data 271 module may include a secure subject data service 220 (not shown), such as, for example, a networked data provider for securely providing subject data such as, for example, subjects' medical and descriptive data accessed based on identifiable data of the subject, and other data such as, for example, locations of medical facilities, hospitals, bases, and any and all other pertinent geolocation values. In various embodiments, subject medical data 271 module may include one or more outside secure data providers, either in place of, or in addition to, a secure subject data service (not shown). In various embodiments, subject medical data 271 module may be a memory buffer of subject medical data that can be accessed via a secure subject data service including descriptive data, and medical data and via command center server 280 and user interface 275, 245. Command center server may include one or more servers 280 (e.g., Linux, windows, blade servers), a distributed working memory (e.g. software running on server), one or more network switches and/or encryption switches, a persistent storage unit (e.g. NoSQL, MySQL cluster, database). In various embodiments, command center server 280 may communicate with user interface module 275 via an object-oriented data interchange format such as, for example, JavaScript Object Notation (JSON) and provide, for example, NoSQL, or MySQL cluster, persistence. In various embodiments, command center server 280, subject medical data 271 module, and subject registration data 272 module, may include and provide suitable industry security and web services to facilitate data population and receipt. In various embodiments, subject medical data 271 module may include a transactional data warehouse, with analytical and operational data marts (now shown). In various embodiments, user interface 275 may provide a system administration portal for system administrative users and analyst users to perform maintenance and troubleshooting on the system. In various embodiments, command center server 280 provides a secure, high-speed connection between user interface 275, modules of mobile communication and display device 237 via communications interface B 247 module, subject medical data 271 module, and/or subject registration data 272 module.

In various embodiments, the prognosis engine 250 generates real-time prognosis scores for each of a plurality of subjects using generated machine readable values for each of a plurality of physiological, physical, and/or environmental parameters, and one or more prognosis weighting factors (from prognosis weighting modules 258). In various embodiments, the prognosis engine generates real-time respective severity scores for each of a plurality of physiological, physical, and/or environmental parameters, for each of a plurality of subjects using generated machine readable values for such parameters and a plurality of severity thresholds (from severity threshold module 259). In various embodiments, prognosis engine 250 interfaces with communications interface A module 246, prognosis weighting module 258, severity threshold module 259, subject monitoring core 240-N, subject medical data module 230, and/or user interface 245. In various embodiments, the triage prioritization engine 260-A selects a triage prioritization order of the subjects, including subjects in A monitoring groups, using the generated prognosis scores from prognosis engine 250. In various embodiments, the triage prioritization engine 260-A interfaces with prognosis engine 250, subject monitoring core 240-N, location data module 231, communications interface B module 247, and/or user interface 245.

Figure 4:
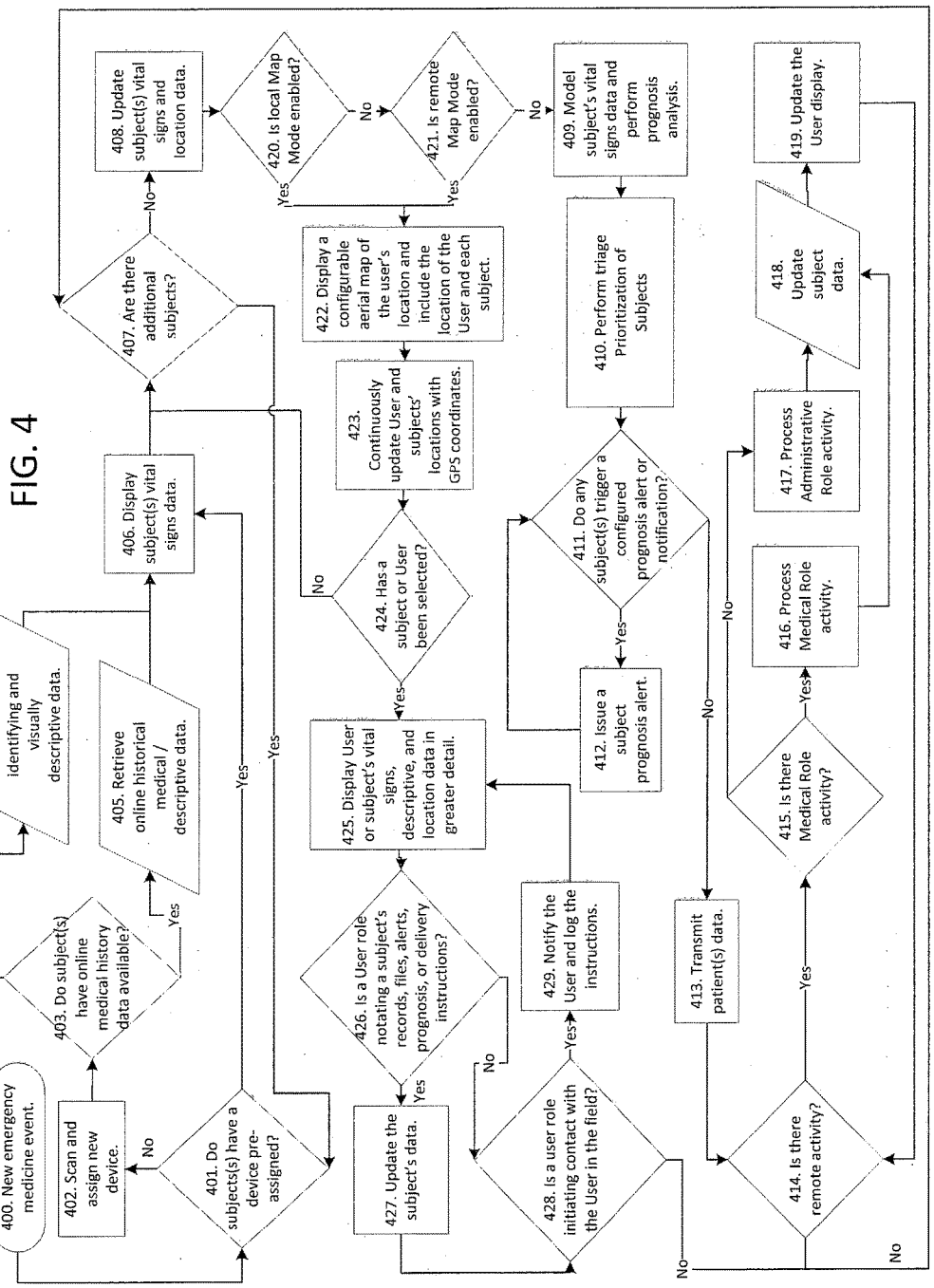
FIG. 4 is a flow chart illustrating a computer-implemented method of automated triage prioritization according to some embodiments.

FIG. 4 is a flow chart illustrating a computer-implemented method of automated triage prioritization according to some embodiments. At block 400, an emergency medical event with casualties to a plurality of subjects occurs in accordance with some embodiments. At block 401, a first subject has a monitoring device (140) applied to a surface of his/her body, and a subject monitoring core of a mobile communication display device determines if the subject has been pre-assigned (e.g. pre-registered) to the applied monitoring device (140). In various embodiments, if the subject has not been pre-assigned the monitoring device (140), at block 402, a user (e.g. medic, first responder, EMT) may scan the monitoring device (140) on the mobile communication display device to read the monitoring device's (140) RFID (or barcode, or QR code) to obtain the monitoring device's unique identification string. In various embodiments, at block 402, a monitoring device may automatically transmit it's respective RFID (or barcode, or QR code) to the mobile communication display device once the monitoring device has been removed from any packaging and/or activated by a user. The subject monitoring core of the mobile communication display device then assigns (e.g. registers in in data repository 232) this monitoring device to this subject. At block 403, the subject monitoring core of the mobile communication display device queries online medical data repositories (e.g. subject medical data repository 271) via communications interface 247 (e.g. over a wireless network, the Internet, a cloud computing network), and/or subject medical data repositories (230) stored thereon, to determine if the subject's electronic medical record is available to be retrieved by mobile communications and display device. If the subject's electronic medical record is not available to the mobile communications and display device, at block 404, the user may enter identifying and visually descriptive data to identify this subject which can be stored in memory of the mobile communication display device (e.g. 230, 232). If the subject's electronic medical record is available online (e.g. 271), or in a data repository of the mobile communication and display device (e.g. 230), at block 405, the subject monitoring core of the mobile communication display device retrieves this subject's electronic medical and descriptive data.

In various embodiments, once a monitoring device is deployed on a surface of a subject (e.g. on a surface of an ear opposite a concha of a subject), a transmitter of the monitoring device transmits electronic signals including the subject's physiological data, environmental data, and/or location, orientation, motion, etc. data, to a receiver of the mobile communications and display device. At block 404, 405, or if the subject had a pre-assigned monitoring device (140) at block 401, the registered subjects' physiological signs data is displayed on a display of the mobile communication display device via user interface 245. At block 407, the subject monitoring core of the mobile communication display device validates the existence of additional subjects to be registered to monitoring devices (140). If there are additional subjects to register, the method returns to block 401. If there are no additional subjects to register, at block 408, prognosis engine 250, triage prioritizing engine 260-A, and/or subject monitoring core 240-N, updates the registered subjects' physiological signs data from respective electronic signals received via wireless communications of the corresponding monitoring devices (140). At block 420, program code executable by a processor of the mobile communication display device, and encoded on a non-transient machine readable storage medium of the mobile communication display device, determines if the user local to the mobile communication display device (e.g. 237) has enabled a Map Mode on the mobile communication display device (e.g. 237) which is configured to display, for example, a configurable aerial map of the user and subjects' monitoring devices reporting their locations on a display of the mobile communication display device (e.g. 237). At block 421, program code executable by a processor of the command center server and/or by a processor of a remote computer, and encoded on a non-transient machine readable storage medium of the command center server or remote computer, determines if a remote administrative user or medical user (e.g. 273, 274) has enabled a Map Mode on a display of a remote computer (e.g. 273, 274) which is configured to display, for example, a configurable aerial map of the user and subjects' monitoring devices reporting their locations on a display of the remote computer (e.g. 273, 274). At block 422, the mobile communication display device, and/or remote computer, displays the Map Mode for the current user.

At block 423, subject monitoring core 240-N of the mobile communication display device updates the user's location data based on the location information (e.g. GPS coordinates) provided by the mobile communication display device and the subjects' location data based on the location information (e.g. GPS coordinates) provided by their monitoring devices (140) from respective electronic signals received via network communications (e.g. Bluetooth network) of the corresponding monitoring devices (140). At block 424, program code executable by a processor of the mobile communication display device, and/or program code executable by a processor of command center server 280 or a remote computer (e.g. 273, 274), determines if a user or subject has been selected on the user interface 245 of the mobile communication display device, and/or a user interface 275 of a remote computer (e.g. 273, 274), in the Map Mode. If not, the method returns to block 422 and updates the user and the subjects' locations on the map. If a user or subject has been selected on the user interface 245 of the mobile communication display device, and/or a user interface 275 of a remote computer (e.g. 273, 274), in Map Mode, at block 425, a display of the mobile communication display device, and/or a display of a remote computer (e.g. 273, 274), displays, for example, additional physiological signs, medical records, descriptive, administrative, alerts, notifications, instructions, location details, and other available and suitable data for the clicked selected user and/or subject. Users local to the mobile communication display device, and/or remote administrative users or medical users (e.g. 273, 274), may then choose to add notes on the user or subject's medical records, add files, communicate with the user, or other users, modify a prognosis for the subject, modify delivery instructions, add alerts, or perform other suitable actions, at block 426. At block 427, program code executable by a processor of the mobile communication display device, and/or program code executable by a processor of a remote computer, performs the actions selected by the user. If such users do not perform one or more functions at block 426, such user may give instructions or orders with alerts at block 428. If such users choose to give instructions or orders with alerts at block 428, program code executable by a processor of the mobile communication display device, and/or program code executable by a processor of a remote computer, gives instructions or orders with alerts selected by the user at block 429. The method then returns to block 422 to update the user and subjects' locations on the map displayed on a display of the mobile communication display device, and/or displayed on a display of a remote computer.

At block 409, each subject's physiological signs data, environmental parameters data, location, orientation, motion, etc. data, and/or other suitable subject data, communicated to the mobile communication display device via communications interface A (246), is data modeled, statistically analyzed, and/or predictively modeled, to generate prognosis scores by prognosis engine 250 of the mobile communication display device. At block 410, triage prioritizing engine 260-A generates a triage prioritization order of the subjects based on prognosis scores generated by prognosis engine 250 of the mobile communication display device at block 409. If block 409 or block 410 results in an alert condition, at block 411, program code executable by a processor of the mobile communication display device generates a suitable alert, and, at block 412, program code executable by a processor of the mobile communication display device displays, and/or communicates, the generated alert to the user via user interface 245, or an appropriate user (e.g. administrative role, or medical role) via user interface 275, depending on the conditions of the generated alert. If there are additional alerts to be handled by the mobile communication display device, block 411 repeats. If there are no additional alerts to be handled by the mobile communication display device, each subject's physiological signs data, environmental parameters data, location, orientation, motion, etc. data, and/or other suitable subject data received by the mobile communication display device, is stored in a data repository of the mobile communication display device, and/or transmitted to a centralized data repository (e.g. 271) at block 413. At block 414, program code executable by a processor of a command center server (e.g. 280), and/or by a processor of a remote computer/computing device (e.g. 273, 274) validates if remote activity is being performed by one or more users (e.g. 273, 274). If command center server (e.g. 280), and/or remote computer (e.g. 273, 274), validates remote activity, at block 415, program code executable by a processor of the command center server, and/or by a processor of remote computer (e.g. 273, 274), validates if the remote activity is from a medical or administrative role. If command center server (e.g. 280), and/or remote computer (e.g. 273, 274), validates the remote activity is from a medical role, at block 416, program code executable by a processor of the command center server, and/or by a processor of a remote computer (e.g. 273, 274), processes this activity. If command center server (e.g. 280), and/or remote computer (e.g. 273, 274), validates the remote activity is from an administrative role, at block 417, program code executable by a processor of the command center server, and/or by a processor of a remote computer, processes this activity. At blocks 416 and 417, program code executable by a processor of the command center server, and/or by a processor of a remote computer, updates respective subject data at block 418. At block 419, program code executable by a processor of the command center server, and/or by a processor of a remote computer, updates the subjects' data with the most up-to-date data, and a display of a remote computing device (e.g. 273, 274) displays the data to the user. The method returns to block 414 where program code executable by a processor of the command center server, and/or by a processor of a remote computer, validates additional remote activity. If the program code executable by a processor of the command center server, and/or by a processor of a remote computer, determined there is no remote activity at block 414, then the method returns to block 407 to determine if there are additional subjects to be registered with corresponding monitoring devices 140.

Figure 5A:
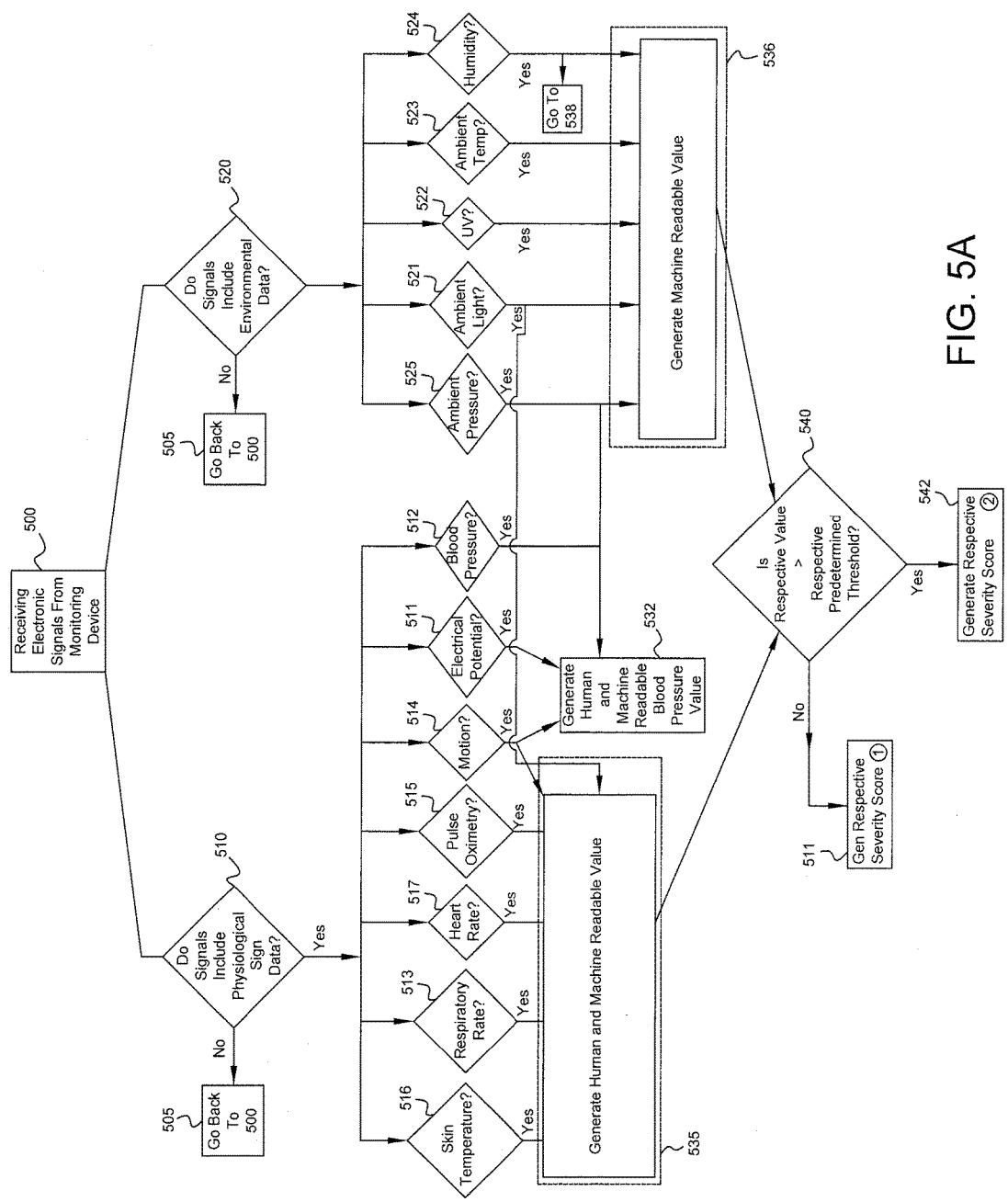
FIGS. 5A-5C are flow charts illustrating examples of a computer-implemented method of automated triage prioritization according to some embodiments of the present disclosure.
Figure 5B:
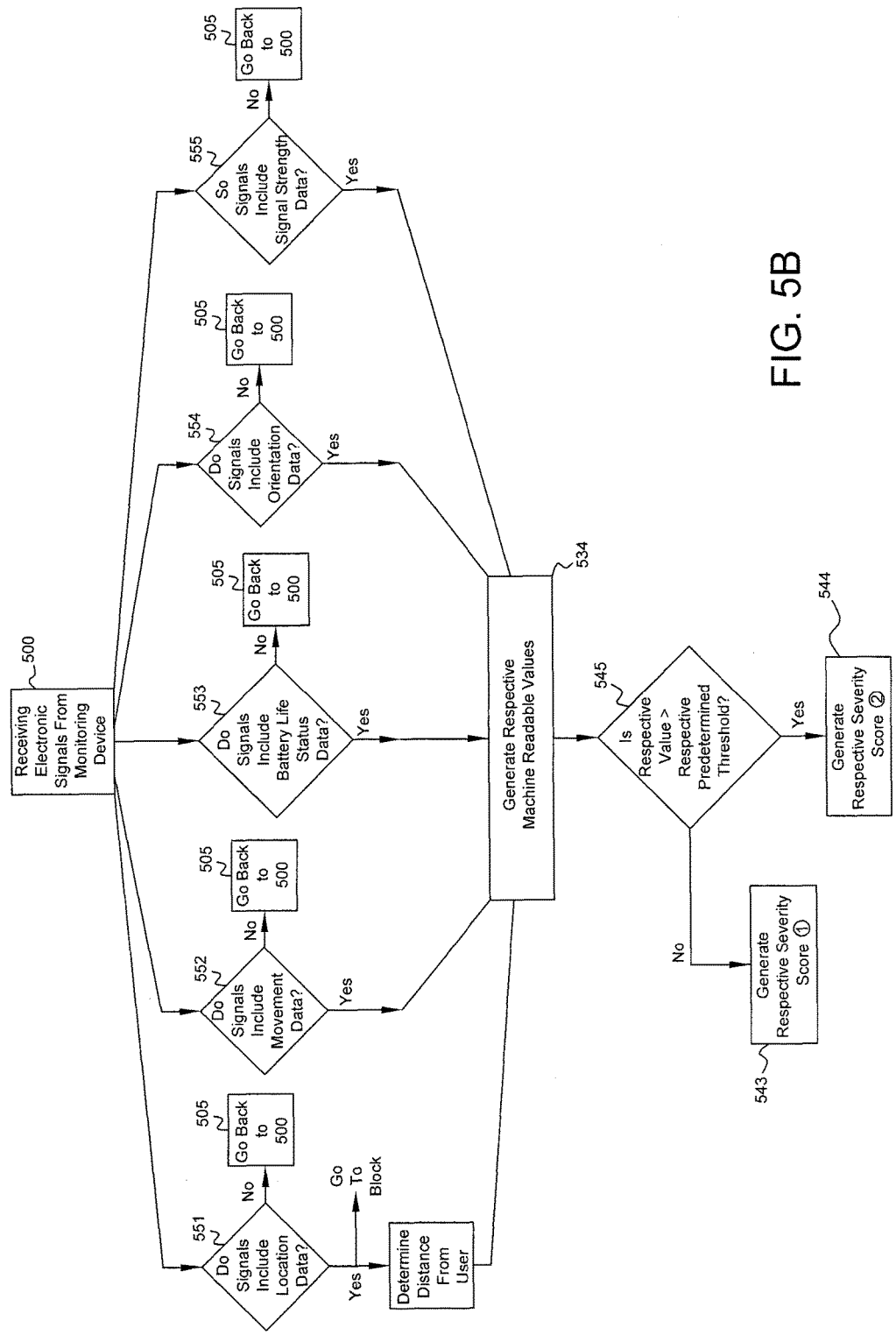
Figure 5C:
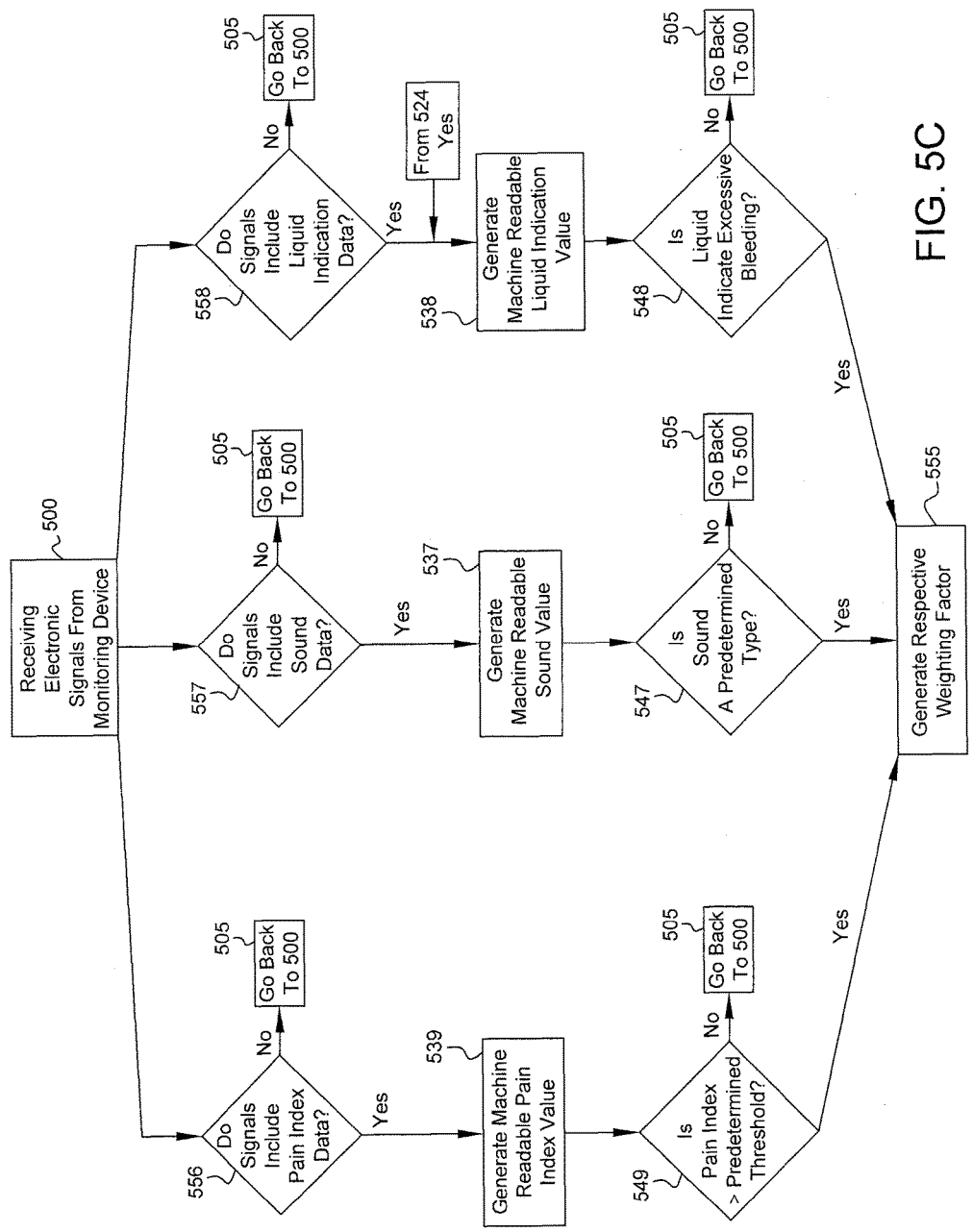

Referring now to FIGS. 5A-5C, computer-implemented methods of automated triage prioritization are provided. In some embodiments, a plurality of monitoring devices are provided where each monitoring device includes a first portion and a second portion. In some embodiments, each first portion of each monitoring device is configured for deployment on a surface opposite a concha of a respective ear of a respective subject. In some embodiments, each first portion of each monitoring device includes a plurality of physiological sensors. For example, the plurality of physiological sensors may include a pulse oximetry sensor including an emitter configured to emit light in a direction toward the concha and a receptor configured to receive light reflected from one or more sources in the direction where the pulse oximetry sensor is configured to generate an electronic pulse oximetry signal based on the received, reflected light. The plurality of physiological sensors may also include a blood pressure sensor comprising an electrocardiograph sensor configured to monitor an electrical potential at the ear surface, and a motion sensor configured to monitor motion at the ear surface relevant to a motion axis. In some embodiments, the blood pressure sensor is configured to generate an electronic blood pressure signal based on the monitored electrical potential and motion. Other suitable physiological sensors may be included in first portion of a monitoring device 140.

In some embodiments, each first portion of each monitoring device also includes an orientation sensor configured to monitor an orientation of the respective subject relative to an orientation axis and to generate an electronic orientation signal based on the monitored orientation. In various embodiments, each second portion of each monitoring device includes one or more atmospheric sensors including a pressure sensor configured to monitor ambient pressure around a surface of the respective subject and to generate an electronic ambient pressure signal based on the monitored pressure. In some embodiments, the one or more atmospheric sensors includes at least one of an ambient temperature sensor, a humidity sensor, a UV index sensor, and an ambient light sensor, such that each of the one or more atmospheric sensors is configured to monitor a corresponding environmental parameter around the surface of the respective subject and to generate a corresponding electronic signal based on the monitored environmental parameter.

In various embodiments, each second portion of each monitoring device is configured for deployment on another surface of a respective subject and the first portion of the monitoring device is configured to transmit the first portion generated electronic signals to the second portion. In various embodiments, each monitoring device 140 also includes a transmitter configured to transmit the generated electronic signals over a first network such as, for example, a Bluetooth network (e.g. a Bluetooth Low Energy (LE) smart network). In some embodiments, the first portion of the monitoring device is configured to transmit the first portion generated electronic signals to the second portion over a wired connection. At block 500, electronic signals from one or more of the plurality of monitoring devices 140 are received by a mobile communication and display device 237. In various embodiments, the mobile communication and display device 237 includes a communications interface A module 246 configured to be coupled to the first network and to receive the transmitted electronic signals over the first network from each of the transmitters of each of the plurality of monitoring devices, a user interface 246, a processor coupled to the communications interface, and a non-transient machine-readable storage medium encoded with program code executable by the processor. At block 510, a determination is made as to whether the signals include physiological data. If the received electronic signals do not include physiological data, at block 505, the method returns to block 500. If the received electronic signals include physiological data, at block 512-517, a determination is made as to the type of physiological data in the received electronic signals.

At block 516, if the received electronic signals for a subject include skin temperature data for the subject, program code executable by the processor will generate respective human and machine readable values indicative of skin temperature for the respective subjects using the received electronic signals at block 535. At block 513, if the received electronic signals for a subject include respiratory rate data for the subject, program code executable by the processor will generate respective human and machine readable values indicative of respiratory rate for the respective subjects using the received electronic signals at block 535. At block 517, if the received electronic signals for a subject include heart rate data for the subject, program code executable by the processor will generate respective human and machine readable values indicative of heart rate for the respective subjects using the received electronic signals at block 535. At block 515, if the received electronic signals for a subject include pulse oximetry data for the subject, program code executable by the processor will generate respective human and machine readable values indicative of pulse oximetry for the respective subjects using the received electronic signals at block 535. At block 512, if the received electronic signals for a subject include blood pressure data for the subject, program code executable by the processor will generate respective human and machine readable values indicative of blood pressure for the respective subjects using the received electronic signals at block 535. At blocks 514 and 511, if the received electronic signals for a subject include motion data and electrical potential data for the subject, program code executable by the processor will generate respective human and machine readable values indicative of blood pressure for the respective subjects using the received electronic signals at block 532.

At block 520, a determination is made as to whether the signals include environmental data. If the received electronic signals do not include environmental data, at block 505, the method returns to block 500. If the received electronic signals include environmental data, at block 521-525, a determination is made as to the type of environmental data in the received electronic signals. At block 525, if the received electronic signals for an environment around a subject include ambient pressure data for the environment, program code executable by the processor will generate respective machine readable values indicative of ambient pressure for the respective subjects using the received electronic signals at block 536. At block 521, if the received electronic signals for an environment around a subject include ambient light data for the environment, program code executable by the processor will generate respective machine readable values indicative of ambient light for the respective subjects using the received electronic signals at block 536, and provide another input to, for example, generate respective machine readable values indicative of pulse oximetry for the respective subjects at block 535. At block 522, if the received electronic signals for an environment around a subject include UV index data for the environment, program code executable by the processor will generate respective machine readable values indicative of UV index for the respective subjects using the received electronic signals at block 536. At block 523, if the received electronic signals for an environment around a subject include ambient temperature data for the environment, program code executable by the processor will generate respective machine readable values indicative of ambient temperature for the respective subjects using the received electronic signals at block 536, and/or provide another input to, for example, generate respective machine readable values indicative of body/skin temperature for the respective subjects at block 535. At block 524, if the received electronic signals for an environment around a subject include humidity data for the environment, program code executable by the processor will generate respective machine readable values indicative of humidity for the respective subjects using the received electronic signals at block 536, and/or provide another input to, for example, generate respective machine readable values indicative of liquid indication value for the respective subjects at block 538.

Referring now to FIG. 5B, at block 551, a determination is made as to whether the signals include respective location data for the subjects. If the received electronic signals do not include location data, at block 505, the method returns to block 500. At block 525, if the received electronic signals include respective location data for a subject, program code executable by the processor will determine a distance between the respective subject and the user of the mobile communication and display device, and generate respective machine readable values indicative of location for the respective subject using the received electronic signals at block 534. At block 552, a determination is made as to whether the signals include respective movement data for the subjects. If the received electronic signals do not include movement data, at block 505, the method returns to block 500. At block 552, if the received electronic signals include respective movement data for a subject, program code executable by the processor will generate respective machine readable values indicative of movement for the subject using the received electronic signals at block 534. At block 553, a determination is made as to whether the signals include respective battery life status data for each of the monitoring devices. If the received electronic signals do not include battery life status data, at block 505, the method returns to block 500. At block 553, if the received electronic signals include respective battery life status data for a monitoring device, program code executable by the processor will generate respective machine readable values indicative of battery life status data for the corresponding subject using the received electronic signals at block 534. At block 554, a determination is made as to whether the signals include respective orientation data for each of the subjects. If the received electronic signals do not include orientation data, at block 505, the method returns to block 500. At block 554, if the received electronic signals include respective orientation data for a subject, program code executable by the processor will generate respective machine readable values indicative of orientation for the subject using the received electronic signals at block 534. At block 555, a determination is made as to whether the signals include respective signal strength data for each of the monitoring devices. If the received electronic signals do not include signal strength data, at block 505, the method returns to block 500. At block 555, if the received electronic signals include respective signal strength data for a monitoring device, program code executable by the processor will generate respective machine readable values indicative of signal strength data for the corresponding subject using the received electronic signals at block 534.

Referring now to FIG. 5C, at block 556, a determination is made as to whether the signals include respective pain index data for each of the subjects. If the received electronic signals do not include pain index data, at block 505, the method returns to block 500. At block 559, if the received electronic signals include respective pain index data for a subject, program code executable by the processor will generate respective machine readable values indicative of pain index data for the subject using the received electronic signals at block 539. At block 557, a determination is made as to whether the signals include respective sound data for each of the subjects. If the received electronic signals do not include sound data, at block 505, the method returns to block 500. At block 557, if the received electronic signals include respective sound data for a subject, program code executable by the processor will generate respective machine readable values indicative of sound data for the subject using the received electronic signals at block 537. At block 558, a determination is made as to whether the signals include respective liquid indication data for each of the subjects. If the received electronic signals do not include liquid indication data, at block 505, the method returns to block 500. At block 558, if the received electronic signals include respective liquid indication data for a subject, program code executable by the processor will generate respective machine readable values indicative of liquid indication data for the subject using the received electronic signals, any received input of received electronic signals indicative of humidity data, at block 538.

Referring back to FIG. 5A, at block 540, prognosis engine 250 determines whether the respectively generated machine readable values indicative of the physiological and environmental parameters are greater than respective predetermined severity thresholds (e.g. in severity threshold 259) for the physiological and environmental parameters. At block 511, if a respectively generated machine readable value indicative of a physiological or environmental parameter is less than a respective predetermined severity threshold (e.g. in severity threshold 259) for the physiological or environmental parameter, then prognosis engine 250 generates a first severity score for the physiological or environmental parameter and the corresponding subject. At block 542, if a respectively generated machine readable value indicative of a physiological or environmental parameter is greater than a respective predetermined severity threshold (e.g. in severity threshold 259) for the physiological or environmental parameter, then prognosis engine 250 generates a second severity score for the physiological or environmental parameter and the corresponding subject. For example, if a respectively generated machine readable value indicative of pulse oximetry is less than a respective predetermined severity threshold for pulse oximetry, then prognosis engine 250 generates a first severity score for pulse oximetry and the corresponding subject by performing a predetermined operation (e.g. addition, subtraction, multiplication, division, etc.) of a predetermined amount on the pulse oximetry value. Additionally, by way of example, if a respectively generated machine readable value indicative of pulse oximetry is greater than a respective predetermined severity threshold for pulse oximetry, then prognosis engine 250 generates a second severity score for pulse oximetry and the corresponding subject by performing the same or another predetermined operation (e.g. addition, subtraction, multiplication, division, etc.) of a different predetermined amount on the pulse oximetry value.

In various embodiments, prognosis engine 250 determines whether the respectively generated machine readable values indicative of the physiological and environmental parameters and respectively cached machine readable values indicative of the physiological and environmental parameters are greater than respective predetermined severity thresholds (e.g. in severity threshold 259) for the physiological and environmental parameters. For example, if the respectively generated, and respectively cached, machine readable values indicative of a trend pulse oximetry is less than a respective predetermined severity threshold for a trend in pulse oximetry, then prognosis engine 250 generates a first severity score for pulse oximetry and the corresponding subject by performing a predetermined operation (e.g. addition, subtraction, multiplication, division, etc.) of a predetermined amount on the pulse oximetry value. Additionally, by way of example, if the respectively generated, and respectively cached, machine readable values indicative of a trend in pulse oximetry is greater than a respective predetermined severity threshold for a trend in pulse oximetry, then prognosis engine 250 generates a second severity score for pulse oximetry and the corresponding subject by performing the same or another predetermined operation (e.g. addition, subtraction, multiplication, division, etc.) of a different predetermined amount on the pulse oximetry value.

Referring back to FIG. 5B, at block 545, prognosis engine 250 determines whether the respectively generated machine readable values indicative of the parameters at block 534 are greater than respective predetermined severity thresholds (e.g. in severity threshold 259) for such parameters. At block 543, if a respectively generated machine readable value indicative of a parameter at block 534 is less than a respective predetermined severity threshold (e.g. in severity threshold 259) for the parameter, then prognosis engine 250 generates a first severity score for the parameter and the corresponding subject. At block 542, if a respectively generated machine readable value indicative of a parameter at block 534 is greater than a respective predetermined severity threshold (e.g. in severity threshold 259) for the parameter, then prognosis engine 250 generates a second severity score for the parameter and the corresponding subject. For example, if a respectively generated machine readable value indicative of distance between a subject and a user of mobile communication and display device is less than a respective predetermined severity threshold for such distance, then prognosis engine 250 generates a first severity score for such distance and the corresponding subject by performing a predetermined operation (e.g. addition, subtraction, multiplication, division, etc.) of a predetermined amount on the generated distance value. Additionally, for example, if a respectively generated machine readable value indicative of such distance is greater than a respective predetermined severity threshold for such distance, then prognosis engine 250 generates a second severity score for such distance and the corresponding subject by performing the same or another predetermined operation (e.g. addition, subtraction, multiplication, division, etc.) of a different predetermined amount on the generated distance value. For example, if a respectively generated machine readable value indicative of orientation is of a first particular type (e.g. lying face down), then prognosis engine 250 generates a first severity score for such orientation and the corresponding subject by performing a predetermined operation (e.g. addition, subtraction, multiplication, division, etc.) of a predetermined amount on the generated orientation value. Additionally, for example, if a respectively generated machine readable value indicative of orientation is of a second particular type (e.g. standing), then prognosis engine 250 generates a second severity score for such orientation and the corresponding subject by performing the same or another predetermined operation (e.g. addition, subtraction, multiplication, division, etc.) of a different predetermined amount on the generated orientation value.

In various embodiments, prognosis engine 250 determines whether the respectively generated machine readable values indicative of a parameter (e.g. orientation, movement, location) and respectively cached machine readable values indicative of the parameter are greater than respective predetermined severity thresholds (e.g. in severity threshold 259) for the parameter. For example, if the respectively generated, and respectively cached, machine readable values indicative of a trend in orientation is of a first trending type (e.g. standing up to laying face up), then prognosis engine 250 generates a first severity score for such trend in orientation and the corresponding subject by performing a predetermined operation (e.g. addition, subtraction, multiplication, division, etc.) of a predetermined amount on the generated orientation value. Additionally, for example, if the respectively generated, and respectively cached, machine readable values indicative of a trend in orientation is of a second particular type (e.g. lying face down to sitting up), then prognosis engine 250 generates a second severity score for such trend in orientation and the corresponding subject by performing the same or another predetermined operation (e.g. addition, subtraction, multiplication, division, etc.) of a different predetermined amount on the generated orientation value.

Referring back to FIG. 5C, at block 549, prognosis engine 250 determines whether the respectively generated machine readable values indicative of pain index are greater than respective predetermined severity thresholds (e.g. in severity threshold 259) for pain index. At block 549, if a respectively generated machine readable value indicative of pain index is less than a respective predetermined severity threshold (e.g. in severity threshold 259) for pain index, then the method returns to block 500 at block 505. At block 549, if a respectively generated machine readable value indicative of pain index is greater than a respective predetermined severity threshold (e.g. in severity threshold 259) for pain index, then prognosis engine 250 generates a respective weighting factor for pain index and the corresponding subject. At block 547, prognosis engine 250 determines whether the respectively generated machine readable values indicative of sound indicates one or more of a predetermined sound type (e.g. a scream). At block 547, if a respectively generated machine readable value indicative of sound does not indicate one or more of the predetermined sound types, then the method returns to block 500 at block 505. At block 547, if a respectively generated machine readable value indicative of sound indicates one or more of the predetermined sound types, then prognosis engine 250 generates a respective weighting factor for the predetermined sound type and the corresponding subject. At block 547, prognosis engine 250 determines whether the respectively generated machine readable values indicative of liquid indicates excessive bleeding. At block 548, if a respectively generated machine readable value indicative of liquid does not indicate excessive bleeding, then the method returns to block 500 at block 505. At block 548, if a respectively generated machine readable value indicative of liquid indicates excessive bleeding, then prognosis engine 250 generates a respective weighting factor for the indication of excessive bleeding and the corresponding subject.

In various embodiments, prognosis engine 250 determines whether the respectively generated machine readable values indicative of a parameter (e.g. liquid, sound) and respectively cached machine readable values indicative of the parameter are greater than respective predetermined severity thresholds (e.g. in severity threshold 259) for the parameter. For example, if the respectively generated, and respectively cached, machine readable values indicative of a trend in liquid (e.g. no change in liquid indicated) are less than a respective predetermined severity threshold for a trend in liquid, then prognosis engine 250 returns the method to block 500. Additionally, by way of example, if the respectively generated, and respectively cached, machine readable values indicative of a trend in liquid (e.g. increasing amount of liquid indicated) is greater than a respective predetermined severity threshold for a trend in liquid, then prognosis engine 250 generates a respective weighting factor for the indication of the trend in liquid and the corresponding subject.

Figure 6:
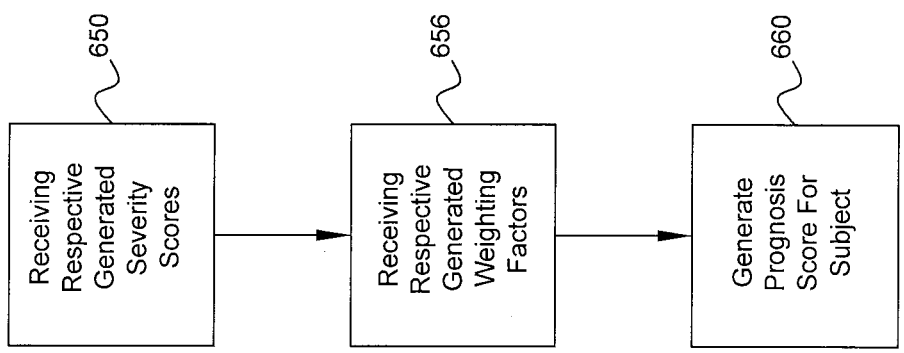
FIG. 6 is a flow chart illustrating a computer-implemented method of automated triage prioritization according to some embodiments.
Figure 7:
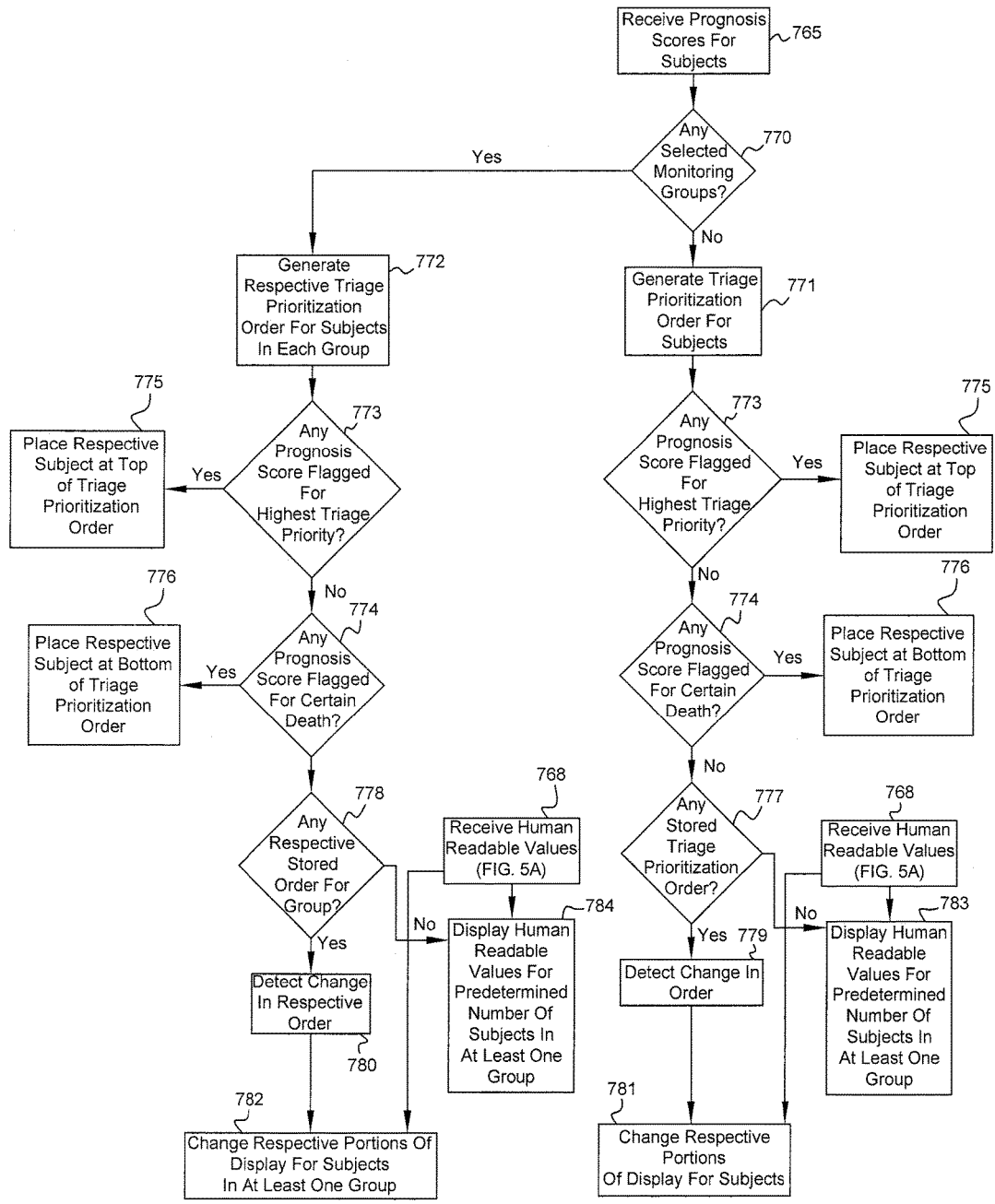
FIG. 7 is a flow chart illustrating a computer-implemented method of automated triage prioritization in accordance with some embodiments of the present subject matter.

Referring now to FIGS. 6-7, computer-implemented methods of automated triage prioritization are provided. At block 650, prognosis engine 250 receives respective generated severity scores (at blocks 544, 543, 511, 542) for each of the plurality of subjects 200-N. At block 650, prognosis engine 250 receives respective generated weighting factors (at block 555, weighting factor module 258) for each of the plurality of subjects 200-N. At block 650, prognosis engine 250 generates respective prognosis scores for each of the plurality of subjects 200-N using the generated respective severity scores and the received plurality of predetermined weighting factors. At block 765, triage prioritization engine 260-A receives the generated prognosis scores for each of the plurality of subjects 200-N from the prognosis engine 250. At block 768, triage prioritization engine 260-A receives the respectively generated human readable values for each of the subjects (blocks 535, 532) At block 770, triage prioritization engine 260-A determines whether there are any selected monitoring groups (e.g. two or more subjects within a predetermined distance of location A, two or more subjects within a predetermined distance of location B). At block 771, if triage prioritization engine 260-A determines that there are no selected monitoring groups, then triage prioritization engine 260-A generates a triage prioritization order of the subjects (e.g. subject-8 triage priority 1, subject-3 triage priority 2, subject-1 triage priority 3, etc.) using the generated prognosis scores.

In various embodiments, prognosis engine 250 may flag a subject's prognosis score for highest or lowest triage priority. In various embodiments, prognosis engine 250 may flag a subject's prognosis score for highest or lowest triage priority using the generated, and/or cached, machine readable values, severity scores, and/or weighting factors. For example, prognosis engine 250 may flag a subject's prognosis score for highest triage priority if the generated prognosis score indicates severe heart beat issues, severe breathing issues, or quick operations. For example, prognosis engine 250 may flag a subject's prognosis score for lowest triage priority if the generated prognosis score indicates that there is a greater than a predetermined probability threshold that the subject is certain to die. At blocks 773 and 774, triage prioritization engine 260-A determines whether any prognosis scores have been flagged for highest or lowest triage priority respectively. If triage prioritization engine 260-A determines a subject's prognosis scores has been flagged for highest triage priority, at block 775, triage prioritization engine 260-A will select the subject for the highest triage priority position in the generated triage prioritization order. If triage prioritization engine 260-A determines a subject's prognosis scores has been flagged for lowest triage priority, at block 776, triage prioritization engine 260-A will select the subject for the lowest triage priority position in the generated triage prioritization order.

At block 777, triage prioritization engine 260-A determines whether a triage prioritization order for the subjects is cached in memory of the mobile communication and display device. If triage prioritization engine 260-A determines that there is no cached triage prioritization order for the subjects, at block 783, triage prioritization engine 260-A will interface with subject monitoring cores 240-N and user interface 245 (and/or communication interface B 247, command center server 280 and user interface 275) to display the generated respective human readable values for at a predetermined number (e.g. 2, 4, 6) of the subjects on respective portions of the user interface 245 based on the generated triage prioritization order. For example, if triage prioritization engine 260-A determines that there is no cached triage prioritization order for the subjects, triage prioritization engine 260-A will interface with subject monitoring cores 240-N and user interface 245, to display the generated respective human readable values for the subject with the determined highest triage priority in a top portion of the user interface 245, for the subject with the determined second highest triage priority in a portion of the user interface 245 below the top portion, for the subject with the determined third highest triage priority in portion of the user interface 245 below the portion displaying the generated respective human readable values for the subject with the second highest triage priority, and so on.

At block 777, if triage prioritization engine 260-A determines that there is a cached triage prioritization order for the subjects, triage prioritization engine 260-A will detect whether there is a change between the generated and cached triage prioritization orders for the subjects at block 779. If triage prioritization engine 260-A does not detect a change between the generated and cached triage prioritization orders for the subjects, triage prioritization engine 260-A will interface with subject monitoring cores 240-N and user interface 245, to update the displays of the generated respective human readable values for the subjects. At block 781, if triage prioritization engine 260-A does detect a change between the generated and cached triage prioritization orders for the subjects, triage prioritization engine 260-A will interface with subject monitoring cores 240-N and user interface 245, to change the respective portions of the display of the respective generated human readable values for the subjects based on the detected change in the triage prioritization order. For example, if triage prioritization engine 260-A detects a change in the triage prioritization order for subject-3 and subject-8 based on the stored (e.g. cached) prognosis scores for subject-3 and subject-8, the received generated respective new prognosis score for subject-3 and subject-8 (block 765), and the stored (e.g. cached) triage prioritization order; triage prioritization engine 260-A will interface with subject monitoring cores 240-N and user interface 245, to change the respective portions of the display of the respective generated human readable values for subject-3 and subject-8.

At block 772, triage prioritization engine 260-A interfaces with subject monitoring cores 240-N and user interface 245 (and/or communication interface B 247, command center server 280 and user interface 275) to display the generated respective human readable values for at a predetermined number (e.g. 2, 4, 6) of the subjects on respective portions of the user interface 245 based on the generated triage prioritization order. For example, if triage prioritization engine 260-A determines that there is no cached triage prioritization order for the subjects, triage prioritization engine 260-A will interface with subject monitoring cores 240-N and user interface 245, to display the generated respective human readable values for the subject with the determined highest triage priority in a top portion of the user interface 245, for the subject with the determined second highest triage priority in a portion of the user interface 245 below the top portion, for the subject with the determined third highest triage priority in portion of the user interface 245 below the portion displaying the generated respective human readable values for the subject with the second highest triage priority, and so on.

At block 772, if triage prioritization engine 260-A determines that there are at least two selected monitoring groups (e.g. monitoring group A and monitoring group B), then triage prioritization engine 260-A and triage prioritization engine 260-B generated a triage prioritization order of the subjects in each of the monitoring groups A and B as described above for block 771. At blocks 773 and 774, triage prioritization engine 260-A and triage prioritization engine 260-B respectively determine whether any prognosis scores in each respective monitoring group A and B have been flagged for highest or lowest triage priority respectively as described above for blocks 773 and 774. If either of triage prioritization engine 260-A or triage prioritization engine 260-B determines a subject's prognosis scores in the respective monitoring group has been flagged for highest triage priority, at block 775, the respective triage prioritization engine 260 will select the subject for the highest triage priority position in the generated triage prioritization order for the selected monitoring group as described above for block 775. If either of triage prioritization engine 260-A or triage prioritization engine 260-B determines a subject's prognosis scores in the respective monitoring group has been flagged for lowest triage priority, at block 776, the respective triage prioritization engine 260 will select the subject for the lowest triage priority position in the generated triage prioritization order for the selected monitoring group as described above for block 775.

At block 778, triage prioritization engine 260-A and triage prioritization engine 260-B each determine whether a triage prioritization order for the subjects in each respective monitoring group is cached in memory of the mobile communication and display device as described above for block 777. At block 778, if either of triage prioritization engine 260-A or triage prioritization engine 260-B determines that there is no cached triage prioritization order for the subjects in the respective monitoring group, at block 784, the respective triage prioritization engine 260 will interface with subject monitoring cores 240-N and user interface 245 (and/or communication interface B 247, command center server 280 and user interface 275) to display the generated respective human readable values for a predetermined number (e.g. 2, 4, 6) of the subjects on respective portions of the user interface 245 based on the generated triage prioritization order for the respective monitoring group as described above for block 783.

At block 778, if either of triage prioritization engine 260-A or triage prioritization engine 260-B determines that there is a cached triage prioritization order for the subjects in a respective monitoring group, at block 784, the respective triage prioritization engine 260 will detect whether there is a change between the generated and cached triage prioritization orders for the subjects in the respective monitoring group at block 780 as described above for block 779. If triage prioritization engine 260-A does not detect a change between the generated and cached triage prioritization orders for the subjects, triage prioritization engine 260-A will interface with subject monitoring cores 240-N and user interface 245, to update the displays of the generated respective human readable values for the subjects. At block 782, if either of triage prioritization engine 260-A or triage prioritization engine 260-B determines a change between the generated and cached triage prioritization orders for the subjects in a respective monitoring group, the respective triage prioritization engine 260 will interface with subject monitoring cores 240-N and user interface 245, to change the respective portions of the display of the respective generated human readable values for the subjects in the respective monitoring group based on the detected change in the triage prioritization order as described above for block 781.

Figure 8:
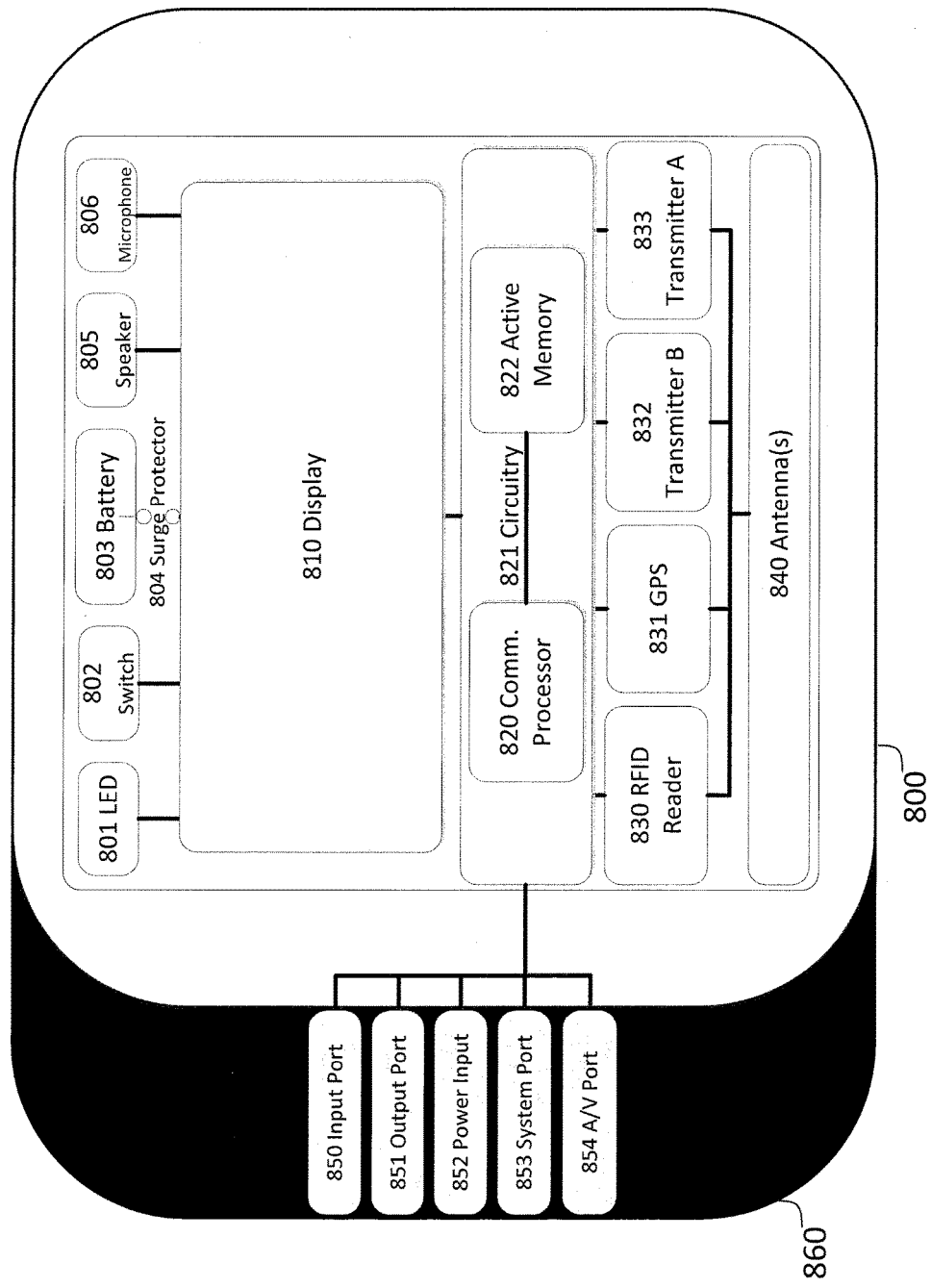
FIG. 8 is a block diagram of an example of a mobile communication and display device in accordance with some embodiments.

FIG. 8 is a block diagram of an example of a mobile communication display device according to some embodiments of the present disclosure. In various embodiments, mobile communication display device 800 includes electrical components configured to transmit, receive, process, and display data. In various embodiments, mobile communication display device 800 includes a communications processor 820 configured to manage the processing and data flow of mobile communication display device 800. In various embodiments, mobile communication display device 800 includes an active memory 822 such as, for example, a memory buffer, configured to hold instructions and data in a cached state for processing, transmission, and presentation purposes. In various embodiments, mobile communication display device 800 includes circuitry 821 such as, for example, embedded electronic circuitry configured to connect various components of mobile communication display device 800 to each other. In various embodiments, RFID reader 830 includes an RFID reader configured to read unique identification strings of a plurality of monitoring devices 140. In various embodiments, an RFID tag of each monitoring device 140 broadcasts its respective unique identification string for registration purposes with mobile communication display device 800. In various embodiments, mobile communication display device 800 includes a barcode reader 830, a QR code reader 830, or any suitable identification code reader 830, configured to read monitoring devices' respective barcode, QR code, or suitable identification code for registration purposes with mobile communication display device 800. In various embodiments, RFID reader 830 receives a unique identification string of a monitoring device (140) if such monitoring device (140) is within range of RFID reader 830 and the RFID reader 830 has confirmed that the device is a monitoring device (140). In various embodiments, scanning a previously registered monitoring device (140) on mobile communication display device's 800 RFID reader 830 will automatically re-register this monitoring device (140) to its previously registered subject.

In various embodiments, mobile communication display device 800 includes a location subsystem, such as for example, GPS 831 including a GPS unit configured to use the global GPS network to determine global coordinates within a predetermined tolerance. In various embodiments, mobile communication display device 800 includes a transmitter 832 configured to transmit data received, stored, and/or generated, by mobile communication display device 800 over a network (e.g. over 802.11, Wi-Fi, 3G/4G/5G cellular, RF, VHF/UHF or other high frequency radio network, satellite network, IP network, a private network, virtual private network (VPN), relay network, the Internet, a Non-secure Internet Protocol Router Network (NIPRNet), a Secret Internet Protocol Router Network (SIPRNet), a Single Channel Ground and Airborne Radio System (SINCGARS), Link-16 (also known as "J2 Coding" or "J2 Messaging" or "TADL" or "SADL"), a cloud computing network, etc.). In various embodiments, this connection could be performed with the inboard connectivity features of the mobile communication and display device. In various embodiments, mobile communication display device 800 includes a wireless (e.g. Bluetooth) transmitter 833 configured to transmit data over a wireless network including, for example, data transmissions between mobile communication display device and computer software applications, one or more of a plurality of monitoring devices 140, one or more notification devices (not shown), one or more wireless headsets or other audio presentation and recording devices (not shown), and/or other mobile communication and display devices. In various embodiments, a mobile communication and display device of one user (e.g. medic, first responder, physician) can communicate with another mobile communication and display device of another user such as, for example, to turnover on-scene duties from the first user to the second user by transmitting subject (200-N), monitoring device (140), and/or environment, data over a wireless (e.g. Bluetooth, NFC) network using transmitter 833, and/or via a software application (e.g. mobile application) operating on both mobile communication and display devices (e.g. Bump application). In various embodiments, RFID reader 830, GPS 831, transmitter 832, and wireless transmitter 833 are each configured to connect to antenna(s)

840, such as, for example, a set of antennas for data transmissions. In various embodiments, processor 820 is configured to control the processing and data flow of various components, subsystems, and modules of mobile communication display device 800 including, for example, subcomponent LEDs, vibration devices, speakers, microphones, antennas, batteries, surge protectors, etc. In various embodiments, mobile communication display device 800 is configured to detect available frequencies (e.g. electromagnetic frequencies) and to modify its, and any monitoring devices (140) that it is receiving communications from, transmission protocols to a selected one of a plurality of new frequencies. The inventors have determined that the ability to detect available frequencies, and modify transmission protocols to a selected one of a plurality of new frequencies, is an important feature in situations where radio transmission frequencies are blocked, restricted, or jammed, such as in a battlefield scenario or hospital. The inventors have also determined that, due to the increase in the use of devices that saturate the electromagnetic spectrum on the battlefield and hospitals, in such environments, it may be of vital importance for mobile communication display devices 800 to have simple logic to exploit open bandwidths for data transmission via frequency hopping especially in battlefield scenarios where different portions of the electromagnetic spectrums are saturated or denied by friendly or enemy forces.

In various embodiments, mobile communication display device 800 includes a battery 803 configured to power various components and electronic subsystems of mobile communication display device 800. For example, battery 803 may be a long-life battery, and depending on a particular application or environment, may be removable or non-removable. In various embodiments, battery 803 connects to circuitry 821 via surge protector 804 to ensure consistent electrical power flow to various components and electronic subsystems of mobile communication display device 800 and prevent damage or overheating from short circuits. In various embodiments, mobile communication display device 800 includes a LED 401 such as, for example, a multi-color LED light, configured to programmatically display different color notifications with different flash patterns, frequencies, and intensities. In various embodiments, mobile communication display device 800 includes a switch 802 such as, for example, a multi-positional switch, configured to activate different modes on mobile communication display device 800, such as, for example, a 2-way communication mode, a 1-way communication mode, a mute mode, a LED active mode, a LED disable mode, a system status mode, a diagnostic mode, etc. In various embodiments, mobile communication display device 800 includes a speaker 805 such as, for example, an audio speaker with a programmatic volume setting, a video camera and speaker combination unit configured to simultaneously take audio and video recordings of, for example, the surroundings of mobile communication display device 800 for remote review or visual teleconference communications. In various embodiments, mobile communication display device 800 includes a microphone 806 such as, for example, an audio microphone with a programmatic gain setting. In various embodiments, mobile communication display device 800 includes a display 810 such as, for example, a multi-line display configured to display high quality video, graphics, and text.

In various embodiments, mobile communication display device 800 includes an input port 850 configured to utilize any suitable wired connection technology to transmit data and electricity, such as, for example, MicroUSB. Any suitable wired connection technology can be utilized by input port 850. In various embodiments, mobile communication display device 800 includes an output port 851 utilizes any suitable wired connection technology to transmit data and electricity, such as, for example, MicroUSB, with other computing devices and network nodes, such as, for example, lightning, 30 pin connectors, USB, Ethernet, parallel connections, RS-232, MIL-STD-144-114A, or other serial connections. In various embodiments, mobile communication display device 800 is configured to be powered from its input port 850, output port 851, or the dedicated power input 852 configured to receive suitable electrical inputs, such as, for example, 3V, 12V, 110V, and 220V electrical inputs. In various embodiments, if mobile communication display device 800 is powered from its input port 850 or dedicated power input 852, then mobile communication display device 800 will supply such power to a downstream device connected to output port 851. In various embodiments, mobile communication display device 800 includes a system port 853 configured to provide diagnostics and upgrades to mobile communication display device 800. In various embodiments, system port 853 is a suitable data connection, such as, for example, USB 3.0. In various embodiments, mobile communication display device 800 is configured to be connected via system port 853 to other computing devices or to flash drives. In various embodiments, various power connections are configured to be connected via surge protector 804 to ensure consistent electrical power flow to mobile communication display device 800 and prevent damage or overheating from short circuits. In various embodiments, mobile communication display device 800 includes an A/V port 854 configured to connect mobile communication display device 800 to A/V devices such as, for example, headsets with over-ear headphones for audio and video with a microphone. In various embodiments, mobile communication display device 800 includes a side panel 860 such as, for example, the side panel of mobile communication display device 800. In various embodiments, side panel 860 is the location of the external, wired data connection ports.

Figure 9A:
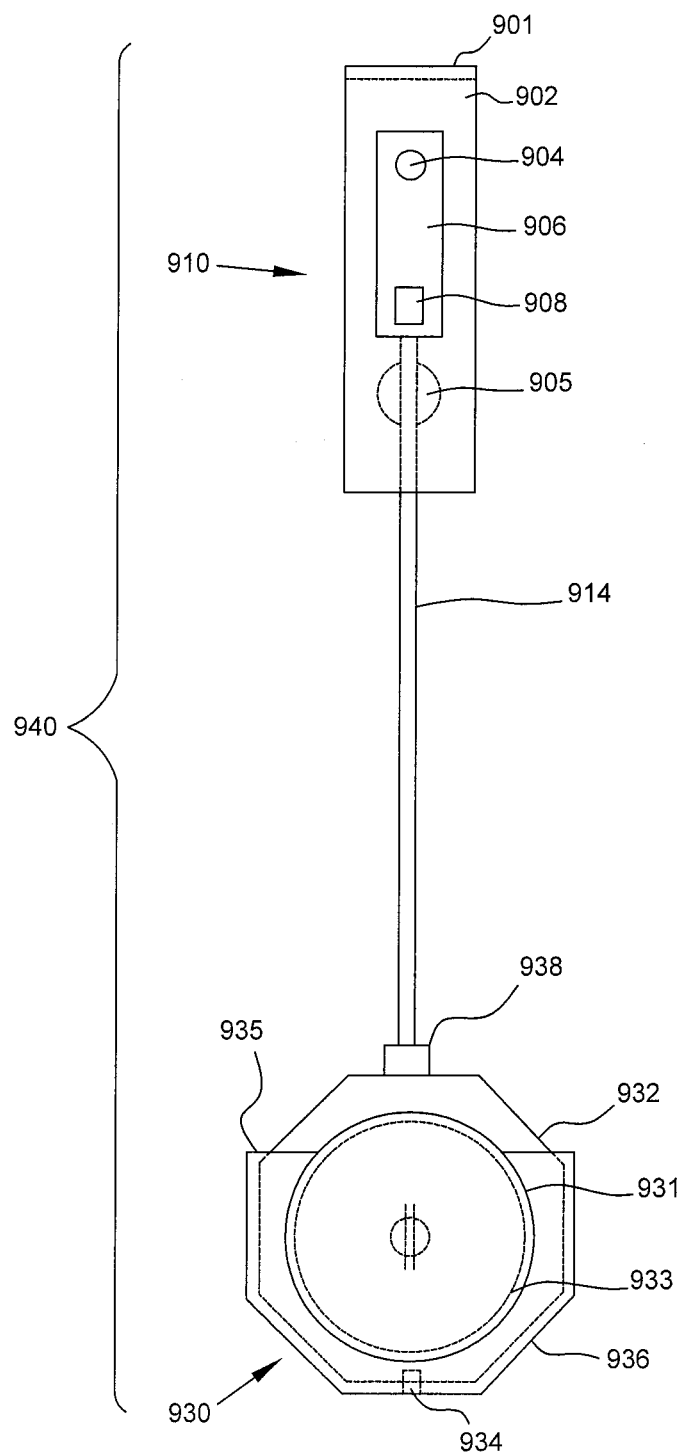
FIG. 9A is a front elevation view of an example of a monitoring device including first and second portions according to some embodiments.
Figure 9B:
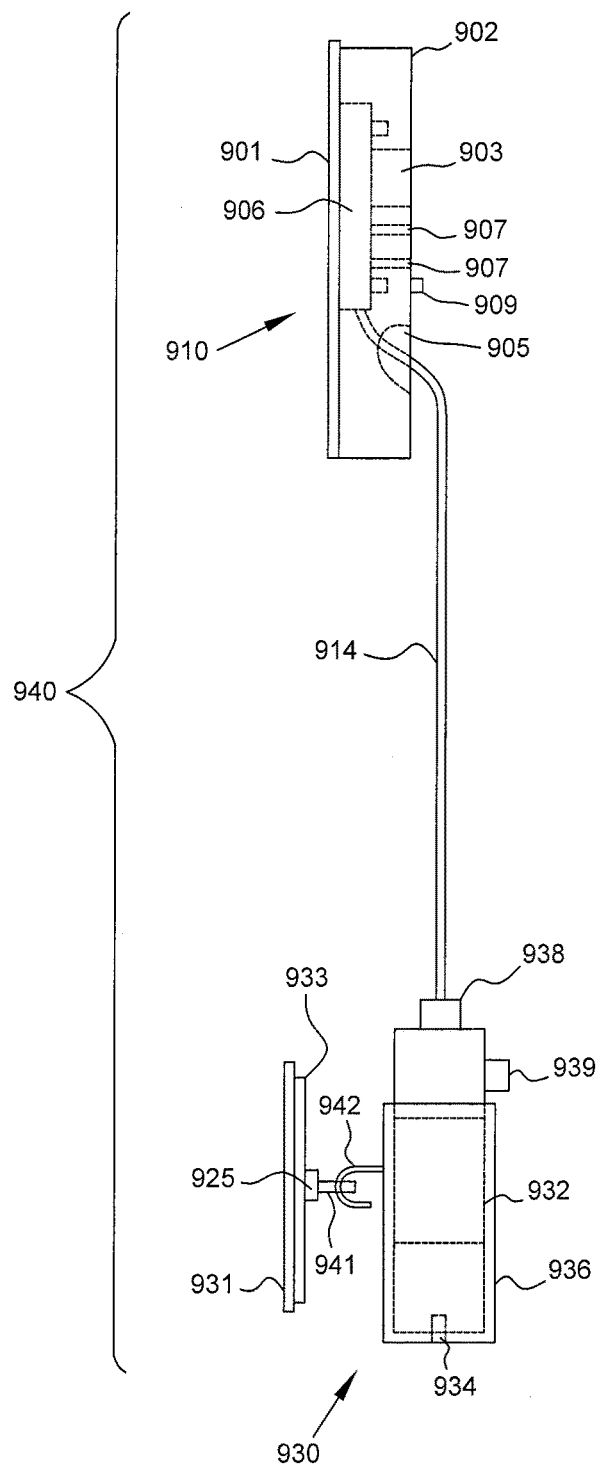
FIG. 9B is a side elevation view of an example of a monitoring device including first and second portions according to some embodiments.
Figure 9C:
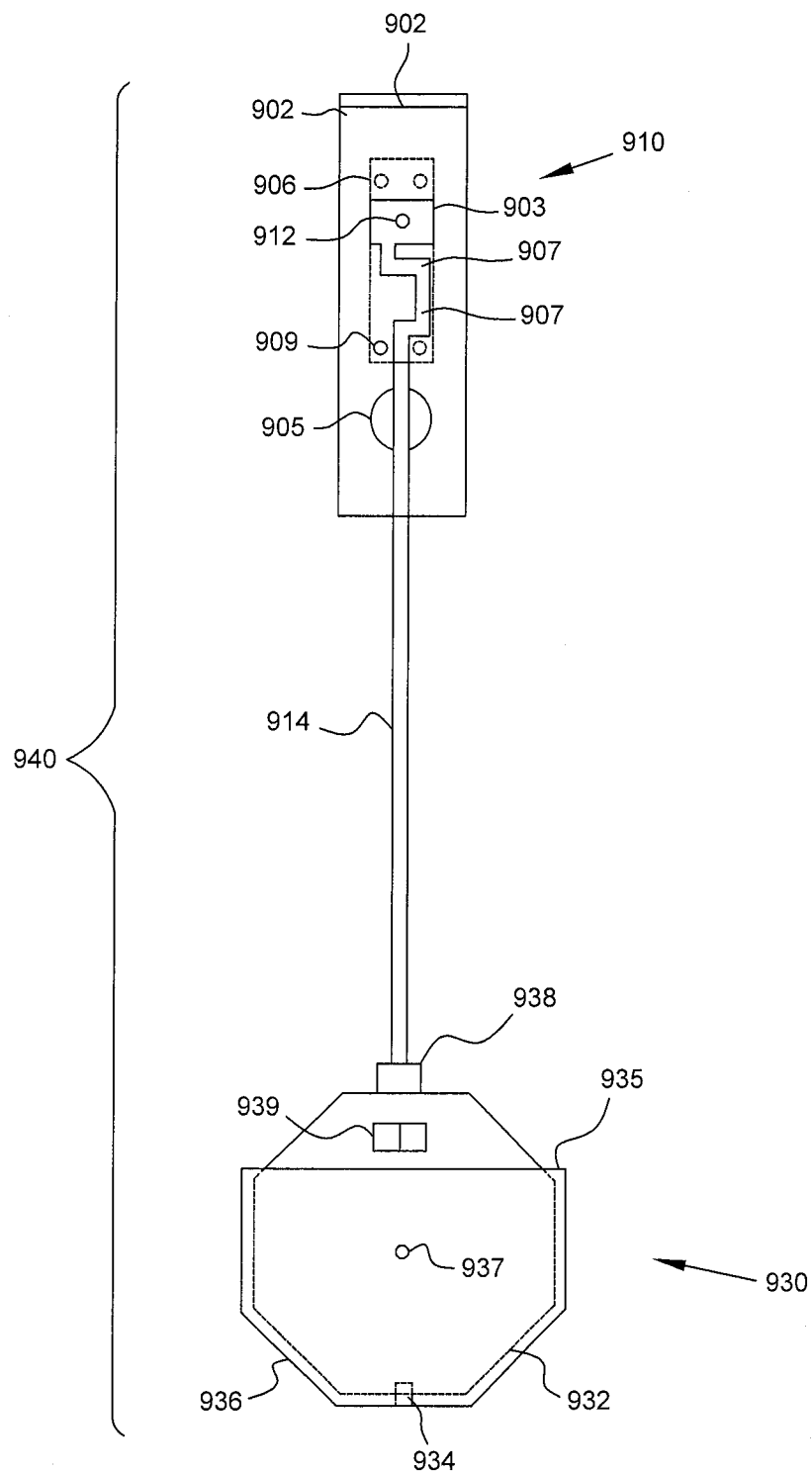
FIG. 9C is a rear elevation view of an example of a monitoring device including first and second portions according to some embodiments.

Referring now to FIGS. 9A-9C, front, side, and rear elevation views of an example of a monitoring device 940 including first 910 and second 920 portions according to some embodiments of the present disclosure is provided. As illustrated in FIGS. 9A-9C, monitoring device 940 may be a modular, non-invasive, wearable, and minimally-intrusive context-aware physiological, physical, and environmental, parameters monitoring device. In various embodiments, as illustrated in FIG. 9A, housing 906 includes one or more openings 904, and one or more openings 908, that are configured to facilitate operation of an electrode subsystem of monitoring device 940, including an electrode subsystem of first portion 910 and/or an electrode subsystem of second portion 930, housed within housing 906 and housing 932 respectively. In various embodiments, housing 906 includes one or more openings 904, and one or more openings 908, that are configured to facilitate operation of one or more indicators 912 (e.g. one or more LEDs or other display) that are part of an electronic subsystem of monitoring device 940. Housing 906 may be formed from any suitable material such as, for example, a partially or fully rigid or pliable, sturdy, elastomeric, parylene, overcoat, plastic, glass, magnetic, metal, or other material, or combinations thereof. In various embodiments, housing 906 may have a minimal footprint (e.g. 10-75 mm (length), 10-75 mm (width), 1-25 mm (height)), ergonomic, and versatile, form configured to fully or partially house and protect some or all of an electronic subsystem of monitoring device 940. In various embodiments, housing 906 may have a form configured to facilitate deployment at a surface of an ear of a subject opposite the concha of the subject, or other suitable body or other location, including, for example, to housing 902 via opening 902, slit 907, and/or boss 900. In various embodiments, housing 906 is connected to housing 902 by a magnetic attachment (e.g. using ceramic, alnico, neodymium, samarium cobalt, magnets).

In various embodiments, as illustrated in FIG. 9B, housing 906 includes one or more openings 903, slits 304, opening 907, and boss 909, configured to facilitate inserting and/or securing housing 906 and part of housing 914 to housing 902 while enabling movement of part of housing 914 in many degrees of freedom via opening 905. In various embodiments, as illustrated in FIG. 9B, housing 906 includes one or more openings 903, slits 304, opening 907, and boss 909, configured to facilitate utilizing, for example, boss 909 to align housing 903 for proper placement on a surface of a subject ear opposite the concha, or other suitable body surface, or other location. In various embodiments, cover 901 may be a removable or permanent part of housing 902 and can include one or more replaceable and/or reusable, or irreplaceable and/or non-reusable, adhesive material configured to facilitate affixing housing 902 and/or housing 906 to a surface of a subject ear opposite the concha, or other suitable body surface, or other location. Housing 902 may be formed from any suitable material such as, for example, a partially or fully rigid or pliable, sturdy, elastomeric, parylene, overcoat, plastic, glass, magnetic, metal, or other material, or combinations thereof. In various embodiments, housing 902 may have a minimal footprint (e.g. 10-75 mm (length), 10-75 mm (width), 1-25 mm (height)), ergonomic, and versatile, form configured to fully or partially house and protect some or all of housing 906 and/or housing 914, and/or to facilitate affixing housing 902 to a surface of a subject ear opposite the concha, or other suitable body surface, or other location.

In various embodiments, housing 902 and/or housing 906 can be implemented ornamentally and/or in a plurality of forms, including, for example, further segmentation into several pieces, or combination as one piece, to facilitate a more efficient assembly and use. For example, in some embodiments, a piece that includes a combination of housing 902 and housing 906, and that is configured to be positioned on a surface of a subject ear opposite the concha, or other suitable body surface, or other location, may have an extension in the form of a hook, for example, that is configured to anchor to a piercing on, or in, a subject's ear, or other location, to secure the piece to the ear. In various embodiments, housing 902 and/or housing 906 may be configured to be affixed to a subject's ear as a smart earring, or a portion thereof.

In various embodiments, housing 914 may be formed from any suitable material such as, for example, a partially or fully rigid or pliable, sturdy, elastomeric, plastic, fiber-reinforced liquid silicone rubber, glass, metal, or other material, or combinations thereof, or combinations thereof. In various embodiments, housing 914 may have a minimal footprint (e.g. 0.2-10 mm diameter), ergonomic, and versatile, form configured to fully or partially house and protect some or all of electromechanical subsystem 114 (FIG. 1), and/or to facilitate being positioned on a surface on or near the neck of a subject, or other suitable body surface, or other location. In various embodiments, housing 914 may include one or more minimal footprint (e.g. 0.2-10 mm diameter), and ergonomically designed, hollow pieces with two or more ends. In various embodiments, housing 914 includes a first end configured to be partially or fully continuous with housing 906. In various embodiments, housing 914 includes a first end configured to be separate from housing 906. In various embodiments, housing 914 includes a second end configured to interface with one or more connector 938, or to be partially or fully continuous with housing 936 and/or housing 932. In various embodiments, connector 938 may be configured to have one of a plurality of forms, including, for example, a magnetic form. In various embodiments, connector 938 may be configured to facilitate connecting electromechanical subsystem 114 (FIG. 1) to an electronic subsystem of a second portion 930 of monitoring device 940, and/or to other electronic or other subsystems.

In various embodiments, housing 914 can be implemented ornamentally and/or in a plurality of forms, including, for example, further segmentation into several pieces, and/or modification into various forms. For example, in some embodiments, housing 914 can include one, two, or more, separate and/or continuous pieces. In some embodiments, a first piece is configured to have a form that enables it to be fully or partially worn or wrapped around the neck, or other area, of a subject body. In some embodiments, a second and third piece are configured to have forms that enable them to extend from an area on a first (e.g. right) or second (e.g. left) ear surfaces of a subject to the neck, or other area, of the subject's body. In some embodiments, a fourth and fifth piece are each configured to have forms that enable them to extend from a neck of a subject, or other area, to other body locations that facilitate proper measurements of signals of interest such as, for example, electrical potential signals. In various embodiments, an assembly including a plurality (e.g. first, second, third, fourth, fifth) pieces of housing 914, electromechanical subsystem 114 (FIG. 1), an electronic subsystem of monitoring device 140 (940) including an electronic subsystem of a second portion 120 (930) of such monitoring device, can be considered a smart necklace, or portion thereof. In various embodiments, an electromechanical subsystem 114 (FIG. 1) may be configured such that it may be housed in pieces of housing 914, and to extend outwards from one or more openings in housing 914 to connect to external sensor and/or electronic subsystems, such as, for example, electrical potential electrodes and/or subsystems.

In various embodiments, housing 914, and an electronic subsystem of monitoring device 140 (940) including an electronic subsystem of first 110 (910) and/or second 120 (930) portions of monitoring device 140 (940), may be configured to facilitate the connection and disconnection of one or more external sensor and/or electronic subsystems such as, for example, electrical potential electrodes, subsystems, and/or a capnometer. In various embodiments, housing 914 is implemented in a form configured to adhere and/or affix at least a portion of housing 914 to a surface of a subject's body, or other location, to minimize motion of housing 914.

In various embodiments, as illustrated in FIG. 9B, housing 932 includes one or more openings to facilitate the operation of, for example, an electronic subsystem of a second portion 120 (930) of a monitoring device 140 (940), one or more switches 939 (e.g. on/off, or other, switches that are part of an electronic subsystem of a second portion 120 (930) of a monitoring device 140 (940), indicators 402 (e.g. LEDs or other display) that are part of an electronic subsystem of a second portion 120 (930) of a monitoring device 140 (940), connector 938). In various embodiments, housing 932 may be configured to preclude opening thereof. In various embodiments, housing 932 may be configured to facilitate temporary opening and closing to, for example, enable replacing a replaceable power source subsystem 128 (FIG. 1). In various embodiments, housing 932 may be formed from any suitable material such as, for example, a partially or fully rigid or pliable, sturdy, elastomeric, parylene, overcoat, fiber-reinforced liquid silicone rubber, plastic, glass, magnetic, metal, or other material, or combinations thereof, or combinations thereof. In various embodiments, housing 932 may have a minimal footprint (e.g. 25-100 mm diameter, 25-100 mm (length), 25-100 mm (width), 1-25 mm (height)), ergonomic, and versatile, form configured to fully or partially house and protect some or all of an electronic subsystem of a second portion 120 (930) of a monitoring device 140 (940), and/or to facilitate being affixed to a surface of a subject's body, or other location, or piece, including to housing 936.

In various embodiments, as illustrated in FIGS. 9B-9C, housing 936 is configured to include, for example, an opening 935, a piece 934, a connecting piece 942, and/or other relevant forms, to facilitate, for example, housing 932 including any attached external electronics such as, for example, electrical potential electrode subsystems, insertion of housing 932 into housing 936 via opening 935, attachment of housing 932 to housing 936, temporarily or permanently securing and/or attaching housing 932 to housing 936, attachment or securing of housing 936 to a surface of a subject's body, a portion of a subject's clothing, or other location, or piece, via one or more connecting pieces 942 that may be included as a part of housing 936, temporarily or permanently attaching or securing connecting piece 942 to one or more connecting pieces 941 either in a rigid form, or in such a form as to enable the movement of connecting piece 942 in many degrees of motion relative to connecting piece 941. In various embodiments, connecting piece 942 and connecting piece 941 are configured to be versatile and have a plurality of mechanisms for connection, such as, for example, a rotational or rigid joint, magnetic, or combinations thereof. In various embodiments, piece 934 can be configured in one of a plurality of forms, including, for example, a magnetic or non-magnetic boss.

In various embodiments, housing 936 may be formed from any suitable material such as, for example, a partially or fully rigid or pliable, sturdy, elastomeric, fiber-reinforced liquid silicone rubber, plastic, glass, magnetic, metal, or other material, or combinations thereof. In various embodiments, housing 936 may have a minimal footprint (e.g. 25-100 mm diameter, 25-100 mm (length), 25-100 mm (width), 1-25 mm (height)), ergonomic, and versatile, form configured to fully or partially house and protect some or all of housing 932, and/or to facilitate being affixed to a surface of a subject's body, or other location, or piece, including being temporarily or permanently affixed to a versatile assembly including some or all of connecting piece 941, piece 925, material 933, and cover 931. In various embodiments, piece 925 may be formed from a rigid or flexible, magnetic, versatile material, or combinations thereof. In various embodiments, piece 925 may be configured to, for example, provide structural support relating to material 933 and connecting piece 941. various embodiments, material 933 may be formed from a versatile, flexible or rigid, magnetic, and/or adhesive material, or combinations thereof. In various embodiments, material 933 may be configured to, for example, facilitate affixing material 933 to a surface of a subject's body, or other location, or piece. In various embodiments, cover 931 may be replaceable and/or reusable, or irreplaceable and/or non-reusable, and formed from one or more adhesive, flexible or rigid, magnetic, or other material, or combinations thereof. In various embodiments, cover 931 may include one or more electronic subassemblies, such as flexible printed circuits and/or printed circuit boards, including a plurality of physiological sensors, as described above for first portion 110 of monitoring device 140, and configured to be deployed (e.g. using an adhesive) on one or more surfaces of a subject, and to transmit electronic signals including physiological sensor data to electronic subsystems of second portion 120 and/or electromechanical interconnect 114 (FIG. 1). In various embodiments, a versatile assembly including some or all of connecting piece 941, piece 925, material 933, and cover 931, may have one of a plurality of forms that facilitate ergonomically, and minimally intrusively, attaching and/or securing said assembly to one or more surfaces of a subject's body, or other location, or piece.

In various embodiments, housing 936, connecting piece 941, a versatile assembly including some or all of connecting piece 941, piece 925, material 933, and cover 931, can be implemented ornamentally and/or in one of a plurality of forms, including, for example, further segmentation into several pieces, or combination as one piece, to facilitate a more efficient assembly and use. In various embodiments, housing 936, connecting piece 941, a versatile assembly including some or all of connecting piece 941, piece 925, material 933, and cover 931, can be implemented in one of a plurality of colors. For example, connecting piece 941 may be adhered, attached and/or clipped to a surface of a subject's body, or other location, or piece. In various embodiments, housing 936 can include one or more securing, and/or attachment, features such as, for example, piece 934 to facilitate temporary and/or permanent attachment of housing 932 to housing 936. In various embodiments, housing 936 has a magnetic form and is shaped similar to a coin, whereby the obverse side can be affixed to a housing 932, and the reverse side includes connecting piece 941. In various embodiments, housing 936 and/or housing 932 may include one or more magnets, or magnetic material, to facilitate temporary and/or permanent attachment of housing 936 and/or housing 932. In various embodiments, housing 936 may include, and/or enable the implementation of, electronics such as, for example, a power source (not shown), a display (not shown), configured as auxiliary electronics for an electronic subsystem of monitoring device 140 (940) including an electronic subsystem of first 110 (910) and/or second 120 (930) portions of monitoring device 140 (940).

In various embodiments, housing 936, connecting piece 941, piece 925, material 933, and cover 931, or combinations thereof, can be configured as a combination of pieces configured to fully, or partially, and temporarily, or permanently, house, protect and facilitate the operation of and connection to housing 932 and or other external electronics. In various embodiments, housing 936, connecting piece 941, piece 925, material 933, and cover 931, or combinations thereof, can be configured as a combination of pieces configured to permit an ergonomic, and minimally intrusive, attachment and/or securing of housing 932 to a surface of a subject's body, or other location, or piece. In various embodiments, housing 936, connecting piece 941, piece 925, material 933, and cover 931, or combinations thereof, can be configured as a combination of pieces configured to implement auxiliary electronics and/or other features relating to the operation of an electronic subsystem of monitoring device 140 (940) including an electronic subsystem of first 110 (910) and/or second 120 (930) portions of monitoring device 140 (940).

Referring now to FIGS. 10A and 10B, side and front elevation views of an example of a second portion 1030 of a monitoring device 940 (140), and illustrating internal components of the same, according to various embodiments of the present disclosure, is provided. In various embodiments, housing 1032 includes a cavity 1046, and an electronic subsystem of a second portion 120 (930) of a monitoring device 140 (940). In various embodiments, cavity 1046 is configured to mate with piece 934 (FIG. 9B). In various embodiments, an electronic subsystem 116 of a second portion 120 (930) of a monitoring device 140 (940) includes a power source subsystem 1038, and a plurality of electronic subassemblies such as flexible printed circuits and/or printed circuit boards. In various embodiments, electronic subassembly 1043, electronic subassembly 1044, electronic subassembly 1045, and electronic subassembly 1048, can be one or more minimal footprint (e.g. 1-25 mm), and ergonomically designed, flexible printed circuit and/or printed circuit board that constitute part of an electronic subsystem 116 of a second portion 120 (930) of a monitoring device 140 (940), and that are configured to connect to each other, and/or to power source subsystem 1038. In various embodiments, housing 1032 includes electronic subassembly 1043, electronic subassembly 1043, electronic subassembly 1045, subassembly 1048, power source subsystem 1038, and cavity 1046. In various embodiments, housing 1032 may have a plurality of forms, and/or be ergonomically configured to, for example, permit replacement of a replaceable power source subsystem 1038, to protect the various components therein, to enable operation of the various components therein, to minimize the footprint and/or weight of housing 1032, and/or to facilitate attachment of housing 1032 to housing 936 (FIGS. 9B, 9C).

Figure 11A:
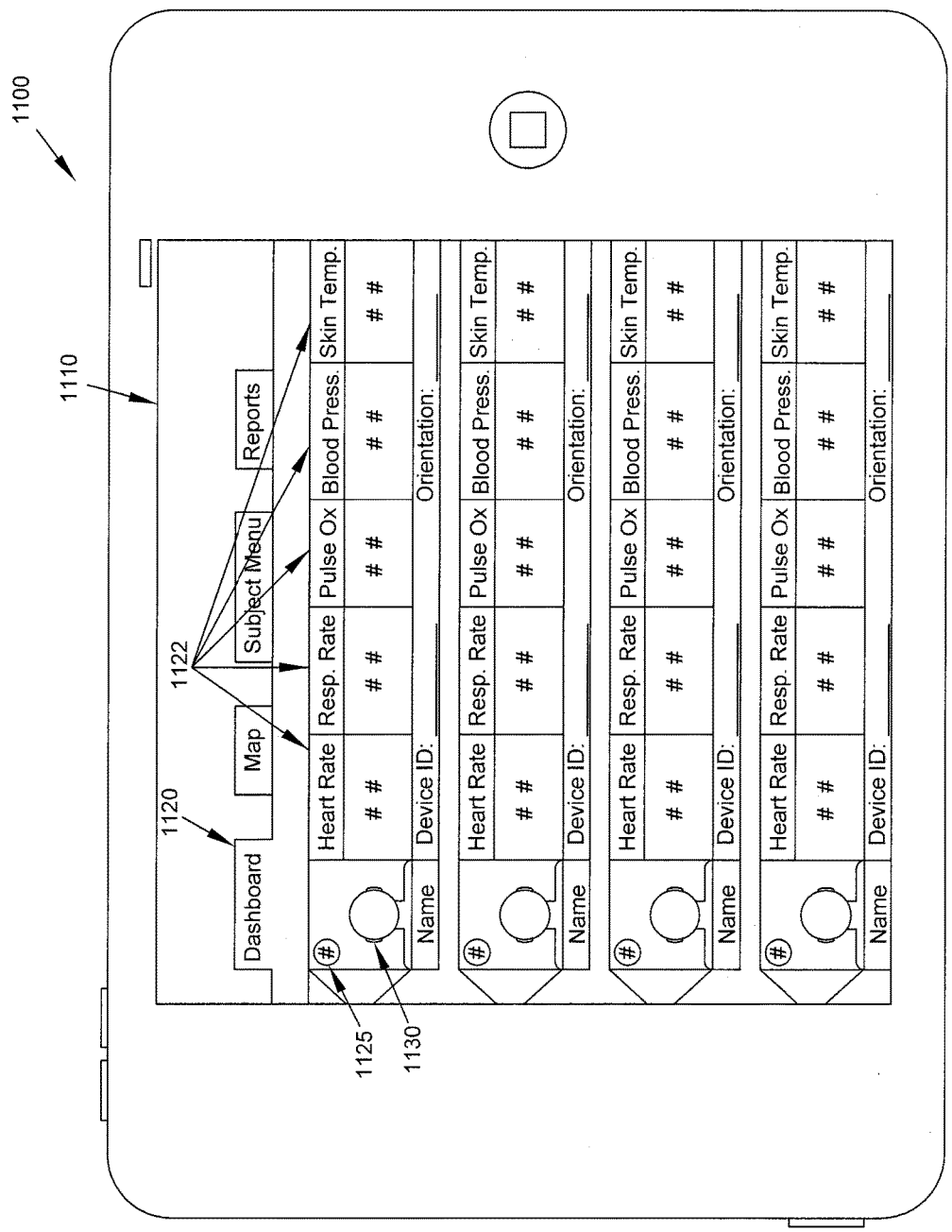
FIGS. 11A-11B are illustrative screenshots of examples of user interfaces of a mobile communication and display device according to some embodiments of the present subject matter.
Figure 11B:
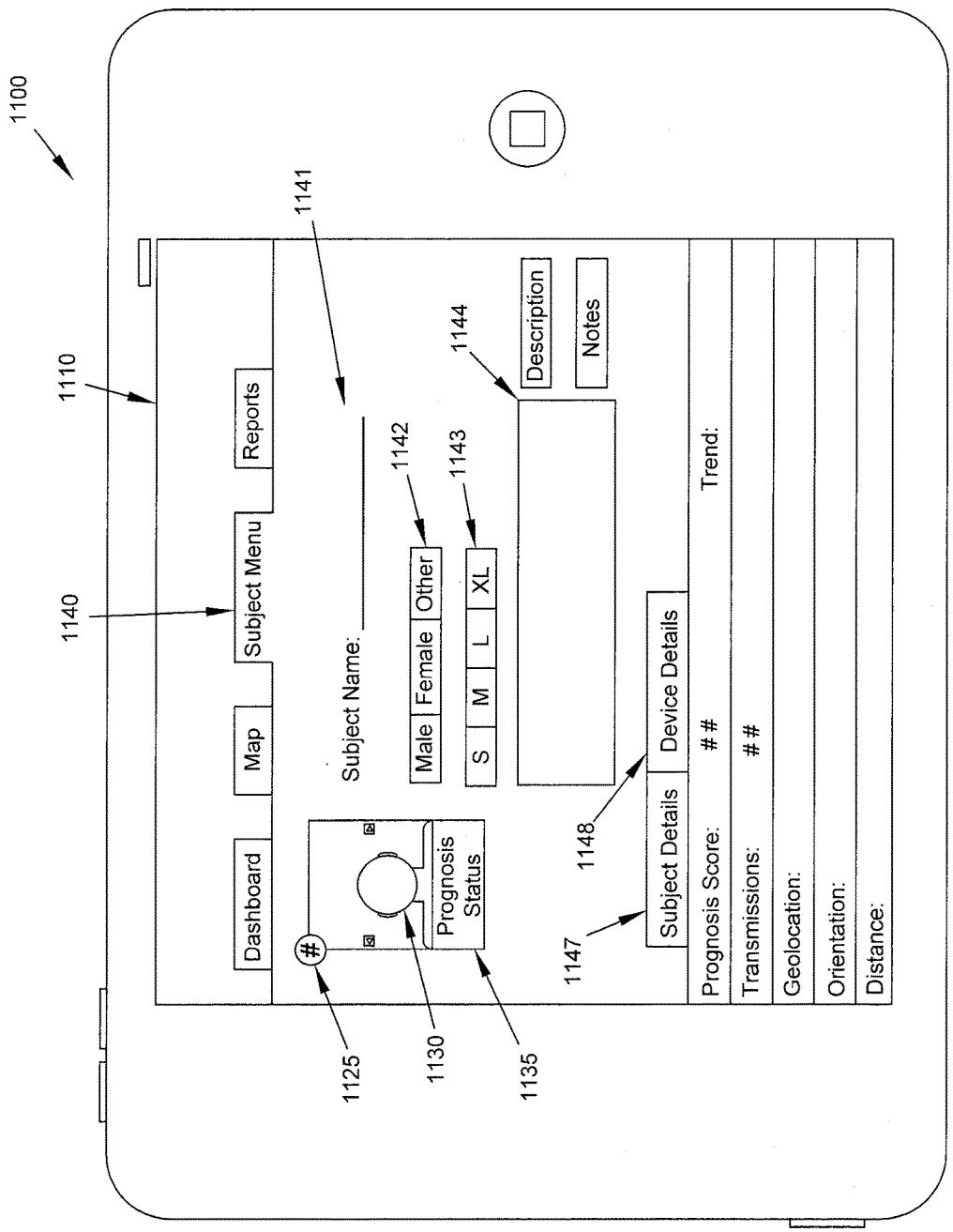

Referring now to FIGS. 11A-11B, illustrative screenshots of examples of user interfaces of a mobile communication and display device according to some embodiments of the present subject matter are provided. In various embodiments, the illustrative screenshots also provide examples of user interfaces of a remote computing device (e.g. 273, 274) for remote administrative and/or medical users. At FIGS. 3A and 3B, illustrative mobile communication and display devices 1100 (and/or remote computing devices) are provided having a user interface according to various embodiments. As shown in FIGS. 11A-11B, a touch-screen display 1110 is provided. In some embodiments, a user (e.g. a first responder, medic) can provide input to a processor of a mobile communication and display device 1100 using an input/output device such as, for example a keyboard, pointing device, e.g., a mouse or a trackball, or other kinds of devices for interaction with user interface 1110.

Input from the user can be received in any suitable form, including acoustic, speech, or tactile input. In various embodiments, a user interaction to select one or more of the portions of the display 1110 may be any suitable form of user selection (e.g. open pinch, closed pinch, tap, swipe, double click, keyboard stroke, etc.). In various embodiments, display 1110 may include one or more spin boxes (not shown), or spinners, or scrolls, having an up arrow or a down arrow, to provide the user with an interface to make another type of user selection of a portions of the display. In various embodiments, a type of user selection may be a selection of an up or down arrow of a spin box (not shown). In various embodiments, a type of user selection may be a selection of a scroll (not shown). In various embodiments, a display 1110 may include one or more swipe bars (not shown), having, for example, a right and left swipe bar to provide the user with an interface to make another type of user selection. In various embodiments, a processor of a mobile communication and display device 1100 can support a markup language (e.g. HTML5, HTML4 with jQuery, CSS3, PHP 5.6) including a Drag and Drop API (e.g. native Drag and Drop API) to enable display 1110 to receive a user selection (e.g. a drag tap and hold, a drag click, a drag mouse click, etc.) of information in one portion of display 1110 and execute a Drag and Drop event such that such selected information is dragged over display 1110 and dropped over information in another portion of display 1110. may be a Long Touch, or a Long Press, or a Long Click, type of user selection. In various embodiments, a processor of a mobile communication and display device 1100 can support a markup language (e.g. HTML5, HTML4 with jQuery, CSS3, PHP 5.6)) including a Long Touch API programmed to have long touch attributes to implement a Long Touch operation (e.g. Long-Click ( )) with displayed objects to enable display 1110 to receive a user selection (e.g. a long touch, a long click, a long press, a focus of a cursor over a portion with navigation-keys or a trackball and a long press of an "enter" key or trackball, etc.) of information in one portion of display 1110, receive another selection (e.g. a tap, a touch, a click, a press) of information in another portion of display 1110, and execute a Long Touch event to associate (e.g. pair) the information in the respective portions of display 1110.

In the illustrated embodiments, a mobile communication and display device 1100 including the touch screen display 1110 is provided. In various embodiments, the illustrative screenshots also provide examples of user interfaces of a remote computing device (e.g. 273, 274) including a touch screen display for remote administrative and/or medical users. As described above, mobile communication and display device 1100 may include any suitable device such as, for example, a laptop, a personal computer, a smart phone, a smart watch, a personal digital assistant, a cellular phone, a tablet, an electronic personal planner, a slate tablet, a booklet computer, a convertible notebook, a phablet, a command and control system having a common operational picture (COP) or other situational awareness display, a human-wearable computing device, etc. For example, an illustrative touch-screen display 1110 may be any suitable touch screen display. For example, touch screen display 1110 may be a cathode ray tube (CRT) touch screen display, a liquid crystal touch screen display (LCD), a LCD resistive touch screen display, a LCD capacitive touch screen display, a LCD multi-touch capable touch screen display, etc. In some embodiments, display 1110 is a display that is enabled by an input of the user that is non-tactile.

In the illustrated examples of FIGS. 11A and 11B, display 1110 includes a tab selectable parameter 1120 which enables a user to toggle between displaying a dashboard of subjects (FIG. 2, 200-N), a "map" display (not shown), a subject (FIG. 2, 200-N) display, a reports display, and other suitable displays. In the illustrated embodiments of FIG. 11A, a "dashboard" display is selected at a tab selectable parameter 1120 to display a dashboard of subjects (FIG. 2, 200-N), generated, real-time, human readable values of physiological signs of such subjects (1122), a real-time orientation of such subjects, a triage prioritization order of the respective subjects (1125), descriptive (1130) and/or identifying data of such subjects, identifying information of each corresponding monitoring device, and other suitable information. Any suitable selectable parameter (e.g. inline image) can be provided to toggle between various user interfaces including, for example, a portion to toggle between descriptive data of a subject (1130) and more detailed descriptive data of such subject, a portion to toggle between one or more physiological signs of such subjects (1122) and a historical and/or predictive trend for the one or more physiological signs of such subjects, a portion to toggle between a triage prioritization order of the respective subjects (1125) and a historical triage prioritization order of the respective subjects, playback, video, help, chat, etc. user interfaces, and for a user to communicate selected information to a command center (e.g. FIG. 2, 273, 274).

In various embodiments, a "map" display (not shown) is selected at a map selectable parameter/tab to display map data, e.g. map data showing the real-time location of one or more of the monitored subjects, the subjects in one or more monitoring groups, users (e.g. medics, first responders), etc. Various mapping functions can be provided to the user when a "map" display is selected at map selectable parameter/tab including, for example, a zooming function, a panning function (e.g. absolute or relative north, south, east, west, up, down, left, right, etc.), a map type selection (e.g. maps defined by the user for a particular environment, maps with or more overlays, satellite imagery, map grids, navigational charts, etc.) including a drop-down or other selection-type menu (e.g. spin box, text box, etc.), concentric distance circles, and any suitable mapping functions. In various embodiments, maps may be map-based, satellite map-based, topographically based, road-based, or based on custom maps for known areas such as a hospital waiting room. In various embodiments, users, administrators, or medical roles, can select subjects or users on the map for all available detail on that subject or user.

In the illustrated embodiments of FIG. 11B, a "Subject Menu" display is selected at a tab selectable parameter 1140 to display more detailed information regarding a selected subject (FIG. 2, 200-N), descriptive (1130) and/or identifying data of the selected subject (e.g. subject name 1141, subject sex 1142, subject size 1143), a real-time triage prioritization order of the selected subject (1125), a real-time prognosis status (e.g. Critical, Urgent, Routine) for the selected subject, a portion to toggle between subject details (1147) and corresponding monitoring device (1148) details, subject details such as, for example, a real-time prognosis score and trend of the selected subject, real-time number of transmissions received from the monitoring device corresponding to the selected subject, real-time orientation of the selected subject, real-time geolocation of the selected subject, real-time distance of the selected subject from the user of device 1100, corresponding monitoring device (1148) details such as, for example, a patch version of the corresponding monitoring device, an RFID or QR code of the corresponding monitoring device, a real-time battery life (e.g. remaining battery) of the corresponding monitoring device, a real-time signal strength (e.g. RSSI) of the corresponding monitoring device, a real-time operating mode of the corresponding monitoring device, a real-time power mode of the corresponding monitoring device, any real-time error codes of the corresponding monitoring device, real-time environmental parameters measured around the monitoring device, and other suitable information. Any suitable selectable parameter (e.g. inline image) can be provided to toggle between various user interfaces including, for example, a portion to toggle between descriptive data of a selected subject, and descriptive data of another subject, generated, real-time, human readable values of physiological signs of a selected subject, real-time ZMIST MEDEVAC or CASEVAC form data (including data automatically pre-populated by subject monitoring core 240-N, prognosis engine 250, triage prioritizing engine 260-A), thresholds and/or weighting factors for the selected subject, a map for the selected subject, pictures of the selected subject and his/her injuries and/or environment, a historical triage prioritization order of the selected subject, a historical prognosis of the selected subject, etc.

As shown in FIGS. 11A and 11B, display 1110 can include various menus for selection by the user to display various features provided by subject monitoring core 240-N, prognosis engine 250, triage prioritizing engine 260-A, and/or communication interfaces A 246 and B 247, including, for example, forensics functions to enable the user to interface with prognosis engine 250, triage prioritizing engine 260-A, and/or subject monitoring core 240-N to provide various forensics-based services to the user such as playback services, trend/pattern analysis services (e.g. internal injuries, crashing subjects), etc., entering, editing or modifying data services to enable the user to interface with prognosis engine 250, triage prioritizing engine 260-A, and/or subject monitoring core 240-N to enter, edit or modify data including, for example, descriptive data regarding any of the respective subjects and/or respective monitoring devices, notes or further description (1144), photos, videos, regarding any of the respective subjects, injuries, environment, MEDEVAC or CASEVAC routes, information for any non-automatically pre-populated lines of M.I.S.T. reports, information for any non-automatically pre-populated lines of (9) line MEDEVAC forms, etc., manual assignment of monitoring devices to subjects, manual linking of subjects to medical records, manual adding of a monitoring device to an ignore list, manual adding of one or more subjects to a black list, manually modify a triage prioritization order, manually modify severity thresholds and/or prognosis weighting factors, save subject information to a local memory of monitoring device, active tactical communication services to enable the user to interface with communication interface B 247, including in connection with prognosis engine 250, triage prioritizing engine 260-A, and/or subject monitoring core 240-N, and one or more command center users via chat, voice communications, etc. to request, view/obtain a status of, and/or call off MEDEVAC or CASEVAC services, receive remote monitoring and care instructions, request linking to medical records of subjects, real-time data viewing and management services to enable the user to interface with prognosis engine 250, triage prioritizing engine 260-A, and/or subject monitoring core 240-N to view and manage real-time data including, viewing active physiological signs, and/or enlarged physiological graphs, of one or more respective subjects, viewing active status of respective monitoring devices (e.g. malfunctioning sensors, battery life), viewing streaming video of the accident scene, notification services (not shown) to enable the user to interface with communications interface 170, including in connection with prognosis engine 250, triage prioritizing engine 260-A, and/or subject monitoring core 240-N, transfer communication services to enable the user to interface with communication interface B 247, including in connection with prognosis engine 250, triage prioritizing engine 260-A, and/or subject monitoring core 240-N, and one or more other users (e.g. medics, first responders), to transfer data between a device 1100 of one user and another device 1100 of another user such as, for example, during turn-over of an accident scene, and provide various notification services such as real-time alerts for high priority subject prognoses and off-display subject events and triggers. Display 1110 can include any suitable menu for displaying and providing a user interface to one or more services provided on mobile communication and display device 1100.

In various embodiments, the display 1110 includes an interface to securely login to, and be authenticated by, the system such as, for example, via password, speech, or biometrics. In various embodiments, the display 1110 includes an interface for a user to messaging and notification features where users of a mobile communication and display device 1100 (and/or administrators and medical role users of remote computing devices) can communicate with each other via text, voice, video, e-mail, or other suitable communication technique, set configurable alerts for each other, and send/receive medical data on subjects. In various embodiments, the display 1110 includes an interface to a monitoring device registration method, where a user can enter potential subjects' medical and descriptive data beforehand, e.g. before a field operation or rescue attempt. In various embodiments, the user can load the potential subjects' medical and descriptive data from a medical and descriptive data service (e.g. via command center server 280 and subject medical data 271), or the user can retrieve this data from a local cache memory of mobile communication and display device (e.g. via subject medical data module 230), or the user can manually enter such information via the user interface 1110. In various embodiments, user interface 1110 includes a plurality of customization options such as, for example, setting user preferences for display options, alert parameters, status levels on when to set color-coded statuses on a per-subject basis, etc.

Figure 12:
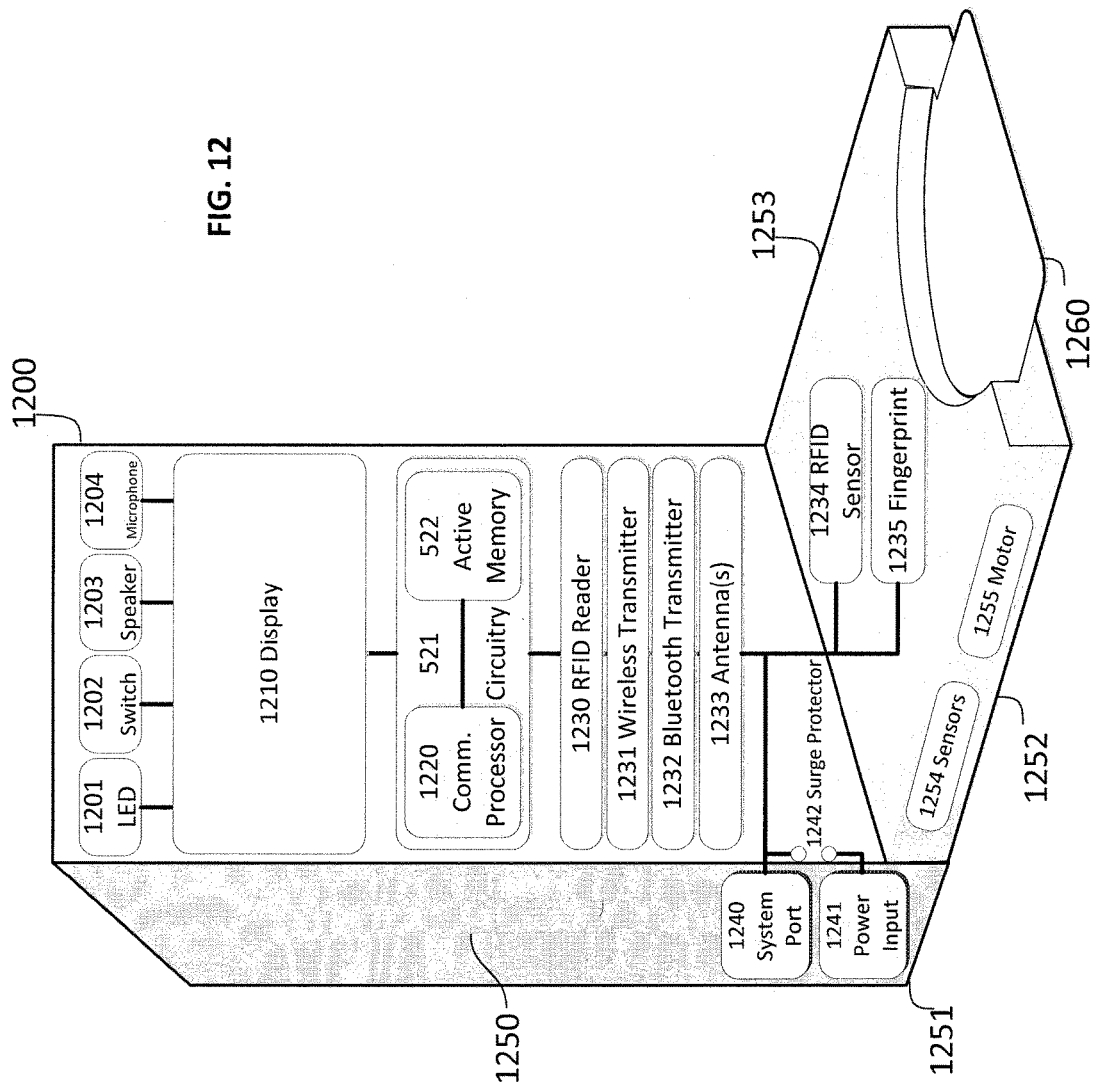
FIG. 12 is a block diagram of an example of a monitoring device dispensing unit in accordance with some embodiments of the present disclosure.

FIG. 12 is a block diagram of an example of a monitoring device dispenser unit 1200 in accordance with some embodiments of the present disclosure. In various embodiments, monitoring device dispenser unit 1200 includes electrical components configured to transmit, receive, process, and display data. In various embodiments, monitoring device dispenser unit 1200 includes a communications processor 1220 configured to manage the data flow of monitoring device dispenser unit 1200. In various embodiments, monitoring device dispenser unit 1200 includes an active memory 1222 such as, for example, an active and/or flash memory. In various embodiments, active memory 1222 is a memory buffer configured to hold instructions and data in a cached state for processing, transmission, and presentation purposes. In various embodiments, monitoring device dispenser unit 1200 includes circuitry 1221 such as, for example, embedded electronic circuitry configured to connect various components of monitoring device dispenser unit 1200 to each other. In various embodiments, monitoring device dispenser unit 1200 includes an RFID reader 1230 such as, for example, an RFID reader configured to read monitoring devices' respective unique identification strings. In various embodiments, an RFID tag of each monitoring device 140 broadcasts its respective unique identification string for registration purposes with monitoring device dispenser unit 1200. In various embodiments, monitoring device dispenser unit 1200 includes RFID sensor 1234 such as, for example, a remote RFID reader antenna on the monitoring device dispenser's 1253 portion of the monitoring device dispenser unit 1200. In various embodiments, monitoring device dispenser unit 1200 includes a barcode reader 1230, a QR code reader 1230, or any suitable identification code reader 1230, configured to read monitoring devices' respective barcode, QR code, or suitable identification code for registration purposes with monitoring device dispenser unit 1200. In various embodiments, monitoring device dispenser unit 1200 includes fingerprint 1235 such as, for example, a fingerprint scanner. Any suitable biometric identification reader may be utilized as fingerprint 1235. In various embodiments, monitoring device dispenser unit 1200 includes transmitter 1231 configured to transmitting the data received, stored, and/or generated, by monitoring device dispenser unit 1200 over a network (e.g. over 802.11, Wi-Fi, 3G/4G/5G cellular, RF, VHF/UHF or other high frequency radio network, satellite network, IP network, a private network, virtual private network (VPN), relay network, the Internet, a Non-secure Internet Protocol Router Network (NIPRNet), a Secret Internet Protocol Router Network (SIPRNet), a Single Channel Ground and Airborne Radio System (SINCGARS), Link-16 (also known as "J2 Coding" or "J2 Messaging" or "TADL" or "SADL"), a cloud computing network, etc.). In various embodiments, monitoring device dispenser unit 1200 includes wireless transmitter 1232 (e.g. Bluetooth) configured to transmit data over a wireless network including, for example, data transmissions between monitoring device dispenser unit 1200 and computer software application, one or more of a plurality of monitoring devices 140, one or more notification devices (not shown), one or more wireless headsets or other audio presentation and recording devices (not shown).

In various embodiments, monitoring device dispenser unit 1200 includes LED 1201 such as, for example, a multi-color LED light configured to programmatically display different color notifications with different flash patterns, frequencies, and intensities. In various embodiments, monitoring device dispenser unit 1200 includes a switch 502 such as, for example, a multi-positional switch configured to activate different modes on monitoring device dispenser unit 1200, such as, for example, a video presentation mode, a disabled mode, a communication mode, a LED active mode, a LED disable mode, a system status mode, a diagnostic mode, etc. In various embodiments, monitoring device dispenser unit 1200 includes a speaker 1203 such as, for example, an audio speaker with a programmatic volume setting, a video camera and speaker combination unit configured to simultaneously take audio and video recordings of, for example, the surroundings of monitoring device dispenser unit 1200 for remote review or visual teleconference communications. In various embodiments, monitoring device dispenser unit 1200 includes a microphone 1204 such as, for example, an audio microphone with a programmatic gain setting. In various embodiments, monitoring device dispenser unit 1200 includes a display 1210 such as, for example, a multi-line display configured to displaying high quality video, graphics, and text.

In various embodiments, monitoring device dispenser unit 1200 is configured to be powered from its power input 1241 is configured to be connected via surge protector 1242 to ensure consistent electrical power flow to various components and electronic subsystems of monitoring device dispenser unit 1200 and prevent damage or overheating from short circuits. In various embodiments, monitoring device dispenser unit 1200 includes system port 1240 configured to provide diagnostics and upgrades to monitoring device dispenser unit 1200. In various embodiments, system port 1240 is a suitable data connection such as, for example USB 3.0. In various embodiments, monitoring device dispenser unit 1200 is configured to be connected via system port 1240 to other computing devices or to flash drives. In various embodiments, monitoring device dispenser unit 1200 includes a side panel 1251 such as, for example, the side panel of monitoring device dispenser unit 1200. In various embodiments, side panel 1251 is the location of the external, wired data connection, and power ports, of monitoring device dispenser unit 1200. In various embodiments, monitoring device dispenser unit 1200 includes compartment 550 configured to be a storage compartment for the monitoring devices. In various embodiments, the monitoring devices are connected via a perforated strip for feeding purposes. In various embodiments, the monitoring devices are loaded into compartment 1250. In various embodiments, compartment 1250 is monitored by one or more of the set of sensors in sensors 1254. In various embodiments, the sensor of the set of sensors that are monitoring compartment 1250 activates motor 1255 within the monitoring device dispenser 1253 assembly. In various embodiments, when requested by a subject or a user (e.g. EMT, first responder, medic) via switch 1202, motor 1255 activates and dispenses a monitoring device. In various embodiments, sensors 1254 included in monitoring device dispenser unit 1200 also include a motion sensor to sense motion (e.g. a waving hand of a subject or a user) underneath the motion sensor of monitoring device dispenser unit 1200, a reader (e.g. a scanner) to read identification card barcodes on the monitoring devices, and/or a reader (e.g. a scanner) to read identification card magnetic stripes on the monitoring devices.

In various embodiments, monitoring device dispenser unit 1200 includes a relay network unit 1270 including electrical components configured to transmit, receive, process, and display data. In various embodiments, relay network unit 1270 includes a communications processor 1280 configured to manage the processing and data flow of relay network unit 1270. In various embodiments, relay network unit 1270 includes active memory 1282 such as, for example, a memory buffer configured to hold instructions and data in a cached state for processing, transmission, and presentation purposes. In various embodiments, relay network unit 1270 includes circuitry 1281 such as, for example, embedded electronic circuitry configured to connect the components of relay network unit 1270 to each other. In various embodiments, relay network unit 1270 includes a location subsystem, such as for example, GPS 1276 including a GPS unit configured to use the global GPS network to determine global coordinates within a predetermined tolerance. In various embodiments, relay network unit 1270 includes a transmitter 1285 configured to transmit the data received, stored, and/or generated, by relay network unit 1270 over a network (e.g. over 802.11, Wi-Fi, 3G/4G/5G cellular, RF, VHF/UHF or other high frequency radio network, satellite network, IP network, a private network, virtual private network (VPN), relay network, the Internet, a Non-secure Internet Protocol Router Network (NIPRNet), a Secret Internet Protocol Router Network (SIPRNet), a Single Channel Ground and Airborne Radio System (SINCGARS), Link-16 (also known as "J2 Coding" or "J2 Messaging" or "TADL" or "SADL"), a cloud computing network, etc.). In various embodiments, relay network unit 1270 includes wireless (e.g. Bluetooth) transceiver 1286 configured to transmit and receive data over a wireless network including, for example, data transmissions between relay network unit 1270 and computer software applications, one or more mobile communication and display devices, and one or more of a plurality of monitoring devices 140. In various embodiments, GPS 1276, transmitter 1285, and wireless transceiver 1286, are configured to connect to antenna(s) 1287 such as, for example, a set of antennas for data transmissions.

In various embodiments relay network unit 1270 includes a battery 1273 such as, for example, a battery configured to power relay network unit 570. In various embodiments, battery 1273 is a long-life battery and, depending on application, can be removable or non-removable. In various embodiments, relay network unit 1270 includes battery 1273 configured to connect to circuitry 1281 via surge protector 1274 to ensure consistent electrical power flow to various components and electronic subsystems of monitoring device dispenser unit 1200 and prevent damage or overheating from short circuits. In various embodiments, relay network unit 1270 includes LED 1271 such as, for example, a multi-color LED light that can programmatically display different color notifications with different flash patterns, frequencies, and intensities. In various embodiments, relay network unit 1270 includes keypad 1272 such as, for example, a keyboard with multi-directional buttons that can provide text inputs and activate different modes on relay network unit 1270.

In various embodiments, relay network unit 1270 includes system port 1284 configured to utilize any suitable wired connection technology configured to transmit data and electricity, such as, for example, MicroUSB, with other computing devices and network nodes, such as, for example, Lightning, 30 pin connectors, USB, Ethernet, parallel connections, RS-232, MIL-STD-144-114A, or other serial connections. In various embodiments, relay network unit 1270 of monitoring device dispenser unit 1200 is configured to be powered, for example, from its system port 1284, battery 1273, or dedicated power input 1283 that is configured to receive suitable electrical inputs such as, for example, 3V, 12V, 110V, and 220V electrical inputs.

In some embodiments, one or more steps of the methods described herein can be implemented by one or more general purpose computers programmed in accordance with the principals discussed herein. In various embodiments, a general computer processor programmed in accordance with various principles described herein is provided in the cloud of a cloud computing environment. In some embodiments, a general computer processor programmed in accordance with various principles is provided at one or more command center servers 280 and/or at an administrator or medical role (273, 274) of the command center services 108. Digital computer systems programmed to perform particular functions pursuant to instructions from program code that implements features of the methods described herein may be special-purpose computers particular to the methods described herein. Computer program code implementing one or more methods described herein may be distributed to users on a non-transient, computer readable storage medium such as, for example, a floppy disk, CD-ROM, or flash memory data storage device, or other suitable distribution storage medium, and may be copied to a hard disk, RAM, or other suitable intermediate, non-transient computer readable storage medium, on a computer. When the programs are to be run, they will be loaded either from their distribution medium or their intermediate storage medium into the execution memory of the computer, configuring the computer to act in accordance with the method of this invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that certain of the described program components and systems can generally be integrated together in a single software product being executed in one or more networks or packaged into multiple software products for execution in the one or more networks.

One or more steps of the processes and logic flows described in this specification can be performed by one or more programmable processors executing one or more computer programs to perform functions by operating on input data and generating output. One or more steps of the processes and logic flows can also be performed by, and apparatus can also be implemented as, special purpose logic circuitry, e.g., an FPGA (field programmable gate array) or an ASIC (application specific integrated circuit).

Various embodiments can be implemented in a cloud computing system that includes, and/or is in communication with, a back end component, e.g., as a data server, or that includes a middleware component, e.g., an application server, or that includes a front end component, e.g., a computer having a GUI or a Web browser through which an operator can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

While various embodiments have been described, it is to be understood that the embodiments described are illustrative only and that the scope of the subject matter is to be accorded a full range of equivalents, many variations and modifications naturally occurring to those of skill in the art from a perusal hereof.

What we claim is:

1. A system for automated triage prioritization, comprising:
a plurality of monitoring devices, each monitoring device comprising a first portion and a second portion, each first portion of each monitoring device configured for deployment on a surface opposite a concha of a respective ear of a respective subject, and each first portion of each monitoring device comprising:
a plurality of physiological sensors comprising:
a pulse oximetry sensor comprising an emitter configured to emit light in a direction toward the concha and a receptor configured to receive light reflected from one or more sources in the direction, the pulse oximetry sensor configured to generate an electronic pulse oximetry signal based on the received, reflected light;
a blood pressure sensor comprising:
an electrocardiograph sensor configured to monitor an electrical potential at the ear surface; and
a motion sensor configured to monitor motion at the ear surface relevant to a motion axis,
the blood pressure sensor configured to generate an electronic blood pressure signal based on the monitored electrical potential and motion;
an orientation sensor configured to monitor an orientation of the respective subject relative to an orientation axis and to generate an electronic orientation signal based on the monitored orientation;
each second portion of each monitoring device comprising:
one or more atmospheric sensors comprising a pressure sensor configured to monitor ambient pressure around a surface of the respective subject and to generate an electronic ambient pressure signal based on the monitored pressure;
a transmitter configured to transmit the generated electronic signals over a first network;
a mobile communication and display device comprising:
a communications interface configured to be coupled to the first network and to receive the transmitted electronic signals over the first network from each of the transmitters of each of the plurality of monitoring devices;
a user interface;
a processor coupled to the communications interface;
a non-transient machine-readable storage medium encoded with program code executable by the processor for:
generating respective machine readable values indicative of pulse oximetry, orientation, and blood pressure for each of the subjects using the received electronic signals;
generating respective human readable values indicative of pulse oximetry and blood pressure for each of the subjects using the received electronic signals;
generating a respective prognosis score for each of the subjects using the generated machine readable values;
selecting a triage prioritization order of the subjects using the generated prognosis scores; and
displaying the generated respective human readable values for at least two of the subjects on respective portions of the user interface based on the selected triage prioritization order.

2. The system of claim 1, wherein each second portion of each monitoring device is configured for deployment on another surface of a respective subject and wherein the first portion is configured to transmit the first portion generated electronic signals to the second portion.

3. The system of claim 2, wherein the first portion is configured to transmit the first portion generated electronic signals to the second portion over a wired connection.

4. The system of claim 1, wherein the one or more atmospheric sensors further comprises at least one of an ambient temperature sensor, a humidity sensor, a UV index sensor and an ambient light sensor, wherein each of the one or more atmospheric sensors is configured to monitor a corresponding environmental parameter around the surface of the respective subject and to generate a corresponding electronic signal based on the monitored environmental parameter, and wherein the storage medium is further encoded with program code executable by the processor for generating respective machine readable values indicative of the monitored environmental parameter for each of the subjects using the received electronic signals.

5. The system of claim 1, wherein the communications interface is further configured to be coupled to a second network, and wherein the storage medium is further encoded with program code executable by the processor for:

generating a plurality of bindings between respective monitoring devices and respective subjects using registration information received via the second network; and modifying the display of the generated respective human readable values for the at least two subjects based on the generated bindings.

6. The system of claim 1, wherein the orientation sensor and the motion sensor are the same sensor.

7. The system of claim 1, wherein the storage medium is further encoded with program code executable by the processor for:

generating respective severity scores for each of pulse oximetry, orientation, and blood pressure, for each of the plurality of subjects using the generated machine readable values and a plurality of pre-determined thresholds, wherein the step of generating a prognosis score for each of the plurality of subjects further uses the generated respective severity scores and a plurality of pre-determined weighting factors.

8. The system of claim 7, wherein the plurality of physiological sensors in each first portion of each monitoring device further comprise a respiratory rate sensor configured to monitor respiratory rate at the ear surface of the respective subject and to generate an electronic respiratory rate signal based on the monitored respiratory rate, and wherein the storage medium is further encoded with program code executable by the processor for:

generating machine readable values indicative of respiratory rate for each of the subjects using the received electronic respiratory rate signals;

generating human readable values indicative of respiratory rate for each of the subjects using the received electronic respiratory rate signals; and generating respiratory rate severity scores for each of the plurality of subjects using the generated machine readable values indicative of respiratory rate and the plurality of pre-determined thresholds.

9. The system of claim 8, wherein the storage medium is further encoded with program code executable by the processor for:

detecting a respiratory rate severity score for a subject that exceeds a predetermined respiratory rate severity score;

generating a new prognosis score for the subject using the generated respiratory rate severity score;

raising the triage prioritization position of the subject in the triage prioritization order over the other subjects of the plurality of subjects based on the generated new prognosis score, the stored prognosis scores for the other subjects, and the stored triage prioritization order; and in response to raising the triage prioritization position of the subject, changing a top portion of the user interface to display the generated human readable values for the subject.

10. The system of claim 1, wherein the storage medium is further encoded with program code executable by the processor for storing the generated respective prognosis scores for each of the subjects and the selected triage prioritization order in cache memory of the mobile communication and display device.

11. The system of claim 10, wherein each second portion of each monitoring device further comprises a microphone configured to monitor sound around the surface of the respective subject and to generate an electronic audio signal based on the monitored sound, and wherein the storage medium is further encoded with program code executable by the processor for:

detecting a predetermined sound type in at least one of the received electronic audio signals using the received electronic audio signals and audio signal patterns stored in non-transient memory of the mobile communication and display device;

generating machine readable values indicative of the detected predetermined sound type using the at least one of the received electronic audio signals;

generating a new prognosis score for the respective subject using the generated machine readable values indicative of the detected predetermined sound type;

detecting a change in the triage prioritization order for the respective subject and at least another subject of the plurality of subjects based on the stored prognosis scores for the respective subject and the at least another subject, the generated respective new prognosis score for the respective subject, and the stored triage prioritization order; and in response to detecting the change in the triage prioritization order for the respective subject and the at least another subject, changing the respective portions of the display of the respective generated human readable values for the respective subject and the at least another subject.

12. A computer-implemented method for automated triage prioritization, the method comprising, on a mobile communication and display device:

communicating with a plurality of monitoring devices via a first network to receive a plurality of electronic signals regarding a plurality of subjects, the received plurality of electronic signals corresponding to:

a respective plurality of real-time physiological signs, a respective orientation relative to an orientation axis, and a respective location, monitored by each of the plurality of monitoring devices, the real-time physiological signs comprising pulse oximetry, electrical potential, and motion relative to a motion axis, at a surface of the respective monitoring device; and one or more respective atmospheric conditions monitored by each of the plurality of monitoring devices, the one or more atmospheric conditions comprising ambient pressure around at least a portion of the respective monitoring device;

retrieving registration information regarding the plurality of monitoring devices from a non-transient memory of the mobile communication and display device, the retrieved registration information binding respective monitoring devices of the plurality of monitoring devices to respective subjects of the plurality of subjects;

generating respective machine readable values indicative of location and orientation of each of the plurality of subjects using the received electronic signals corresponding to location and orientation, and the retrieved registration information;

generating a respective machine readable value and a respective human readable value indicative of blood pressure for each of the plurality of subjects using the received electronic signals corresponding to motion, electrical potential, and ambient pressure, and the retrieved registration information;

generating a respective machine readable value and a respective human readable value indicative of pulse oximetry for each of the plurality of subjects using the received electronic signals corresponding to motion and pulse oximetry, and the retrieved registration information;

generating respective severity scores for each of pulse oximetry, orientation, location, and blood pressure, for each of the plurality of subjects using the generated machine readable values for the respective subject and a plurality of pre-determined thresholds;

generating a respective prognosis score for each of the plurality of subjects using the generated respective severity scores for the respective subject and a plurality of pre-determined weighting factors;

generating a triage prioritization order for the plurality of subjects using the generated prognosis scores;

detecting a change in the triage prioritization order for at least two subjects of the plurality of subjects based on the generated prognosis scores for the at least two subjects, and information stored in a cache memory of the mobile communication and display device, wherein the stored information comprises stored respective prognosis scores for the at least two subjects and a stored triage prioritization order; and in response to detecting the change in the triage prioritization order for the at least two subjects, changing a display of the respective generated human readable values for the at least two subjects.

13. The method for automated triage prioritization of claim 12, further comprising, on the mobile communication and display device:

detecting a change in the prognosis score for at least one subject of the plurality of subjects based on the generated prognosis score for the at least one subject and a stored prognosis score for the at least one subject in the cache memory; and in response to detecting the change in the prognosis score, changing a display of the respective generated human readable values for the at least one subject.

14. The method for automated triage prioritization of claim 12, further comprising, on the mobile communication and display device:

detecting a change in at least one of the respective severity scores for at least one subject of the plurality of subjects based on the generated severity scores for the at least one subject and stored severity scores for the at least one subject in the cache memory; and in response to detecting the change in the at least one of the respective severity scores, changing a display of one or more of the respective generated human readable values for the at least one subject.

15. The method for automated triage prioritization of claim 12, further comprising, on the mobile communication and display device:

detecting a binding failure condition for one or more of the plurality of monitoring devices based on the retrieved registration information; and in response to detecting the binding failure condition, communicating via a second network with a remote server to receive registration information regarding the one or more monitoring devices with the detected binding failure condition.

16. The method for automated triage prioritization of claim 12, further comprising, on the mobile communication and display device:

detecting a binding failure condition for one or more of the plurality of monitoring devices based on the retrieved registration information; and in response to detecting the binding failure condition, communicating via the first network to receive biometric information of the respective subject on whom the one or more monitoring devices with the detected binding failure condition is deployed.

17. The method for automated triage prioritization of claim 12, further comprising, on the mobile communication and display device:

communicating via a second network with a remote server to receive medical information for at least one subject of the plurality of subjects based on the generated triage prioritization order;

generating a new prognosis score for the at least one subject using medical information received via the second network, the plurality of pre-determined weighting factors, and a stored prognosis score for the at least one subject;

detecting a change in the triage prioritization order for the at least one subject and at least another subject of the plurality of subjects based on the generated new prognosis score for the at least one subject, stored prognosis scores for the at least one subject and the at least another subject, and a stored triage prioritization order; and in response to detecting the change in the triage prioritization order for the at least one subject and the at least another subject, changing a display of the respective generated human readable values for the at least one subject and the at least another subject.

18. The method for automated triage prioritization of claim 12, further comprising, on the mobile communication and display device:

selecting two or monitoring groups based on the generated machine readable values indicative of location of each of the plurality of subjects; wherein each of the monitoring groups comprises two or more subjects;

generating a respective triage prioritization order for the respective subjects in each monitoring group of the two or more monitoring groups using the generated prognosis scores for the respective subjects in each monitoring group;

displaying the generated respective human readable values for the respective subjects in at least one monitoring group on respective portions of the user interface based on the generated triage prioritization order for the at least one monitoring group.

19. A system for automated triage prioritization, comprising:

a mobile communication and display device comprising:
a communications interface configured to be coupled to a first network and to receive transmitted electronic signals regarding a plurality of subjects over the first network from a plurality of monitoring devices, the received plurality of electronic signals corresponding to:
a plurality of real-time physiological parameters monitored at a respective surface of each of the plurality of subjects by a respective one of the plurality of monitoring devices;
an orientation relative to an orientation axis, and a location, of each of the plurality of subjects monitored by the respective one of the plurality of monitoring devices; and
one or more environmental parameters monitored around each of the plurality of subjects by the respective one of the plurality of monitoring devices;

a user interface;
a processor coupled to the communications interface;
   a non-transient machine-readable storage medium encoded with program code executable by the processor for:
      generating respective machine readable values indicative of each of a plurality of physiological signs for each of the respective subjects using the received electronic signals corresponding to the plurality of real-time physiological parameters of each respective subject;
      generating respective human readable values indicative of each of at least two of the plurality of real-time physiological signs for each of the subjects using the received electronic signals corresponding to the plurality of real-time physiological parameters of each respective subject;
      generating respective machine readable values indicative of each of location and orientation of each of the subjects using the received electronic signals corresponding to the location and orientation of each respective subject;
      selecting two or monitoring groups based on the generated machine readable values indicative of the respective location of each respective subject; wherein each of the monitoring groups comprises two or more subjects;
      generating respective severity scores for each of the plurality of physiological signs, orientation, and location for each of the plurality of subjects using the generated machine readable values corresponding to the plurality of real-time physiological parameters of each respective subject and a plurality of pre-determined thresholds;
      generating a prognosis score for each of the plurality of subjects using the generated respective severity scores of each respective subject and a plurality of pre-determined weighting factors;
      generating a respective triage prioritization order for the respective subjects in each monitoring group of the two or more monitoring groups using the generated prognosis scores for the respective subjects in each monitoring group; and
      displaying the generated respective human readable values for at least two of the respective subjects in at least one monitoring group on respective portions of the user interface based on the generated triage prioritization order for the at least one monitoring group.

20. The system of claim 19, wherein the received plurality of electronic signals further corresponds to a respective battery life status of each of the plurality of monitoring devices wherein the storage medium is further encoded with program code executable by the processor for:
   generating machine readable values indicative of battery life status of each of the plurality of monitoring devices using the received electronic signals corresponding to the battery life status of each respective monitoring device; wherein the step of generating respective severity scores for each of the plurality of subjects further comprises generating a severity score for remaining battery life of the respective one of the plurality of monitoring devices using the generated machine readable values corresponding to the battery life status of each respective monitoring device and the plurality of pre-determined thresholds.

* * * * *